United States Patent
Stehberg Liberman et al.

(10) Patent No.: US 9,879,058 B2
(45) Date of Patent: Jan. 30, 2018

(54) USE OF COMPOUNDS THAT SELECTIVELY MODULATE ASTROCYTIC RELEASE OF SUBSTANCES THROUGH HEMICHANNELS OF CONNEXINS AND PANNEXINS, WITHOUT INFLUENCING GAP JUNCTIONS, FOR THE TREATMENT OF PSYCHIATRIC DISORDERS

(71) Applicants: Universidad Andres Bello, Santiago (CL); Universiteit Gent, Ghent (BE); Katholieke Universiteit Leuven, KU Leuven R&D, Leuven-Vlaams-Brabant (BE)

(72) Inventors: Jimmy Stehberg Liberman, Santiago (CL); Luc Gilbert Leybaert Sinia, Bachte-Maria-Leerne (BE); Geert Albert Bultynck Demets, Tildonk-Vlaams-Brabant (BE); Mauricio Antonio Retamal Lucero, Santiago (CL); Fernando Danilo Gonzalez Nilo, Santiago (CL)

(73) Assignees: Universidad Andres Bello (CL); Universiteit Gent (BE); Katholieke Universiteit Leuven, Ku Leuven R & D (BE)

( * ) Notice: Subject to any disclaimer, the term of this patent is extended or adjusted under 35 U.S.C. 154(b) by 0 days.

(21) Appl. No.: 14/404,358

(22) PCT Filed: May 31, 2013

(86) PCT No.: PCT/IB2013/054486
§ 371 (c)(1),
(2) Date: Nov. 26, 2014

(87) PCT Pub. No.: WO2013/179264
PCT Pub. Date: Dec. 5, 2013

(65) Prior Publication Data
US 2015/0337018 A1    Nov. 26, 2015

Related U.S. Application Data

(60) Provisional application No. 61/653,148, filed on May 30, 2012.

(51) Int. Cl.
| | |
|---|---|
| *A01N 43/00* | (2006.01) |
| *A61K 31/33* | (2006.01) |
| *C07K 14/435* | (2006.01) |
| *C07K 9/00* | (2006.01) |
| *A61K 38/39* | (2006.01) |
| *C07K 14/78* | (2006.01) |
| *A61K 38/00* | (2006.01) |

(52) U.S. Cl.
CPC ............ *C07K 14/435* (2013.01); *A61K 38/39* (2013.01); *C07K 9/00* (2013.01); *C07K 14/78* (2013.01); *A61K 38/00* (2013.01); *C07K 2319/00* (2013.01)

(58) Field of Classification Search
USPC ........................................................ 514/183
See application file for complete search history.

(56) References Cited

U.S. PATENT DOCUMENTS

| | | | |
|---|---|---|---|
| 2007/0072939 A1 | 3/2007 | Kupper | |
| 2010/0029613 A1 | 2/2010 | Nedergaard et al. | |
| 2010/0233084 A1 | 9/2010 | Narasimhaswamy et al. | |

FOREIGN PATENT DOCUMENTS

| | | |
|---|---|---|
| EP | 2 322 149 | 5/2011 |
| EP | 2 344 146 | 7/2011 |
| WO | 2006/134494 | 12/2006 |
| WO | 2007/002285 | 1/2007 |
| WO | 2010/029131 | 3/2010 |

OTHER PUBLICATIONS

Giaume, C., "Astroglial networks: a step further in neuroglial and gliovascular interactions," 2010, Nature Reviews, *Neuroscience*, vol. 11, pp. 87-99.

(Continued)

*Primary Examiner* — Marcos Sznaidman
(74) *Attorney, Agent, or Firm* — DLA Piper LLP (US)

(57) ABSTRACT

The present invention is related to the use of compounds or pharmaceutically acceptable salts thereof that modulate astrocytic release of substances through connexin and pannexin hemichannels, for the treatment of psychiatric disorders. Compounds or pharmaceutically acceptable salts thereof used in the present invention comprise any compound that differentially modulates, blocks, opens, inhibits, and/or activates connexin and/or pannexin hemichannels from astrocytes while not affecting gap junctions. The invention is also related to a method for treating psychiatric disorders, comprising administering to a mammal or human a therapeutically effective amount of a compound or a pharmaceutically acceptable salt thereof, that modulates astrocytic release of substances through connexin and pannexin hemichannels. Pharmaceutical compositions and a screening method are also considered in the present invention. Examples are shown for connexin 43, connexin 30 and pannexin 1 hemichannel modulators shown not to affect gap junctions, in the form of both non peptide compounds and peptides which were tested in different models for psychiatric disorders, comprising PTSD, memory, anxiety and depression.

7 Claims, 6 Drawing Sheets

(56) References Cited

OTHER PUBLICATIONS

Orellana, J., "Hypoxia in high glucose followed by reoxygenation in normal glucose reduces the viability of cortical astrocytes through increased permeability of connexin 43 hemichannels," *Glia*, 2010, vol. 58, pp. 329-343.

Sáez, J., "Cell membrane permeabilization via connexin hemichannels in living and dying cells," 2010, *Experimental Cell Research*, vol. 316, pp. 2377-2389.

Ledoux, J., "The amygdala," *Current Biology*, vol. 17, No. 20, pp. R868-R874, 2007.

Juszczak, G., "Properties of gap junction blockers and their behavioural, cognitive and electrophysiological effects: animal and human studies," 2009, *Progress Neuro-psychopharmacology & Biological Psychiatry*, vol. 33, pp. 181-198.

Evans, W., "Mimetic Peptides as Blockers of Connexin Channel-Facilitated Intercellular Communication", 2007, *Cell Communication and Adhesion*, vol. 14, pp. 265-273.

Nagy, J., "Connexin26 in adult rodent central nervous system: demonstration at astrocytic gap junctions and colocalization with connexin30 and connexin43," 2001, *Journal of Comparative Neurology*, vol. 441, pp. 302-323.

Ryan, P., "Central relaxin-3 receptor (RXFP3) activation decreases anxiety- and depressive-like behaviours in the rat," 2013, *Behavioural Brain Research*, vol. 244, pp. 142-151.

Enkel, T., "Differential effects of subchronic Phencyclidine on anxiety in the light-enhanced startle-, light/dark exploration- and open field tests," 2013, *Behavioural Brain Research*, vol. 243, pp. 61-65.

Porsolt, R., "Behavioural despair in rats and mice: strain differences and the effects of imipramine," 1978, *European Journal of Pharmacology*, vol. 51, pp. 291-294.

Nagy, J., "Evidence for the co-localization of another connexin with connexin-43 at astrocytic gap junctions in rat brain," 1997, *Neuroscience*, vol. 78(2), pp. 533-548.

Orellana, J., "Glial hemichannel and their involvement in aging and neurodegenerative diseases," 2012, *Rev. Neurosci.*, vol. 23(2). pp. 163-177.

Karpuk, N., "Neuroinflammation leads to region-dependent alterations in astrocyte gap junction communication and hemichannel activity," 2011, *J Neurosci.*, vol. 31, pp. 414-425.

Sosinsky, G., "Pannexin channels are not gap junction hemichannels," 2011, *Channels*, vol. 5 No. 3, pp. 193-197.

Lee, S., "Channel-Mediated Tonic GABA Release from Glia", *Science*, vol. 330, pp. 790-796, 2010.

Rudkouskaya, A., "Two conventional protein kinase C isoforms, alpha and beta I, are involved in the ATP-induced regulation of volume-regulated anion channel and glutamate release in cultured astrocytes," *Journal of Neurochemistry*, vol. 105, pp. 2260-2270, Jun. 1, 2008.

Görg, B., "Ammonia triggers exocytotic release of L-glutamate from cultured rat astrocytes," 2010, *Glia*, vol. 58, pp. 691-705.

Rash, J., "Identification of cells expressing Cx43, Cx30, Cx26, Cx32 and Cx36 in gap junctions of rat brain and spinal cord," 2001, *Cell Communication and Adhesion*, vol. 8, pp. 315-320.

Gosejacob, D., "Role of astroglial connexin30 in hippocampal gap junction coupling," 2011, *Glia*, vol. 59, pp. 511-519.

Alves, S. H., "Anxiogenic effects in the rat elevated plus-maze of 5-HT(2C) agonists into ventral but not dorsal hippocampus," 2004, *Behavioural Pharmacology*, vol. 15, 37-43.

Carrigan, C., "The engineering of membrane permeable peptides," 2005, *Analytical Biochemistry*, vol. 341, pp. 290-298.

Wang, N., "Selective inhibition of Cx43 hemichannels by Gap19 and its impact on myocardial ischemia/reperfusion injury," 2013, *Basica Res. Cardiol.*, vol. 108, pp. 1-26.

Orellana, J.A., et al., "ATP and glutamate released via astroglial connexin 43 hemichannels mediate neuronal death through activation of pannexin 1 hemichannels," 2011, *J. Neurochem*, vol. 118, pp. 826-840.

Ye, Z.C., "Functional hemichannels in astrocytes: a novel mechanism of glutamate release," 2003, *J. Neurosci.* 1, vol. 23, pp. 3588-3596.

Huang, Y., "Pannexin1 is Expressed by Neurons and Glia but Does Not Form Functional Gap Junctions," *Glia*, 2007, 55:46-56.

Perea, G., "Tripartite synapses: astrocytes process and control synaptic information," *Trends Neurosci.* 32, pp. 421-431, 2009.

Achour, B. S., "Glia: the many ways to modulate synaptic plasticity," *Neurochem Int.* 57, 2010, pp. 440-445.

Henneberger, C., "Long-term potentiation depends on release of D-serine from astrocytes," 2010, *Nature*, 463, pp. 232-236.

Yang, Y., "Contribution of astrocytes to hippocampal long-term potentiation through release of D-serine," *Proc Natl Acad Sci U S A*, vol. 100, pp. 15194-15199, 2003.

Parpura, V., "Mechanisms of glutamate release from astrocytes: gap junction "hemichannels", purinergic receptors and exocytotic release," *Neurochem Int.* 45 pp. 259-264, 2004.

Gourine, A.V., "Astrocytes control breathing through pH-dependent release of ATP," 2010, *Science* 329, pp. 571-575.

Haydon, P., "Astrocyte Control of Synaptic Transmission and Neurovascular Coupling," 2006, *Physiol Rev*, vol. 86., pp. 1009-1031.

Frisch, C., "Mice with astrocyte-directed inactivation of connexin43 exhibit increased exploratory behaviour, impaired motor capacities, and changes in brain acetylcholine levels," 2003, *European Journal of Neuroscience*, vol. 18, pp. 2313-2318.

Perea, G., "GLIA modulates synaptic transmission," 2010, *Brain Research Review*, vol. 63, pp. 93-102.

Jiang, S., "Glutamate release through connexin 43 by cultured astrocytes in a stimulated hypertonicity model," 2011, *Brain Research*, 1392, pp. 8-15.

Garré, J., "FGF-1 induces ATP release from spinal astrocytes in culture and opens pannexin and connexin hemichannels," 2010, *PNAS*, vol. 107, No. 52, pp. 22659-22664.

Iwabuchi, S., "Functional significance of the negative-feedback regulation of ATP release via pannexin-1 hemichannels under ischemic stress in astrocytes," 2011, *Neurochemistry International*, vol. 58, pp. 376-384.

Iglesias, R., "Pannexin 1: the molecular substrate of astrocyte "hemichannels"," 2009, *J Neurosci.*, vol. 29, pp. 7092-7097.

Perea, G., "Astrocytes potentiate transmitter release at single hippocampal synapses," 2007, *Science*, vol. 317, pp. 1083-1086.

AAL69545, GenBank AAL69545.1, connexin 43 [Ovis aries], Feb. 4, 2002 [online], http://www.ncbi.nlm.nih.gov/protein/18491309?report=genbank&log$=protalign&blast_rank=2&RID=MB54Z2XK015.

Mitterauer, BJ, "The syncytiopathy hypothesis of depression: Downregulation of glial connexins may protract synaptic information processing and cause memory impairment," 2010, *Medical Hypothesis*, vol. 74, pp. 497-502.

Desplantez, T, "Gap26, a connexin mimetic peptide, inhibits currents carried by connexin43 hemichannels and gap junction channels," *Pharmacol. Research*, 2012, 65, pp. 546-552.

Davidson, J. O.,"Connexin hemichannel blockade improves outcomes in a model of fetal ischemia," *Annals Neurology*, 2012, vol. 71, pp. 121-132.

Sun, J., "Gap Junction Dysfunction in the Prefrontal Cortex Induces Depressive-Like Behaviors in Rats," *Neuropsychopharmacology*, 2012, vol. 37, pp. 1305-1320.

O'Carroll, S.,"Connexin 43 Mimetic Peptides Reduce Swelling, Astrogliosis, and Neuronal Cell Death after Spinal Cord Injury" *Cell Commun and Adhesion*, 2008, vol. 15, p. 27-42.

Ponsaerts, R., "Intramolecular loop/tail interactions are essential for connexin 43-hemichannel activity," *FASEB Journal*, 2010, vol. 24, pp. 4378-4395.

Nagy J. I., Connexin30 in Rodent, Cat and Human Brain: Selective Expression in Gray Matter Astrocytes, Co-Localization with Connexin43 at Gap Junctions and Late Developmental Appearance, 1999, *Neuroscience*, vol. 88(2), pp. 447-468.

Rouach, N., "Astroglial Metabolic Networks Sustain Hippocampal Synaptic Transmission," 2008, *Science*, vol. 322, pp. 1551-1555.

(56) References Cited

OTHER PUBLICATIONS

Bonansco, C., "Glutamate released spontaneously from astrocytes sets the threshold for synaptic plasticity," *Eur J Neurosci.* 33, pp. 1483-1492, 2011.

Domingues, A. M., "Glia as transmitter sources and sensors in health and disease," *Neurochem International*, 57, 2010, pp. 359-366.

Samoilova, M, "Connexin 43 mimetic peptides inhibit spontaneous epileptiform activity in organotypic hippocampal slice cultures," *Experimental Neurology*, 2008, vol. 201, pp. 762-775.

Thompson, RJ, "Activation of Pannexin-1 Hemichannels Augments Aberrant Bursting in the Hippocampus," *Science*, 2008, vol. 322, pp. 1555-1559.

Orellana, JA, "Modulation of Brain Hemichannels and Gap Junction Channels by Pro-Inflammatory Agents and Their Possible Role in Neurodegeneration," 2009, *Antioxid Redox Signal*, vol. 11(2), pp. 369-399.

Kawasaki, A., "Modulation of connexin 43 in rotenone-induced model of Parkinson's disease," *Neuroscience*, vol. 160, 2009, pp. 61-68.

Behrens, CJ, "Nonspecific effects of the gap junction blocker mefloquine on fast hippocampal network oscillations in the adult rat in vitro," *Neuroscience*, 2011, vol. 192, pp. 11-19.

Araque, A., "Tripartite synapses: glia, the unacknowledged partner," 1999, *Trends Neuroscience*, vol. 22, No. 5, pp. 208-215.

Bowser, D., "ATP Excites Interneurons and Astrocytes to Increase Synaptic Inhibition in Neuronal Networks," 2004, *The Journal of Neuroscience*, vol. 24, p. 8606-8620.

Florian, C., "Astrocyte-derived Adenosine and A1 Receptor Activity Contribute to Sleep Loss-Induced Deficits in Hippocampal Synaptic Plasticity and Memory in Mice," 2011, *Journal of Neuroscience*, vol. 31, pp. 6956-6962.

Bushong, E., "Protoplasmic Astrocytes in CA1 Stratum Radiatum Occupy Separate Anatomical Domains," 2002, *The Journal of Neuroscience*, vol. 22, pp. 183-192.

Welsh, D., "Gap junctions couple astrocytes but not neurons in dissociated cultures of rat suprachiasmatic nucleus," 1996, *Brain Research*, vol. 706, pp. 30-36.

Rash, J., "Cell-Specific Expression of Connexins and Evidence of Restricted Gap Junctional Coupling between Glial Cells and Between Neurons," 2001, *J Neurosci.*, 21, 1983-2000.

Söhl, G., "Expression and Functions of Neuronal Gap Junctions," 2005, *Nature Reviews Neuroscience*, vol. 6, pp. 191-200.

Ponsaerts, R., "The contractile system as a negative regulator of the connexin 43 hemichannel," *Biol. Cell*, 2012, vol. 104, pp. 367-377.

Danesh-Meyer, HV, "Connexin43 mimetic peptide reduces vascular leak and retinal ganglion cell death following retinal ischaemia," *Brain*, 2012, vol. 135, pp. 506-520.

SEQUENCE LISTING

<160> NUMBER OF SEQ ID NOS: 116

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Tyr Gly Arg Lys Lys Arg Arg Gln Arg Arg Asp Gly Ala Asn Val
1               5                   10                  15

Asp Met His Leu Lys Gln Ile Glu Ile Lys Lys Phe Lys Tyr Gly Ile
            20                  25                  30

Glu Glu His Gly Lys
        35

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Gly Ala Asn Val Asp Met His Leu Lys Gln Ile Glu Ile Lys Lys
1               5                   10                  15

Phe Lys Tyr Gly Ile Glu Glu His Gly Lys
            20                  25

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Gly Arg Lys Lys Arg Arg Gln Arg Arg Lys Gln Ile Glu Ile
1               5                   10                  15

Lys Lys Phe Lys
            20

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Gln Ile Glu Ile Lys Lys Phe Lys
1               5

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Gly Arg Lys Lys Arg Arg Gln Arg Arg Arg Pro Arg Pro Asp
1               5                   10                  15

Asp Leu Glu

<210> SEQ ID NO 6
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 6

Arg Pro Arg Pro Asp Asp Leu Glu
1               5

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (14)..(14)
<223> OTHER INFORMATION: Arg, His, Lys, Cys, Gly, Gln, Asn, Ser, Tyr, or
      Thr

<400> SEQUENCE: 7

Tyr Gly Arg Lys Lys Arg Arg Gln Arg Arg Xaa Pro Xaa Pro Asp
1               5                   10                  15

Asp Leu Glu

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (3)..(3)
<223> OTHER INFORMATION: Arg, His, Lys, Cys, Gly, Gln, Asn, Ser, Tyr, or
      Thr

<400> SEQUENCE: 8

Xaa Pro Xaa Pro Asp Asp Leu Glu
1               5

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Phe, Ala, Leu, Met, Ile, Trp, Pro, or Val
<220> FEATURE:
<221> NAME/KEY: MOD_RES
<222> LOCATION: (15)..(15)
<223> OTHER INFORMATION: Phe, Ala, Leu, Met, Ile, Trp, Pro, or Val

<400> SEQUENCE: 9

Tyr Gly Arg Lys Lys Arg Arg Gln Arg Arg Arg Xaa Arg Xaa Asp
```

-continued

```
1               5                   10                  15
Asp Leu Glu

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe, Ala, Leu, Met, Ile, Trp, Pro, or Val
<220> FEATURE:
<221> NAME/KEY: MOD_RES
<222> LOCATION: (4)..(4)
<223> OTHER INFORMATION: Phe, Ala, Leu, Met, Ile, Trp, Pro, or Val

<400> SEQUENCE: 10

Arg Xaa Arg Xaa Asp Asp Leu Glu
1               5

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(17)
<223> OTHER INFORMATION: Asp, Glu, Cys, Gly, Gln, Asn, Ser, Tyr, or Thr
<220> FEATURE:
<221> NAME/KEY: MOD_RES
<222> LOCATION: (19)..(19)
<223> OTHER INFORMATION: Asp, Glu, Cys, Gly, Gln, Asn, Ser, Tyr, or Thr

<400> SEQUENCE: 11

Tyr Gly Arg Lys Lys Arg Arg Gln Arg Arg Arg Pro Arg Pro Xaa
1               5                   10                  15

Xaa Leu Xaa

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Asp, Glu, Cys, Gly, Gln, Asn, Ser, Tyr, or Thr
<220> FEATURE:
<221> NAME/KEY: MOD_RES
<222> LOCATION: (8)..(8)
<223> OTHER INFORMATION: Asp, Glu, Cys, Gly, Gln, Asn, Ser, Tyr, or Thr

<400> SEQUENCE: 12

Arg Pro Arg Pro Xaa Xaa Leu Xaa
1               5

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
                                    peptide
<220> FEATURE:
<221> NAME/KEY: MOD_RES
<222> LOCATION: (12)..(12)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (17)..(18)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (20)..(20)
<223> OTHER INFORMATION: Arg, His, Lys, Cys, Gly, Gln, Asn, Ser, Tyr, or
      Thr

<400> SEQUENCE: 13

Tyr Gly Arg Lys Lys Arg Arg Gln Arg Arg Xaa Gln Ile Glu Ile
1               5                   10                  15

Xaa Xaa Phe Xaa
            20

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (6)..(7)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (9)..(9)
<223> OTHER INFORMATION: Arg, His, Lys, Cys, Gly, Gln, Asn, Ser, Tyr, or
      Thr

<400> SEQUENCE: 14

Xaa Gln Ile Glu Ile Xaa Xaa Phe Xaa
1               5

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Cys, Gly, Gln, Asn, Ser, Tyr, Thr, Asp, Glu,
      Arg, His, or Lys

<400> SEQUENCE: 15

Tyr Gly Arg Lys Lys Arg Arg Gln Arg Arg Lys Xaa Ile Glu Ile
1               5                   10                  15

Lys Lys Phe Lys
            20

<210> SEQ ID NO 16
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cys, Gly, Gln, Asn, Ser, Tyr, Thr, Asp, Glu,
      Arg, His, or Lys

<400> SEQUENCE: 16

Lys Xaa Ile Glu Ile Lys Lys Phe Lys
1               5

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Phe, Ala, Leu, Met, Ile, Trp, Pro, or Val

<400> SEQUENCE: 17

Tyr Gly Arg Lys Lys Arg Arg Gln Arg Arg Lys Gln Xaa Glu Ile
1               5                   10                  15

Lys Lys Phe Lys
            20

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phe, Ala, Leu, Met, Ile, Trp, Pro, or Val

<400> SEQUENCE: 18

Lys Gln Xaa Glu Ile Lys Lys Phe Lys
1               5

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Asp, Glu, Cys, Gly, Gln, Asn, Ser, Tyr, or Thr

<400> SEQUENCE: 19

Tyr Gly Arg Lys Lys Arg Arg Gln Arg Arg Lys Gln Ile Xaa Ile
1               5                   10                  15

Lys Lys Phe Lys
            20

<210> SEQ ID NO 20
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asp, Glu, Cys, Gly, Gln, Asn, Ser, Tyr, or Thr

<400> SEQUENCE: 20

Lys Gln Ile Xaa Ile Lys Lys Phe Lys
1               5

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Gly Arg Lys Lys Arg Arg Gln Arg Arg Val Asp Cys Phe Leu
1               5                   10                  15

Ser Arg Pro Thr Glu Lys Thr
            20

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Asp Cys Phe Leu Ser Arg Pro Thr Glu Lys Thr
1               5                   10

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Phe, Ala, Leu, Met, Ile, Trp, Pro, or Val
<220> FEATURE:
<221> NAME/KEY: MOD_RES
<222> LOCATION: (15)..(16)
<223> OTHER INFORMATION: Phe, Ala, Leu, Met, Ile, Trp, Pro, or Val
<220> FEATURE:
<221> NAME/KEY: MOD_RES
<222> LOCATION: (19)..(19)
<223> OTHER INFORMATION: Phe, Ala, Leu, Met, Ile, Trp, Pro, or Val

<400> SEQUENCE: 23

Tyr Gly Arg Lys Lys Arg Arg Gln Arg Arg Xaa Cys Asp Xaa Xaa
1               5                   10                  15

Ser Arg Xaa Thr Glu Lys Thr
            20

<210> SEQ ID NO 24
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Ala, Leu, Met, Ile, Trp, Pro, or Val
<220> FEATURE:
<221> NAME/KEY: MOD_RES
<222> LOCATION: (4)..(5)
<223> OTHER INFORMATION: Phe, Ala, Leu, Met, Ile, Trp, Pro, or Val
<220> FEATURE:
<221> NAME/KEY: MOD_RES
<222> LOCATION: (8)..(8)
<223> OTHER INFORMATION: Phe, Ala, Leu, Met, Ile, Trp, Pro, or Val

<400> SEQUENCE: 24

Xaa Cys Asp Xaa Xaa Ser Arg Xaa Thr Glu Lys Thr
1               5                   10

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Asp, Glu, Cys, Gly, Gln, Asn, Ser, Tyr, or Thr
<220> FEATURE:
<221> NAME/KEY: MOD_RES
<222> LOCATION: (21)..(21)
<223> OTHER INFORMATION: Asp, Glu, Cys, Gly, Gln, Asn, Ser, Tyr, or Thr

<400> SEQUENCE: 25

Tyr Gly Arg Lys Lys Arg Arg Gln Arg Arg Val Xaa Cys Phe Leu
1               5                   10                  15

Ser Arg Pro Thr Xaa Lys Thr
            20

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp, Glu, Cys, Gly, Gln, Asn, Ser, Tyr, or Thr
<220> FEATURE:
<221> NAME/KEY: MOD_RES
<222> LOCATION: (10)..(10)
<223> OTHER INFORMATION: Asp, Glu, Cys, Gly, Gln, Asn, Ser, Tyr, or Thr

<400> SEQUENCE: 26

Val Xaa Cys Phe Leu Ser Arg Pro Thr Xaa Lys Thr
1               5                   10

<210> SEQ ID NO 27
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (14)..(14)
<223> OTHER INFORMATION: Cys, Gly, Gln, Asn, Ser, Tyr, Thr, Asp, Glu,
    Arg, His, or Lys
<220> FEATURE:
<221> NAME/KEY: MOD_RES
<222> LOCATION: (17)..(17)
<223> OTHER INFORMATION: Cys, Gly, Gln, Asn, Ser, Tyr, Thr, Asp, Glu,
    Arg, His, or Lys
<220> FEATURE:
<221> NAME/KEY: MOD_RES
<222> LOCATION: (20)..(20)
<223> OTHER INFORMATION: Cys, Gly, Gln, Asn, Ser, Tyr, Thr, Asp, Glu,
    Arg, His, or Lys
<220> FEATURE:
<221> NAME/KEY: MOD_RES
<222> LOCATION: (23)..(23)
<223> OTHER INFORMATION: Cys, Gly, Gln, Asn, Ser, Tyr, Thr, Asp, Glu,
    Arg, His, or Lys

<400> SEQUENCE: 27

Tyr Gly Arg Lys Lys Arg Arg Gln Arg Arg Arg Val Asp Xaa Phe Leu
1               5                   10                  15

Xaa Arg Pro Xaa Glu Lys Xaa
            20

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (3)..(3)
<223> OTHER INFORMATION: Cys, Gly, Gln, Asn, Ser, Tyr, Thr, Asp, Glu,
    Arg, His, or Lys
<220> FEATURE:
<221> NAME/KEY: MOD_RES
<222> LOCATION: (6)..(6)
<223> OTHER INFORMATION: Cys, Gly, Gln, Asn, Ser, Tyr, Thr, Asp, Glu,
    Arg, His, or Lys
<220> FEATURE:
<221> NAME/KEY: MOD_RES
<222> LOCATION: (9)..(9)
<223> OTHER INFORMATION: Cys, Gly, Gln, Asn, Ser, Tyr, Thr, Asp, Glu,
    Arg, His, or Lys
<220> FEATURE:
<221> NAME/KEY: MOD_RES
<222> LOCATION: (12)..(12)
<223> OTHER INFORMATION: Cys, Gly, Gln, Asn, Ser, Tyr, Thr, Asp, Glu,
    Arg, His, or Lys

<400> SEQUENCE: 28

Val Asp Xaa Phe Leu Xaa Arg Pro Xaa Glu Lys Xaa
1               5                   10

<210> SEQ ID NO 29
<211> LENGTH: 23
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (18)..(18)
<223> OTHER INFORMATION: Arg, His, Lys, Cys, Gly, Gln, Asn, Ser, Tyr, or
    Thr
<220> FEATURE:
<221> NAME/KEY: MOD_RES
<222> LOCATION: (22)..(22)
<223> OTHER INFORMATION: Arg, His, Lys, Cys, Gly, Gln, Asn, Ser, Tyr, or
    Thr

```
<400> SEQUENCE: 29

Tyr Gly Arg Lys Lys Arg Arg Gln Arg Arg Val Asp Cys Phe Leu
1               5                   10                  15

Ser Xaa Pro Thr Arg Xaa Thr
            20

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (11)..(11)
<223> OTHER INFORMATION: Arg, His, Lys, Cys, Gly, Gln, Asn, Ser, Tyr, or
      Thr

<400> SEQUENCE: 30

Val Asp Cys Phe Leu Ser Xaa Pro Thr Arg Xaa Thr
1               5                   10

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Gly Arg Lys Lys Arg Arg Gln Arg Arg Trp Arg Gln Ala Ala
1               5                   10                  15

Phe Val Asp Ser Tyr
            20

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Arg Gln Ala Ala Phe Val Asp Ser Tyr
1               5                   10

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Phe, Ala, Leu, Met, Ile, Trp, Pro, or Val
<220> FEATURE:
<221> NAME/KEY: MOD_RES
<222> LOCATION: (15)..(18)
```

```
<223> OTHER INFORMATION: Phe, Ala, Leu, Met, Ile, Trp, Pro, or Val

<400> SEQUENCE: 33

Tyr Gly Arg Lys Lys Arg Arg Gln Arg Arg Xaa Arg Gln Xaa Xaa
1               5                   10                  15

Xaa Xaa Asp Ser Tyr
            20

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Ala, Leu, Met, Ile, Trp, Pro, or Val
<220> FEATURE:
<221> NAME/KEY: MOD_RES
<222> LOCATION: (4)..(7)
<223> OTHER INFORMATION: Phe, Ala, Leu, Met, Ile, Trp, Pro, or Val

<400> SEQUENCE: 34

Xaa Arg Gln Xaa Xaa Xaa Xaa Asp Ser Tyr
1               5                   10

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Arg, His, Lys, Cys, Gly, Gln, Asn, Ser, Tyr, or
      Thr

<400> SEQUENCE: 35

Tyr Gly Arg Lys Lys Arg Arg Gln Arg Arg Trp Xaa Gln Ala Ala
1               5                   10                  15

Phe Val Asp Ser Tyr
            20

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg, His, Lys, Cys, Gly, Gln, Asn, Ser, Tyr, or
      Thr

<400> SEQUENCE: 36

Trp Xaa Gln Ala Ala Phe Val Asp Ser Tyr
1               5                   10

<210> SEQ ID NO 37
<211> LENGTH: 21
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (20)..(21)
<223> OTHER INFORMATION: Cys, Gly, Gln, Asn, Ser, Tyr, Thr, Asp, Glu,
      Arg, His, or Lys

<400> SEQUENCE: 37

Tyr Gly Arg Lys Lys Arg Arg Gln Arg Arg Trp Arg Xaa Ala Ala
1               5                   10                  15

Phe Val Asp Xaa Xaa
            20

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (9)..(10)
<223> OTHER INFORMATION: Cys, Gly, Gln, Asn, Ser, Tyr, Thr, Asp, Glu,
      Arg, His, or Lys

<400> SEQUENCE: 38

Trp Arg Xaa Ala Ala Phe Val Asp Xaa Xaa
1               5                   10

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Asp, Glu, Cys, Gly, Gln, Asn, Ser, or Tyr

<400> SEQUENCE: 39

Tyr Gly Arg Lys Lys Arg Arg Gln Arg Arg Trp Arg Gln Ala Ala
1               5                   10                  15

Phe Val Xaa Ser Tyr
            20

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asp, Glu, Cys, Gly, Gln, Asn, Ser, or Tyr
```

```
<400> SEQUENCE: 40

Trp Arg Gln Ala Ala Phe Val Xaa Ser Tyr
1               5                   10

<210> SEQ ID NO 41
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Gly Arg Lys Lys Arg Arg Gln Arg Arg Ser Ser Phe Ser Trp
1               5                   10                  15

Arg Gln Ala Ala Phe Val Asp Ser
            20

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Ser Phe Ser Trp Arg Gln Ala Ala Phe Val Asp Ser
1               5                   10

<210> SEQ ID NO 43
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(13)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (15)..(15)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (18)..(18)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (24)..(24)
<223> OTHER INFORMATION: Cys, Gly, Gln, Asn, Ser, Tyr, Thr, Asp, Glu,
      Arg, His, or Lys

<400> SEQUENCE: 43

Tyr Gly Arg Lys Lys Arg Arg Gln Arg Arg Xaa Xaa Phe Xaa Trp
1               5                   10                  15

Arg Xaa Ala Ala Phe Val Asp Xaa
            20

<210> SEQ ID NO 44
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (4)..(4)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (7)..(7)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (13)..(13)
<223> OTHER INFORMATION: Cys, Gly, Gln, Asn, Ser, Tyr, Thr, Asp, Glu,
      Arg, His, or Lys

<400> SEQUENCE: 44

Xaa Xaa Phe Xaa Trp Arg Xaa Ala Ala Phe Val Asp Xaa
1               5                   10

<210> SEQ ID NO 45
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Phe, Ala, Leu, Met, Ile, Trp, Pro, or Val
<220> FEATURE:
<221> NAME/KEY: MOD_RES
<222> LOCATION: (16)..(16)
<223> OTHER INFORMATION: Phe, Ala, Leu, Met, Ile, Trp, Pro, or Val
<220> FEATURE:
<221> NAME/KEY: MOD_RES
<222> LOCATION: (19)..(22)
<223> OTHER INFORMATION: Phe, Ala, Leu, Met, Ile, Trp, Pro, or Val

<400> SEQUENCE: 45

Tyr Gly Arg Lys Lys Arg Arg Gln Arg Arg Ser Ser Xaa Ser Xaa
1               5                   10                  15

Arg Gln Xaa Xaa Xaa Xaa Asp Ser
            20

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phe, Ala, Leu, Met, Ile, Trp, Pro, or Val
<220> FEATURE:
<221> NAME/KEY: MOD_RES
<222> LOCATION: (5)..(5)
<223> OTHER INFORMATION: Phe, Ala, Leu, Met, Ile, Trp, Pro, or Val
<220> FEATURE:
<221> NAME/KEY: MOD_RES
<222> LOCATION: (8)..(11)
<223> OTHER INFORMATION: Phe, Ala, Leu, Met, Ile, Trp, Pro, or Val

<400> SEQUENCE: 46
```

```
Ser Ser Xaa Ser Xaa Arg Gln Xaa Xaa Xaa Xaa Asp Ser
1               5                   10
```

<210> SEQ ID NO 47
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Arg, His, Lys, Cys, Gly, Gln, Asn, Ser, Tyr, or
      Thr

<400> SEQUENCE: 47

```
Tyr Gly Arg Lys Lys Arg Arg Gln Arg Arg Ser Ser Phe Ser Trp
1               5                   10                  15

Xaa Gln Ala Ala Phe Val Asp Ser
            20
```

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Arg, His, Lys, Cys, Gly, Gln, Asn, Ser, Tyr, or
      Thr

<400> SEQUENCE: 48

```
Ser Ser Phe Ser Trp Xaa Gln Ala Ala Phe Val Asp Ser
1               5                   10
```

<210> SEQ ID NO 49
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Asp, Glu, Cys, Gly, Gln, Asn, Ser, or Tyr

<400> SEQUENCE: 49

```
Tyr Gly Arg Lys Lys Arg Arg Gln Arg Arg Ser Ser Phe Ser Trp
1               5                   10                  15

Arg Gln Ala Ala Phe Val Xaa Ser
            20
```

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Asp, Glu, Cys, Gly, Gln, Asn, Ser, or Tyr

```
<400> SEQUENCE: 50

Ser Ser Phe Ser Trp Arg Gln Ala Ala Phe Val Xaa Ser
1               5                   10

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Gly Arg Lys Lys Arg Arg Gln Arg Arg Arg Asp Leu Asp Leu
1               5                   10                  15

Arg Asp Gly Pro
            20

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Leu Asp Leu Arg Asp Gly Pro
1               5

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Asp, Glu, Cys, Gly, Gln, Asn, Ser, Tyr, Arg,
      His, or Lys
<220> FEATURE:
<221> NAME/KEY: MOD_RES
<222> LOCATION: (14)..(14)
<223> OTHER INFORMATION: Asp, Glu, Cys, Gly, Gln, Asn, Ser, Tyr, Arg,
      His, or Lys
<220> FEATURE:
<221> NAME/KEY: MOD_RES
<222> LOCATION: (17)..(17)
<223> OTHER INFORMATION: Asp, Glu, Cys, Gly, Gln, Asn, Ser, Tyr, Arg,
      His, or Lys

<400> SEQUENCE: 53

Tyr Gly Arg Lys Lys Arg Arg Gln Arg Arg Arg Xaa Leu Xaa Leu Arg
1               5                   10                  15

Xaa Gly Pro

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Glu, Cys, Gly, Gln, Asn, Ser, Tyr, Arg,
```

```
        His, or Lys
<220> FEATURE:
<221> NAME/KEY: MOD_RES
<222> LOCATION: (3)..(3)
<223> OTHER INFORMATION: Asp, Glu, Cys, Gly, Gln, Asn, Ser, Tyr, Arg,
      His, or Lys
<220> FEATURE:
<221> NAME/KEY: MOD_RES
<222> LOCATION: (6)..(6)
<223> OTHER INFORMATION: Asp, Glu, Cys, Gly, Gln, Asn, Ser, Tyr, Arg,
      His, or Lys

<400> SEQUENCE: 54

Xaa Leu Xaa Leu Arg Xaa Gly Pro
1               5

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Phe, Ala, Leu, Met, Ile, Trp, Pro, or Val
<220> FEATURE:
<221> NAME/KEY: MOD_RES
<222> LOCATION: (15)..(15)
<223> OTHER INFORMATION: Phe, Ala, Leu, Met, Ile, Trp, Pro, or Val
<220> FEATURE:
<221> NAME/KEY: MOD_RES
<222> LOCATION: (19)..(19)
<223> OTHER INFORMATION: Phe, Ala, Leu, Met, Ile, Trp, Pro, or Val

<400> SEQUENCE: 55

Tyr Gly Arg Lys Lys Arg Arg Gln Arg Arg Asp Xaa Asp Xaa Arg
1               5                   10                  15

Asp Gly Xaa

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe, Ala, Leu, Met, Ile, Trp, Pro, or Val
<220> FEATURE:
<221> NAME/KEY: MOD_RES
<222> LOCATION: (4)..(4)
<223> OTHER INFORMATION: Phe, Ala, Leu, Met, Ile, Trp, Pro, or Val
<220> FEATURE:
<221> NAME/KEY: MOD_RES
<222> LOCATION: (8)..(8)
<223> OTHER INFORMATION: Phe, Ala, Leu, Met, Ile, Trp, Pro, or Val

<400> SEQUENCE: 56

Asp Xaa Asp Xaa Arg Asp Gly Xaa
1               5

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (16)..(16)
<223> OTHER INFORMATION: Arg, His, Lys, Cys, Gly, Gln, Asn, Ser, Tyr, or
      Thr

<400> SEQUENCE: 57

Tyr Gly Arg Lys Lys Arg Arg Gln Arg Arg Arg Asp Leu Asp Leu Xaa
1               5                   10                  15

Asp Gly Pro

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Arg, His, Lys, Cys, Gly, Gln, Asn, Ser, Tyr, or
      Thr

<400> SEQUENCE: 58

Asp Leu Asp Leu Xaa Asp Gly Pro
1               5

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Cys, Gly, Gln, Asn, Ser, Tyr, Thr, Asp, Glu,
      Arg, His, or Lys

<400> SEQUENCE: 59

Tyr Gly Arg Lys Lys Arg Arg Gln Arg Arg Arg Asp Leu Asp Leu Arg
1               5                   10                  15

Asp Xaa Pro

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Cys, Gly, Gln, Asn, Ser, Tyr, Thr, Asp, Glu,
      Arg, His, or Lys

<400> SEQUENCE: 60

Asp Leu Asp Leu Arg Asp Xaa Pro
1               5

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 61

Tyr Gly Arg Lys Lys Arg Arg Gln Arg Arg Pro Met Ser Leu Gln
1               5                   10                  15

Thr Lys Gly Glu
            20

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Met Ser Leu Gln Thr Lys Gly Glu
1               5

<210> SEQ ID NO 63
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(13)
<223> OTHER INFORMATION: Phe, Ala, Leu, Met, Ile, Trp, Pro, or Val
<220> FEATURE:
<221> NAME/KEY: MOD_RES
<222> LOCATION: (15)..(15)
<223> OTHER INFORMATION: Phe, Ala, Leu, Met, Ile, Trp, Pro, or Val

<400> SEQUENCE: 63

Tyr Gly Arg Lys Lys Arg Arg Gln Arg Arg Xaa Xaa Ser Xaa Gln
1               5                   10                  15

Thr Lys Gly Glu
            20

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Phe, Ala, Leu, Met, Ile, Trp, Pro, or Val
<220> FEATURE:
<221> NAME/KEY: MOD_RES
<222> LOCATION: (4)..(4)
<223> OTHER INFORMATION: Phe, Ala, Leu, Met, Ile, Trp, Pro, or Val

<400> SEQUENCE: 64

Xaa Xaa Ser Xaa Gln Thr Lys Gly Glu
1               5

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (14)..(14)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (16)..(17)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (19)..(19)
<223> OTHER INFORMATION: Cys, Gly, Gln, Asn, Ser, Tyr, Thr, Asp, Glu,
      Arg, His, or Lys

<400> SEQUENCE: 65

Tyr Gly Arg Lys Lys Arg Arg Gln Arg Arg Pro Met Xaa Leu Xaa
1               5                   10                  15

Xaa Lys Xaa Glu
            20

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (5)..(6)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (8)..(8)
<223> OTHER INFORMATION: Cys, Gly, Gln, Asn, Ser, Tyr, Thr, Asp, Glu,
      Arg, His, or Lys

<400> SEQUENCE: 66

Pro Met Xaa Leu Xaa Xaa Lys Xaa Glu
1               5

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Arg, His, Lys, Cys, Gly, Gln, Asn, Ser, Tyr, or
      Thr

<400> SEQUENCE: 67

Tyr Gly Arg Lys Lys Arg Arg Gln Arg Arg Pro Met Ser Leu Gln
1               5                   10                  15

Thr Xaa Gly Glu
            20

<210> SEQ ID NO 68
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Arg, His, Lys, Cys, Gly, Gln, Asn, Ser, Tyr, or
      Thr

<400> SEQUENCE: 68

Pro Met Ser Leu Gln Thr Xaa Gly Glu
1               5

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Asp, Glu, Cys, Gly, Gln, Asn, Ser, Tyr, or Thr

<400> SEQUENCE: 69

Tyr Gly Arg Lys Lys Arg Arg Gln Arg Arg Pro Met Ser Leu Gln
1               5                   10                  15

Thr Lys Gly Xaa
            20

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Asp, Glu, Cys, Gly, Gln, Asn, Ser, Tyr, or Thr

<400> SEQUENCE: 70

Pro Met Ser Leu Gln Thr Lys Gly Xaa
1               5

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Tyr Gly Arg Lys Lys Arg Arg Gln Arg Arg Asp Ala Pro Ala Leu
1               5                   10                  15

Tyr Ser Asn Leu Ser Lys Lys Arg Gly
            20                  25

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 72

Asp Ala Pro Ala Leu Tyr Ser Asn Leu Ser Lys Lys Arg Gly
1               5                   10

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Asp, Glu, Cys, Gly, Gln, Asn, Ser, or Tyr

<400> SEQUENCE: 73

Tyr Gly Arg Lys Lys Arg Arg Gln Arg Arg Arg Xaa Ala Pro Ala Leu
1               5                   10                  15

Tyr Ser Asn Leu Ser Lys Lys Arg Gly
            20                  25

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Glu, Cys, Gly, Gln, Asn, Ser, or Tyr

<400> SEQUENCE: 74

Xaa Ala Pro Ala Leu Tyr Ser Asn Leu Ser Lys Lys Arg Gly
1               5                   10

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(16)
<223> OTHER INFORMATION: Phe, Ala, Leu, Met, Ile, Trp, Pro, or Val
<220> FEATURE:
<221> NAME/KEY: MOD_RES
<222> LOCATION: (20)..(20)
<223> OTHER INFORMATION: Phe, Ala, Leu, Met, Ile, Trp, Pro, or Val

<400> SEQUENCE: 75

Tyr Gly Arg Lys Lys Arg Arg Gln Arg Arg Arg Asp Xaa Xaa Xaa Xaa
1               5                   10                  15

Tyr Ser Asn Xaa Ser Lys Lys Arg Gly
            20                  25

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (2)..(5)
<223> OTHER INFORMATION: Phe, Ala, Leu, Met, Ile, Trp, Pro, or Val
<220> FEATURE:
<221> NAME/KEY: MOD_RES
<222> LOCATION: (9)..(9)
<223> OTHER INFORMATION: Phe, Ala, Leu, Met, Ile, Trp, Pro, or Val

<400> SEQUENCE: 76

Asp Xaa Xaa Xaa Xaa Tyr Ser Asn Xaa Ser Lys Lys Arg Gly
1               5                   10

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(19)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (21)..(21)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (25)..(25)
<223> OTHER INFORMATION: Cys, Gly, Gln, Asn, Ser, Tyr, Thr, Asp, Glu,
      Arg, His, or Lys

<400> SEQUENCE: 77

Tyr Gly Arg Lys Lys Arg Arg Gln Arg Arg Asp Ala Pro Ala Leu
1               5                   10                  15

Xaa Xaa Xaa Leu Xaa Lys Lys Arg Xaa
            20                  25

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(8)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (10)..(10)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (14)..(14)
<223> OTHER INFORMATION: Cys, Gly, Gln, Asn, Ser, Tyr, Thr, Asp, Glu,
      Arg, His, or Lys

<400> SEQUENCE: 78

Asp Ala Pro Ala Leu Xaa Xaa Xaa Leu Xaa Lys Lys Arg Xaa
1               5                   10

<210> SEQ ID NO 79
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(24)
<223> OTHER INFORMATION: Arg, His, Lys, Cys, Gly, Gln, Asn, Ser, Tyr, or
      Thr

<400> SEQUENCE: 79

Tyr Gly Arg Lys Lys Arg Arg Gln Arg Arg Asp Ala Pro Ala Leu
1               5                   10                  15

Tyr Ser Asn Leu Ser Xaa Xaa Xaa Gly
            20                  25

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(13)
<223> OTHER INFORMATION: Arg, His, Lys, Cys, Gly, Gln, Asn, Ser, Tyr, or
      Thr

<400> SEQUENCE: 80

Asp Ala Pro Ala Leu Tyr Ser Asn Leu Ser Xaa Xaa Xaa Gly
1               5                   10

<210> SEQ ID NO 81
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Tyr Gly Arg Lys Lys Arg Arg Gln Arg Arg Thr Cys Pro Pro Tyr
1               5                   10                  15

Val Ile Ser Lys Gly His Pro Gln
            20

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Cys Pro Pro Tyr Val Ile Ser Lys Gly His Pro Gln
1               5                   10

<210> SEQ ID NO 83
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(13)
<223> OTHER INFORMATION: Cys, Gly, Gln, Asn, Ser, Tyr, Thr, Asp, Glu,
```

Arg, His, or Lys
<220> FEATURE:
<221> NAME/KEY: MOD_RES
<222> LOCATION: (16)..(16)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (20)..(20)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (23)..(23)
<223> OTHER INFORMATION: Cys, Gly, Gln, Asn, Ser, Tyr, Thr, Asp, Glu,
      Arg, His, or Lys

<400> SEQUENCE: 83

Tyr Gly Arg Lys Lys Arg Arg Gln Arg Arg Xaa Xaa Pro Pro Xaa
1               5                   10                  15

Val Ile Lys Xaa His Pro Xaa
            20

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (5)..(5)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (9)..(9)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (12)..(12)
<223> OTHER INFORMATION: Cys, Gly, Gln, Asn, Ser, Tyr, Thr, Asp, Glu,
      Arg, His, or Lys

<400> SEQUENCE: 84

Xaa Xaa Pro Pro Xaa Val Ile Lys Xaa His Pro Xaa
1               5                   10

<210> SEQ ID NO 85
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(15)
<223> OTHER INFORMATION: Phe, Ala, Leu, Met, Ile, Trp, Pro, or Val
<220> FEATURE:
<221> NAME/KEY: MOD_RES
<222> LOCATION: (17)..(18)
<223> OTHER INFORMATION: Phe, Ala, Leu, Met, Ile, Trp, Pro, or Val
<220> FEATURE:
<221> NAME/KEY: MOD_RES
<222> LOCATION: (23)..(23)
<223> OTHER INFORMATION: Phe, Ala, Leu, Met, Ile, Trp, Pro, or Val

<400> SEQUENCE: 85

Tyr Gly Arg Lys Lys Arg Arg Gln Arg Arg Thr Cys Xaa Xaa Tyr
1               5                   10                  15

Xaa Xaa Ser Lys Gly His Xaa Gln
            20

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Phe, Ala, Leu, Met, Ile, Trp, Pro, or Val
<220> FEATURE:
<221> NAME/KEY: MOD_RES
<222> LOCATION: (6)..(7)
<223> OTHER INFORMATION: Phe, Ala, Leu, Met, Ile, Trp, Pro, or Val
<220> FEATURE:
<221> NAME/KEY: MOD_RES
<222> LOCATION: (12)..(12)
<223> OTHER INFORMATION: Phe, Ala, Leu, Met, Ile, Trp, Pro, or Val

<400> SEQUENCE: 86

Thr Cys Xaa Xaa Tyr Xaa Xaa Ser Lys Gly His Xaa Gln
1               5                   10

<210> SEQ ID NO 87
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (22)..(22)
<223> OTHER INFORMATION: Arg, His, Lys, Cys, Gly, Gln, Asn, Ser, Tyr, or
      Thr

<400> SEQUENCE: 87

Tyr Gly Arg Lys Lys Arg Arg Gln Arg Arg Thr Cys Pro Pro Tyr
1               5                   10                  15

Val Ile Ser Xaa Gly Xaa Pro Gln
            20

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (11)..(11)
<223> OTHER INFORMATION: Arg, His, Lys, Cys, Gly, Gln, Asn, Ser, Tyr, or Thr

<400> SEQUENCE: 88

Thr Cys Pro Pro Tyr Val Ile Ser Xaa Gly Xaa Pro Gln
1               5                  10

<210> SEQ ID NO 89
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Tyr Gly Arg Lys Lys Arg Arg Gln Arg Arg Cys Tyr Asp His Phe
1               5                  10                  15

Phe Pro Val Ser His Ile Arg
            20

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Cys Tyr Asp His Phe Phe Pro Val Ser His Ile Arg
1               5                  10

<210> SEQ ID NO 91
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(13)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (20)..(20)
<223> OTHER INFORMATION: Cys, Gly, Gln, Asn, Ser, Tyr, Thr, Asp, Glu,
      Arg, His, or Lys

<400> SEQUENCE: 91

Tyr Gly Arg Lys Lys Arg Arg Gln Arg Arg Xaa Xaa Asp His Phe
1               5                  10                  15

Phe Pro Val Xaa His Ile Arg
            20

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Cys, Gly, Gln, Asn, Ser, Tyr, Thr, Asp, Glu,
      Arg, His, or Lys
<220> FEATURE:

```
<221> NAME/KEY: MOD_RES
<222> LOCATION: (9)..(9)
<223> OTHER INFORMATION: Cys, Gly, Gln, Asn, Ser, Tyr, Thr, Asp, Glu,
      Arg, His, or Lys

<400> SEQUENCE: 92

Xaa Xaa Asp His Phe Phe Pro Val Xaa His Ile Arg
1               5                   10

<210> SEQ ID NO 93
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Asp, Glu, Cys, Gly, Gln, Asn, Ser, Tyr, or Thr

<400> SEQUENCE: 93

Tyr Gly Arg Lys Lys Arg Arg Gln Arg Arg Cys Tyr Xaa His Phe
1               5                   10                  15

Phe Pro Val Ser His Ile Arg
            20

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Glu, Cys, Gly, Gln, Asn, Ser, Tyr, or Thr

<400> SEQUENCE: 94

Cys Tyr Xaa His Phe Phe Pro Val Ser His Ile Arg
1               5                   10

<210> SEQ ID NO 95
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (21)..(21)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (23)..(23)
<223> OTHER INFORMATION: Arg, His, Lys, Cys, Gly, Gln, Asn, Ser, Tyr, or
      Thr

<400> SEQUENCE: 95

Tyr Gly Arg Lys Lys Arg Arg Gln Arg Arg Cys Tyr Asp Xaa Phe
1               5                   10                  15

Phe Pro Val Ser Xaa Ile Xaa
```

```
<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (10)..(10)
<223> OTHER INFORMATION: Arg, His, Lys, Cys, Gly, Gln, Asn, Ser, Tyr, or
      Thr
<220> FEATURE:
<221> NAME/KEY: MOD_RES
<222> LOCATION: (12)..(12)
<223> OTHER INFORMATION: Arg, His, Lys, Cys, Gly, Gln, Asn, Ser, Tyr, or
      Thr

<400> SEQUENCE: 96

Cys Tyr Asp Xaa Phe Phe Pro Val Ser Xaa Ile Xaa
1               5                   10

<210> SEQ ID NO 97
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(19)
<223> OTHER INFORMATION: Phe, Ala, Leu, Met, Ile, Trp, Pro, or Val
<220> FEATURE:
<221> NAME/KEY: MOD_RES
<222> LOCATION: (22)..(22)
<223> OTHER INFORMATION: Phe, Ala, Leu, Met, Ile, Trp, Pro, or Val

<400> SEQUENCE: 97

Tyr Gly Arg Lys Lys Arg Arg Gln Arg Arg Cys Tyr Asp His Xaa
1               5                   10                  15

Xaa Xaa Xaa Ser His Xaa Arg
            20

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(8)
<223> OTHER INFORMATION: Phe, Ala, Leu, Met, Ile, Trp, Pro, or Val
<220> FEATURE:
<221> NAME/KEY: MOD_RES
<222> LOCATION: (11)..(11)
<223> OTHER INFORMATION: Phe, Ala, Leu, Met, Ile, Trp, Pro, or Val

<400> SEQUENCE: 98

Cys Tyr Asp His Xaa Xaa Xaa Xaa Ser His Xaa Arg
1               5                   10
```

```
<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(9)
<223> OTHER INFORMATION: Any amino acid

<400> SEQUENCE: 99

Xaa Pro Xaa Pro Asp Asp Xaa Xaa Xaa
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Asp, Glu, Ser, Thr, Cys, Asn, Gln

<400> SEQUENCE: 100

Arg Pro Arg Pro Xaa Xaa Leu Glu
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe, Ala, Leu, Met, Ile, Trp, Pro, or Val
<220> FEATURE:
<221> NAME/KEY: MOD_RES
<222> LOCATION: (4)..(4)
<223> OTHER INFORMATION: Phe, Ala, Leu, Met, Ile, Trp, Pro, or Val

<400> SEQUENCE: 101

Arg Xaa Arg Xaa Asp Asp Leu Glu
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
```

```
<222> LOCATION: (3)..(3)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 102

Xaa Pro Xaa Pro Asp Asp Xaa Xaa
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pro, His, Phe, Trp, or Tyr
<220> FEATURE:
<221> NAME/KEY: MOD_RES
<222> LOCATION: (4)..(4)
<223> OTHER INFORMATION: Pro, His, Phe, Trp, or Tyr
<220> FEATURE:
<221> NAME/KEY: MOD_RES
<222> LOCATION: (7)..(8)
<223> OTHER INFORMATION: Pro, His, Phe, Trp, or Tyr

<400> SEQUENCE: 103

Arg Xaa Arg Xaa Asp Asp Xaa Xaa
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Asp, Glu, Ser, Thr, Cys, Asn, or Gln

<400> SEQUENCE: 104

Arg Pro Arg Pro Xaa Xaa Leu Glu
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 105
```

Xaa Pro Xaa Pro Asp Asp Xaa Xaa
1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pro, His, Phe, Trp, or Tyr
<220> FEATURE:
<221> NAME/KEY: MOD_RES
<222> LOCATION: (7)..(8)
<223> OTHER INFORMATION: Pro, His, Phe, Trp, or Tyr

<400> SEQUENCE: 106

Arg Xaa Arg Pro Asp Asp Xaa Xaa
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asp, Glu, Ser, Thr, Cys, Asn, or Gln
<220> FEATURE:
<221> NAME/KEY: MOD_RES
<222> LOCATION: (7)..(8)
<223> OTHER INFORMATION: Asp, Glu, Ser, Thr, Cys, Asn, or Gln

<400> SEQUENCE: 107

Arg Pro Arg Xaa Asp Asp Xaa Xaa
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 108

Xaa Xaa Pro Xaa Asp Asp Xaa Xaa
1               5

<210> SEQ ID NO 109
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid

<400> SEQUENCE: 109

Lys Xaa Xaa Xaa Ile Lys Lys Phe Lys
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid

<400> SEQUENCE: 110

Xaa Gln Ile Xaa Ile Xaa Xaa Phe Lys
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(9)
<223> OTHER INFORMATION: Any amino acid

<400> SEQUENCE: 111

Lys Gln Ile Glu Xaa Lys Lys Xaa Xaa
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(6)
<223> OTHER INFORMATION: Any amino acid
<220> FEATURE:
<221> NAME/KEY: MOD_RES
<222> LOCATION: (8)..(9)
```

```
<223> OTHER INFORMATION: Any amino acid

<400> SEQUENCE: 112

Xaa Xaa Ile Xaa Xaa Xaa Lys Xaa Xaa
 1               5

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (11)..(13)
<223> OTHER INFORMATION: Any amino acid

<400> SEQUENCE: 113

Xaa Asp Xaa Xaa Leu Ser Arg Pro Thr Arg Xaa Xaa Xaa
 1               5                  10

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 114

Asp Xaa Asp Xaa Xaa Asp Xaa Xaa
 1               5

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (4)..(4)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
```

```
<222> LOCATION: (6)..(7)
<223> OTHER INFORMATION: Cys, Gly, Gln, Asn, Ser, Tyr, Thr, Asp, Glu,
      Arg, His, or Lys
<220> FEATURE:
<221> NAME/KEY: MOD_RES
<222> LOCATION: (13)..(13)
<223> OTHER INFORMATION: Cys, Gly, Gln, Asn, Ser, Tyr, Thr, Asp, Glu,
      Arg, His, or Lys

<400> SEQUENCE: 115

Xaa Xaa Phe Xaa Trp Xaa Xaa Ala Ala Phe Val Asp Xaa
1               5                   10

<210> SEQ ID NO 116
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Lys Lys Phe Lys
1
```

USE OF COMPOUNDS THAT SELECTIVELY MODULATE ASTROCYTIC RELEASE OF SUBSTANCES THROUGH HEMICHANNELS OF CONNEXINS AND PANNEXINS, WITHOUT INFLUENCING GAP JUNCTIONS, FOR THE TREATMENT OF PSYCHIATRIC DISORDERS

SEQUENCE LISTING

The instant application contains a Sequence Listing which has been submitted electronically in ASCII format and is hereby incorporated by reference in its entirety. Said ASCII copy, created on Dec. 30, 2015, is named SAK-14-2412_SL.txt and is 51,994 bytes in size.

TECHNICAL FIELD

This disclosure relates to psychiatry, particularly to treatment of psychiatric disorders using astrocyte connexin and pannexin hemichannels as pharmacological targets.

BACKGROUND

In spite of the popular belief that neurons are the main constituents of the human brain, most of brain cells are not actually neurons, but star-shaped glial cells known as astrocytes. Their role up—until recently—was believed to be neuron sustenance, neurotransmitter recycling and maintenance of the blood brain barrier. In recent years, it has become increasingly evident that their role in brain function may be more protagonistic than previously thought.

Hundreds of astrocytes can be connected simultaneously to allow collective metabolic and electric coupling as well as calcium-wave signalling. Such inter-astrocyte communication is attained by sharing cytoplasmic content through special channels called gap junctions channels, each formed by two hemichannels contributed by each adjacent cell. Each hemichannel is composed of six protein subunits termed connexins (Cxs), with connexin 43 (Cx43) and connexin 30 (Cx30) as the main connexin constituents of astrocytes and Cx43 being the most abundantly expressed. Interestingly, hemichannels do not always form gap junction channels and may also be found in non-contacting membranes where they allow intracellular-extracellular communication. Although such "functional hemichannels" show low open probability in cultured cells under resting conditions, when opened, they may allow the release of neuroactive substances such as ATP[1] and glutamate[1,2] and several others, now known as "gliotransmitters". Astrocytes also express another type of hemichannels known as pannexins, particularly pannexin 1[1,3]. In vivo, the location of Cx43, Cx30 and pannexin 1 hemichannels at the unopposed surface of astrocytes leaves them in a unique position to mediate the release of gliotransmitters into the chemical neuronal synapse.

Recently, an increasing number of studies have supported the notion that synapses between two neurons may require signals released from an astrocyte to be fully functional[4]. Further evidence from in vitro studies indicates that release of gliotransmitters from astrocytes is required to attain synaptic plasticity[5] including release of D-serine[6,7], glutamate[2,8] and ATP[1,9]. Moreover, glutamate release from astrocytes may also affect neurotransmitter release at synapses[10], suggesting that presynaptic efficacy and postsynaptic responses are both modulated by astrocytic release of gliotransmitters. The mechanism by which neuroactive gliotransmitters are released remains unknown, although vesicles, P2X$_7$ channels, transporters[10] and Cx hemichannels[1,9] have been proposed. However, there is to date no in vivo evidence for the release of gliotransmitters from astrocytes and no studies so far have shown that Cx43, Cx30 and Panx1 hemichannels are involved in gliotransmitter release in vivo. The lack of such evidence can be at least in part attributed to a lack of tools that affect gliotransmitter release from astrocytes without affecting neuronal synaptic release or inter astrocyte communication. These types of compounds could be used for modulating release of substances from astrocytes to synaptic space, without affecting inter astrocyte communication, thus turning astrocytes into pharmacological targets for treating psychiatric disorders.

Samoilova et al., 2008[12] studied the use of connexin mimetic peptides corresponding to aminoacidic sequences and the general gap junctional blocker, carbenoxolone in generation of epileptiform activity. They postulate that gap junctions can modulate brain activity using rat organotypic hippocampal slice cultures. Samoilova et al., 2008 describes the use of compounds for blocking connexin gap junctions and not connexin hemichannels as the present invention and also does not mention connexin hemichannels from astrocytes as pharmacological target, nor psychiatric disorders for their use.

Danesh-Meyer et al., 2012[13] studied the use of connexin 43 mimetic peptides to investigate neuronal rescue following retinal ischaemia-reperfusion and vascular permeability by transiently blocking connexin 43 activity. They postulate blocking of connexin 43 gap junctions as pharmacological target for the treatment of central nervous system ischemia. Danesh-Meyer et al., 2012 describes the use of compounds for blocking connexin gap junctions from astrocytes but does not mention connexin hemichannels from the cells for the treatment of psychiatric disorders.

Thomson et al., 2008[14] studied the use of specific inhibitors of pannexin 1 from pyramidal neurons in epileptiform seizure activity. They postulate that pannexin 1 hemichannel contributes to epileptiform activity, turning pannexin 1 as a pharmacological target for treatment of epilepsy. Thomson et al., 2008 does not mention pannexins from astrocytes, nor Cx43 or Cx30 hemichannels, only pannexin 1 from pyramidal neurons, thus, they do not postulate astrocytes as pharmacological targets for psychiatric disorders.

Orellana et al., 2009[15] studied modulation of glial connexin and pannexin hemichannels and gap junctions and the effect of their activation in inflammation and neurodegeneration. Orellana et al., 2009 postulates the use of modulation of connexin and pannexin hemichannels and gap junctions for treatment of neurodegeneration, but does not postulate specifically connexin and pannexin hemichannels from astrocytes as a pharmacological target for psychiatric disorders; they are focused on complete CNS. Furthermore, this document also fails to mention the differential modulation, affecting hemichannels but not gap junctions.

Kawasaki et al., 2009[16] discloses that in astrocytes of a Parkinson's disease model, phosphorylated connexin is increased. Phosphorylated connexin is necessary for forming gap junctions, and the authors postulate that modulation of connexin 43 could be a pharmacological target for Parkinson's disease treatment. Kawasaki et al., 2009 is focused on connexin gap junctions, and not connexin hemichannels, as the present invention, and does not mention psychiatric disorders.

Behrens et al., 2011[17] studied the effect of a non-specific blocker of connexin 36, 43 and 50 gap junctions in epileptiform activity. It reported that mefloquine increases hyperpolarization of hippocampal pyramidal cells and promotes action potentials in epileptiform activity. Behrens et al., 2011 postulates connexin gap junctions from pyramidal neurons as a pharmacological target for the treatment of epilepsy, but does not include connexin hemichannels from astrocytes, nor mention psychiatric disorders.

Mitterauer, 2010[18] is a review of the effects of connexin gap junctions from astrocytes in memory. Mitterauer, 2010 is focused on connexin gap junctions and does not mention connexin hemichannels from astrocytes.

Desplantez et al., 2012[19] studied the effect of a peptide in connexin 43 hemichannels. Desplantez et al., 2012 does not postulate this peptide as pharmacological agent for psychiatric disorders, nor a role for astrocytes in these pathologies.

Davidson et al., 2012[20] studied the use of a connexin 43 mimetic peptide for blocking the opening of connexin 43 hemichannels in an ischemia model. They postulate connexins as pharmacological targets for ischemia, but do not indicate that connexin hemichannels from astrocytes can be used as pharmacological targets, and do not mention treating psychiatric disorders.

Sun, et al., 2012[21] studied the effect of connexin 43 mimetic peptides on the dysfunction of connexin 43 gap junction in astrocytes and its relation with depression pathophysiology. Sun, et al., 2012 postulates astrocytes and connexin 43 gap junctions as pharmacological targets, but it is focused on connexin 43 gap junctions and does not mention connexin 43 hemichannels.

O'Carroll et al., 2008[22] studied blocking of connexin 43 hemichannels with mimetic peptides corresponding to intracellular loop of connexin 43 for demonstrating that this inhibition is useful to diminish propagation of cellular death in astrogliosis. O'Carroll et al., 2008 does not show any relationship between psychiatric disorders and modulation of connexin 43 hemichannels.

Ponsaerts et al., 2010[23] studied the functionality of connexin 43 mimetic peptides in vitro. The results show that this type of peptides regulates opening of connexin 43 hemichannels and not connexin 43 gap junctions. Ponsaerts et al., 2010 does not mention psychiatric disorders nor connexin 43 hemichannels from astrocytes.

US20100029613A1[24] describes a method to treat or prevent epileptic seizures administering agents that interfere with astrocytic release of glutamate, aspartate and/or ATP. A method is also presented to identify agents that may have such effects. US20100029613A1 finally tests all previously known glutamate release pathways to determine the mechanisms by which such release may occur. US20100029613A1 mentions the work of Ye et al. 2003 as previous art, which suggests a role of connexin 43 hemichannels in astrocytic glutamate release. US20100029613A1 does not interfere with the present invention as it is based on calcium and ATP dependent astrocytic release of glutamate, ATP and aspartate and shows that such release, which is used as a marker for their agent identification and anti-seizure effects, is not dependent on astrocytic connexin 43 hemichannels. In order to justify their negative results, the authors cite Ye et al., 2003[2] suggesting that "Cx hemichannels may have a role in pathological conditions such as ischemia and epilepsy". In consequence, ischemia or epilepsy have been excluded from our invention, which only includes psychiatric disorders.

EP2344146A1[25] is related to a product comprising at least one connexin blocking agent and a psychotropic drug, to be used simultaneously, separately, or spread over time in patients suffering from psychiatric and/or neurodegenerative disorders. EP2344146A1 is not related to the present invention, since it discloses the use of blocking agents for neuronal gap junctions as adjuvants for improving treatment of different psychiatric and/or neurological disorders, and it does not consider either astrocytes or hemichannels.

EP2322149A1[26] discloses the use of a pannexin hemichannel inhibitor to treat white matter ischemia, periventricular leukomalacia, optic nerve ischemia, mild cognitive impairment and subcortical vascular dementia. EP2322149A1 does not interfere with the present invention, since it mentions participation of pannexin hemichannels from oligodendrocytes and it does not mention astrocytes, or connexins, or psychiatric disorders.

WO2006134494A2[27] describes methods and compositions to modulate connexin activity for treatment of cardiovascular, vascular, neurologic disorders, for treating wounds and other indications. WO2006134494A2 indicates that these compounds and methods could be used, for example, to reduce severity of adverse effects in diseases and disorders where localized disruption of direct cell-cell communication or prevention of hemichannel opening is desirable. WO2006134494A2 focuses on uses of anticonnexin compounds on neurological disorders, based on vascular effects of connexins in response to ischemia. It does not mention astrocytes, nor psychiatric disorders.

WO2007002285A2[28] discloses new methods for treating neurologic and psychiatric conditions. The methods comprise modulating production or activity of one or more substances that participate in signaling of calcium or release of glutamate from astrocytes, modulating the intracellular concentration of calcium in astrocytes, modulating expression or release of D-serine, or modulating expression or release of ATP or adenosine. Methods of detecting compounds with the ability to target to specific pathways or intracellular calcium are also disclosed. WO2007002285A2 focuses on modulation of astrocytic release of substances for the treatment of different disorders including psychiatric disorders and on the use of compounds that affect intracellular or extracellular regulation pathways for this release, for example, affecting calcium or adenosine levels, but they do not include release pathways, in particular, they do not mention connexin (43 or 30) or pannexin 1 hemichannels.

SUMMARY

This disclosure relates to the use of compounds or pharmaceutically acceptable salts thereof that modulate astrocytic release of substances through connexin and pannexin hemichannels, while not influencing or disturbing the function of gap junctions, for the treatment of psychiatric disorders.

Compounds or pharmaceutically acceptable salts thereof comprise any compound that differentially modulates, blocks, opens, affects, inhibits, and/or activates connexin and/or pannexin hemichannels and not gap junctions from astrocytes.

This disclosure also relates to a method of treating psychiatric disorders, comprising administering to a mammal or human a therapeutically effective amount of a compound or a pharmaceutically acceptable salt thereof that modulates astrocytic release of substances through connexin and pannexin hemichannels and not through gap junctions.

Pharmaceutical compositions and a screening method are also disclosed.

DETAILED DESCRIPTION

Our in vivo and in vitro research demonstrates that the activity of connexin and pannexin hemichannels from astrocytes is required for the astrocytic release of neuroactive substances into the synapses (gliotransmitters). The effect of connexin hemichannels blockage from astrocytes with specific peptides is prevented by co-injection with a mixture of putative gliotransmitters into the basolateral amygdala (BLA), which demonstrates that connexin hemichannels from astrocytes mediate the release of some of those substances. This notion is supported by an increasing number of in vitro studies suggesting that gliotransmitter release from astrocytes is necessary for neuronal plasticity, comprising ATP, glutamate and D-serine[1, 4, 5, 6, 7, 8].

The connexins of interest, connexin 43 and connexin 30 are found only in astrocytes but not in neurons. On the other hand, Pannexin 1 is expressed in both astrocytes and neurons [3,29]. Compounds for blocking connexin and pannexin hemichannels from astrocytes do not affect inter-astrocyte communication, a process known to be mediated by connexin gap junctions. Results from our in vitro assays demonstrate that compounds affect only connexin 30 and 43 hemichannels and pannexin hemichannels from astrocytes leaving inter-neuronal and inter-astrocyte transmission intact.

Our results demonstrate that astrocytic release of gliotransmitters is necessary for higher brain function. To our knowledge this is the first evidence showing a physiological role in vivo for connexin and pannexin hemichannels from astrocytes in the brain.

The release of neuroactive substances from the astrocyte into extracellular space is well documented. These gliotransmitters comprise glutamate, D-serine, ATP, adenosine, G-amino butyric acid, tumor necrosis factor alpha (TNF-α), prostaglandins, atrial natriuretic peptide and brain-derived neurotrophic factor. Some of these gliotransmitters have been shown to modulate neuronal activity and synaptic plasticity[1, 3, 5, 6, 7, 8]. Possible pathways by which gliotransmitters are released from astrocytes comprise connexin and pannexin hemichannels. However, it is well accepted that connexin 43 hemichannels are permeable to ATP and glutamate[2, 37] and are likely to be permeable to several other gliotransmitters. Here we show that the modulation of connexin or pannexin hemichannel activity in astrocytes induces several effects on different psychiatric disease models, demonstrating that connexin and pannexin hemichannels in astrocytes mediate or contribute to the release of gliotransmitter to the neuronal synapses, with potential uses for the treatment of psychiatric disorders.

We provide compounds or pharmaceutically acceptable salts thereof that modulate astrocytic release of substances through connexin or pannexin hemichannels without influencing or disturbing the function of gap junctions for the treatment of psychiatric disorders.

Preferably, the aforementioned connexin hemichannels correspond to connexin 30 and connexin 43 hemichanels and aforementioned pannexin hemichannels correspond to pannexin 1 hemichanels.

The used compounds or pharmaceutically acceptable salts thereof differentially modulate, block, open, inhibit, and/or activate connexin and/or pannexin hemichannels or a combination thereof from astrocytes while not affecting gap junctions directly.

Preferably, the used compounds or pharmaceutically acceptable salts thereof block or open connexin and/or pannexin hemichannels from astrocytes or a combination thereof.

The compounds or pharmaceutically acceptable salts thereof may be connexin or pannexin mimetic peptides, which relate to peptides that mimic regions of the protein sequence of the target hemichannels, thus affecting their opening probability and physiological activity. More preferably, the compounds or pharmaceutically acceptable salts thereof are peptides that correspond to any region of a connexin or a pannexin.

Preferably, the compounds or pharmaceutically acceptable salts thereof are peptides that correspond to any region of connexin 43 or connexin 30 or pannexin 1.

More preferably, the compounds or pharmaceutically acceptable salts thereof are peptides that correspond to a region of the cytoplasmic loop of connexin 43 or connexin 30 or pannexin 1.

The compounds or pharmaceutically acceptable salts thereof may be peptides that correspond to a region of any extracellular loop of a connexin or a pannexin. More preferably, the compounds or pharmaceutically acceptable salts thereof are peptides that correspond to a region of any extracellular loop of connexin 43 or connexin 30 or pannexin 1.

The compounds or pharmaceutically acceptable salts thereof may be peptides that correspond to a region of the C-terminal domain of a connexin or a pannexin. More preferably, the compounds or pharmaceutically acceptable salts thereof are peptides that correspond to a region of the c-terminal domain of connexin 43 or connexin 30 or pannexin 1.

The compounds or pharmaceutically acceptable salts thereof may be peptides that interfere with functioning of connexins or pannexins or a combination thereof in their hemichannel configuration.

The compounds or pharmaceutically acceptable salts thereof may be peptides that interfere with functioning of connexin 30 or connexin 43 or pannexin 1 or a combination thereof in their hemichannel configuration.

The compounds or pharmaceutically acceptable salts thereof may be any compound whether natural or artificially synthesized that may specifically affect connexin 43 or connexin 30 or pannexin 1 hemichannels or a combination thereof in the astrocytes without affecting gap junctions.

In one non limiting example, the compound is selected between, but not limited to:

```
                                        SEQ ID NO: 1
Tyr Gly Arg Lys Lys Arg Arg Gln Arg Arg Arg Asp

Gly Ala Asn Val Asp Met His Leu Lys Gln Ile Glu

Ile Lys Lys Phe Lys Tyr Gly Ile Glu Glu His Gly

Lys (TAT-Cx43L2),

SEQ ID NO: 2
Asp Gly Ala Asn Val Asp Met His Leu Lys Gln Ile

Glu Ile Lys Lys Phe Lys Tyr Gly Ile Glu Glu His

Gly Lys,
                                        SEQ ID NO: 3
Tyr Gly Arg Lys Lys Arg Arg Gln Arg Arg Arg Lys

Gln Ile Glu Ile Lys Lys Phe Lys (Gap19),
or
                                        SEQ ID NO: 4
Lys Gln Ile Glu Ile Lys Lys Phe Lys
or pharmaceutically acceptable salts thereof.
```

Preferably, the compound is selected between, but not limited to:

SEQ ID NO: 5
Tyr Gly Arg Lys Lys Arg Arg Gln Arg Arg Arg

Pro Arg Pro Asp Asp Leu Glu (TAT-CT9 Delta),

SEQ ID NO: 6
Arg Pro Arg Pro Asp Asp Leu Glu,

SEQ ID NO: 7
Tyr Gly Arg Lys Lys Arg Arg Gln Arg Arg Xaa

Pro Xaa Pro Asp Asp Leu Glu, wherein Xaa is independently Arg,

His, Lys, Cys, Gly, Gln, Asn, Ser, Tyr, or Thr,

SEQ ID NO: 8
Xaa Pro Xaa Pro Asp Asp Leu Glu, wherein Xaa is independently Arg,

His, Lys, Cys, Gly, Gln, Asn, Ser, Tyr, or Thr,

SEQ ID NO: 9
Tyr Gly Arg Lys Lys Arg Arg Gln Arg Arg Arg

Xaa Arg Xaa Asp Asp Leu Glu, wherein Xaa is independently Phe,

Ala, Leu, Met, Ile, Trp, Pro, or Val,

SEQ ID NO: 10
Arg Xaa Arg Xaa Asp Asp Leu Glu wherein Xaa is independently Phe,

Ala, Leu, Met, Ile, Trp, Pro, or Val,

SEQ ID NO: 11
Tyr Gly Arg Lys Lys Arg Arg Gln Arg Arg Arg

Pro Arg Pro Xaa Xaa Leu Xaa, wherein Xaa is independently Asp,

Glu, Cys, Gly, Gln, Asn, Ser, Tyr, or Thr,

SEQ ID NO: 12
Arg Pro Arg Pro Xaa Xaa Leu Xaa, wherein Xaa is independently Asp, Glu, Cys, Gly, Gln, Asn, Ser, Tyr, or Thr, SEQ ID NO: 13
Tyr Gly Arg Lys Lys Arg Arg Gln Arg Arg Xaa Gln Ile Glu Ile Xaa Xaa Phe Xaa, wherein Xaa is independently Arg, His, Lys, Cys, Gly, Gln, Asn, Ser, Tyr, or Thr, SEQ ID NO: 14
Xaa Gln Ile Glu Ile Xaa Xaa Phe Xaa, wherein Xaa is independently Arg, His, Lys, Cys, Gly, Gln, Asn, Ser, Tyr, or Thr, SEQ ID NO: 15
Tyr Gly Arg Lys Lys Arg Arg Gln Arg Arg Lys Xaa Ile Glu Ile Lys Lys Phe Lys, wherein Xaa is independently Cys, Gly, Gln, Asn, Ser, Tyr, Thr, Asp, Glu, Arg, His, or Lys, SEQ ID NO: 16
Lys Xaa Ile Glu Ile Lys Lys Phe Lys, wherein Xaa is independently Cys, Gly, Gln, Asn, Ser, Tyr, Thr, Asp, Glu, Arg, His, or Lys, SEQ ID NO: 17
Tyr Gly Arg Lys Lys Arg Arg Gln Arg Arg Lys Gln Xaa Glu Ile Lys Lys Phe Lys, wherein Xaa is independently Phe, Ala, Leu, Met, Ile, Trp, Pro, or Val, SEQ ID NO: 18
Lys Gln Xaa Glu Ile Lys Lys Phe Lys, wherein Xaa is independently Phe, Ala, Leu, Met, Ile, Trp, Pro, or Val, SEQ ID NO: 19
Tyr Gly Arg Lys Lys Arg Arg Gln Arg Arg Lys Gln Ile Xaa Ile Lys Lys Phe Lys, wherein Xaa is independently Asp, Glu, Cys, Gly, Gln, Asn, Ser, Tyr, or Thr, SEQ ID NO: 20
Lys Gln Ile Xaa Ile Lys Lys Phe Lys, wherein Xaa is independently Asp, Glu, Cys, Gly, Gln, Asn, Ser, Tyr, or Thr, SEQ ID NO: 21
Tyr Gly Arg Lys Lys Arg Arg Gln Arg Arg Val Asp Cys Phe Leu Ser Arg Pro Thr Glu Lys Thr (TAT-Peptide 5), SEQ ID NO: 22
Val Asp Cys Phe Leu Ser Arg Pro Thr Glu Lys Thr, SEQ ID NO: 23
Tyr Gly Arg Lys Lys Arg Arg Gln Arg Arg Xaa Cys Asp Xaa Xaa Ser Arg Xaa Thr Glu Lys Thr, wherein Xaa is independently Phe, Ala, Leu, Met, Ile, Trp, Pro, or Val, SEQ ID NO: 24
Xaa Cys Asp Xaa Xaa Ser Arg Xaa Thr Glu Lys Thr, wherein Xaa is independently Phe, Ala, Leu, Met, Ile, Trp, Pro, or Val, SEQ ID NO: 25
Tyr Gly Arg Lys Lys Arg Arg Gln Arg Arg Val Xaa Cys Phe Leu Ser Arg Pro Thr Xaa Lys Thr, wherein Xaa is independently Asp, Glu, Cys, Gly, Gln, Asn, Ser, Tyr, or Thr, SEQ ID NO: 26
Val Xaa Cys Phe Leu Ser Arg Pro Thr Xaa Lys Thr, wherein Xaa is independently Asp, Glu, Cys, Gly, Gln, Asn, Ser, Tyr, or Thr, SEQ ID NO: 27
Tyr Gly Arg Lys Lys Arg Arg Gln Arg Arg Arg Val Asp Xaa Phe Leu Xaa Arg Pro Xaa Glu Lys Xaa, wherein Xaa is independently Cys, Gly, Gln, Asn, Ser, Tyr, Thr, Asp, Glu, Arg, His, or Lys, SEQ ID NO: 28
Val Asp Xaa Phe Leu Xaa Arg Pro Xaa Glu Lys Xaa, wherein Xaa is independently Cys, Gly, Gln, Asn, Ser, Tyr, Thr, Asp, Glu, Arg, His, or Lys, SEQ ID NO: 29
Tyr Gly Arg Lys Lys Arg Arg Gln Arg Arg Arg Val Asp Cys Phe Leu Ser Xaa Pro Thr Arg Xaa Thr, wherein Xaa is independently Arg, His, Lys, Cys, Gly, Gln, Asn, Ser, Tyr, or Thr, SEQ ID NO: 30
Val Asp Cys Phe Leu Ser Xaa Pro Thr Arg Xaa Thr, wherein Xaa is independently Arg, His, Lys, Cys, Gly, Gln, Asn, Ser, Tyr, or Thr, SEQ ID NO: 31
Tyr Gly Arg Lys Lys Arg Arg Gln Arg Arg Arg Trp Arg Gln Ala Ala Phe Val Asp Ser Tyr (TAT-Pnx1), SEQ ID NO: 32
Trp Arg Gln Ala Ala Phe Val Asp Ser Tyr, SEQ ID NO: 33
Tyr Gly Arg Lys Lys Arg Arg Gln Arg Arg Arg Xaa Arg Gln Xaa Xaa Xaa Xaa Asp Ser Tyr, wherein Xaa is independently Phe, Ala, Leu, Met, Ile, Trp, Pro, or Val, SEQ ID NO: 34
Xaa Arg Gln Xaa Xaa Xaa Xaa Asp Ser Tyr, wherein Xaa is independently Phe, Ala, Leu, Met, Ile, Trp, Pro, or Val, SEQ ID NO: 35
Tyr Gly Arg Lys Lys Arg Arg Gln Arg Arg Arg Trp Xaa Gln Ala Ala Phe Val Asp Ser Tyr, wherein Xaa is independently Arg, His, Lys, Cys, Gly, Gln, Asn, Ser, Tyr, or Thr, SEQ ID NO: 36
Trp Xaa Gln Ala Ala Phe Val Asp Ser Tyr, wherein Xaa is independently Arg, His, Lys, Cys, Gly, Gln, Asn, Ser, Tyr, or Thr SEQ ID NO: 37
Tyr Gly Arg Lys Lys Arg Arg Gln Arg Arg Arg Trp Arg Xaa Ala Ala Phe Val Asp Xaa Xaa, wherein Xaa is independently Cys, Gly, Gln, Asn, Ser, Tyr, Thr, Asp, Glu, Arg, His, or Lys, SEQ ID NO: 38
Trp Arg Xaa Ala Ala Phe Val Asp Xaa Xaa, wherein Xaa is independently Cys, Gly, Gln, Asn, Ser, Tyr, Thr, Asp, Glu, Arg, His, or Lys, SEQ ID NO: 39
Tyr Gly Arg Lys Lys Arg Arg Gln Arg Arg Arg Trp Arg Gln Ala Ala Phe Val Xaa Ser Tyr, wherein Xaa is independently Asp, Glu, Cys, Gly, Gln, Asn, Ser, or Tyr, SEQ ID NO: 40
Trp Arg Gln Ala Ala Phe Val Xaa Ser Tyr, wherein Xaa is independently Asp, Glu, Cys, Gly, Gln, Asn, Ser, or Tyr, SEQ ID NO: 41
Tyr Gly Arg Lys Lys Arg Arg Gln Arg Arg Arg Ser Ser Phe Ser Trp Arg Gln Ala Ala Phe Val Asp Ser (TAT-E1b), SEQ ID NO: 42
Ser Ser Phe Ser Trp Arg Gln Ala Ala Phe Val Asp Ser, SEQ ID NO: 43
Tyr Gly Arg Lys Lys Arg Arg Gln Arg Arg Arg Xaa Xaa Phe Xaa Trp Arg Xaa Ala Ala Phe Val Asp Xaa, wherein Xaa is independently Cys, Gly, Gln, Asn, Ser, Tyr, Thr, Asp, Glu, Arg, His, or Lys, SEQ ID NO: 44
Xaa Xaa Phe Xaa Trp Arg Xaa Ala Ala Phe Val Asp Xaa, wherein Xaa is independently Cys, Gly, Gln, Asn, Ser, Tyr, Thr, Asp, Glu, Arg, His, or Lys, -continued SEQ ID NO: 45
Tyr Gly Arg Lys Lys Arg Arg Gln Arg Arg Arg Ser
Ser Xaa Ser Xaa Arg Gln Xaa Xaa Xaa Xaa Asp Ser,
wherein Xaa is independently Phe,
Ala, Leu, Met, Ile, Trp, Pro, or Val, SEQ ID NO: 46
Ser Ser Xaa Ser Xaa Arg Gln Xaa Xaa Xaa Xaa Asp
Ser, wherein Xaa is independently Phe,
Ala, Leu, Met, Ile, Trp, Pro, or Val, SEQ ID NO: 47
Tyr Gly Arg Lys Lys Arg Arg Gln Arg Arg Arg Ser
Ser Phe Ser Trp Xaa Gln Ala Ala Phe Val Asp Ser,
wherein Xaa is independently Arg,
His, Lys, Cys, Gly, Gln, Asn, Ser, Tyr, or Thr, SEQ ID NO: 48
Ser Ser Phe Ser Trp Xaa Gln Ala Ala Phe Val Asp
Ser, wherein Xaa is independently Arg,
His, Lys, Cys, Gly, Gln, Asn, Ser, Tyr, or Thr, SEQ ID NO: 49
Tyr Gly Arg Lys Lys Arg Arg Gln Arg Arg Arg Ser
Ser Phe Ser Trp Arg Gln Ala Ala Phe Val Xaa Ser,
wherein Xaa is independently Asp,
Glu, Cys, Gly, Gln, Asn, Ser, or Tyr, SEQ ID NO: 50
Ser Ser Phe Ser Trp Arg Gln Ala Ala Phe Val Xaa
Ser, wherein Xaa is independently Asp,
Glu, Cys, Gly, Gln, Asn, Ser, or Tyr, SEQ ID NO: 51
Tyr Gly Arg Lys Lys Arg Arg Gln Arg Arg Arg
Asp Leu Asp Leu Arg Asp Gly Pro (TAT-Pnx1L5), SEQ ID NO: 52
Asp Leu Asp Leu Arg Asp Gly Pro, SEQ ID NO: 53
Tyr Gly Arg Lys Lys Arg Arg Gln Arg Arg Arg Xaa
Leu Xaa Leu Arg Xaa Gly Pro,
wherein Xaa is independently Asp,
Glu, Cys, Gly, Gln, Asn, Ser, Tyr, Arg, His,
or Lys, SEQ ID NO: 54
Xaa Leu Xaa Leu Arg Xaa Gly Pro,
wherein Xaa is independently Asp,
Glu, Cys, Gly, Gln, Asn, Ser, Tyr, Arg, His,
or Lys.

SEQ ID NO: 55
Tyr Gly Arg Lys Lys Arg Arg Gln Arg Arg Arg Asp
Xaa Asp Xaa Arg Asp Gly Xaa, wherein Xaa is independently Phe,
Ala, Leu, Met, Ile, Trp, Pro, or Val, SEQ ID NO: 56
Asp Xaa Asp Xaa Arg Asp Gly Xaa,
wherein Xaa is independently Phe,
Ala, Leu, Met, Ile, Trp, Pro, or Val, SEQ ID NO: 57
Tyr Gly Arg Lys Lys Arg Arg Gln Arg Arg Arg Asp
Leu Asp Leu Xaa Asp Gly Pro,
wherein Xaa is independently Arg, His, Lys, Cys,
Gly, Gln, Asn, Ser, Tyr, or Thr, SEQ ID NO: 58
Asp Leu Asp Leu Xaa Asp Gly Pro,
wherein Xaa is independently Arg,
His, Lys, Cys, Gly, Gln, Asn, Ser, Tyr, or Thr, SEQ ID NO: 59
Tyr Gly Arg Lys Lys Arg Arg Gln Arg Arg Arg Asp
Leu Asp Leu Arg Asp Xaa Pro,
wherein Xaa is independently Cys,
Gly, Gln, Asn, Ser, Tyr, Thr, Asp, Glu, Arg,
His, or Lys, SEQ ID NO: 60
Asp Leu Asp Leu Arg Asp Xaa Pro,
wherein Xaa is independently Cys,
Gly, Gln, Asn, Ser, Tyr, Thr, Asp, Glu, Arg,
His, or Lys, SEQ ID NO: 61
Tyr Gly Arg Lys Lys Arg Arg Gln Arg Arg Arg Pro
Met Ser Leu Gln Thr Lys Gly Glu (TAT-Pnx1ct), SEQ ID NO: 62
Pro Met Ser Leu Gln Thr Lys Gly Glu, SEQ ID NO: 63
Tyr Gly Arg Lys Lys Arg Arg Gln Arg Arg Arg Xaa
Xaa Ser Xaa Gln Thr Lys Gly Glu,
wherein Xaa is independently Phe,
Ala, Leu, Met, Ile, Trp, Pro, or Val, SEQ ID NO: 64
Xaa Xaa Ser Xaa Gln Thr Lys Gly Glu,
wherein Xaa is independently Phe,
Ala, Leu, Met, Ile, Trp, Pro, or Val, SEQ ID NO: 65
Tyr Gly Arg Lys Lys Arg Arg Gln Arg Arg Arg Pro
Met Xaa Leu Xaa Xaa Lys Xaa Glu, -continued wherein Xaa is independently Cys,
Gly, Gln, Asn, Ser, Tyr, Thr, Asp, Glu, Arg,
His, or Lys, SEQ ID NO: 66
Pro Met Xaa Leu Xaa Xaa Lys Xaa Glu,
wherein Xaa is independently Cys,
Gly, Gln, Asn, Ser, Tyr, Thr, Asp, Glu, Arg,
His, or Lys, SEQ ID NO: 67
Tyr Gly Arg Lys Lys Arg Arg Gln Arg Arg Pro
Met Ser Leu Gln Thr Xaa Gly Glu,
wherein Xaa is independently Arg,
His, Lys, Cys, Gly, Gln, Asn, Ser, Tyr, or Thr, SEQ ID NO: 68
Pro Met Ser Leu Gln Thr Xaa Gly Glu,
wherein Xaa is independently Arg,
His, Lys, Cys, Gly, Gln, Asn, Ser, Tyr, or Thr, SEQ ID NO: 69
Tyr Gly Arg Lys Lys Arg Arg Gln Arg Arg Pro
Met Ser Leu Gln Thr Lys Gly Xaa,
wherein Xaa is independently Asp,
Glu, Cys, Gly, Gln, Asn, Ser, Tyr, or Thr, SEQ ID NO: 70
Pro Met Ser Leu Gln Thr Lys Gly Xaa,
wherein Xaa is independently Asp,
Glu, Cys, Gly, Gln, Asn, Ser, Tyr, or Thr, SEQ ID NO: 71
Tyr Gly Arg Lys Lys Arg Arg Gln Arg Arg Asp
Ala Pro Ala Leu Tyr Ser Asn Leu Ser Lys Lys Arg
Gly (TAT-Cx30L4), SEQ ID NO: 72
Asp Ala Pro Ala Leu Tyr Ser Asn Leu Ser Lys Lys
Arg Gly, SEQ ID NO: 73
Tyr Gly Arg Lys Lys Arg Arg Gln Arg Arg Xaa
Ala Pro Ala Leu Tyr Ser Asn Leu Ser Lys Lys Arg
Gly, wherein Xaa is independently Asp,
Glu, Cys, Gly, Gln ,Asn, Ser, or Tyr, SEQ ID NO: 74
Xaa Ala Pro Ala Leu Tyr Ser Asn Leu Ser Lys Lys
Arg Gly, wherein Xaa is independently Asp,
Glu, Cys, Gly, Gln, Asn, Ser, or Tyr, SEQ ID NO: 75
Tyr Gly Arg Lys Lys Arg Arg Gln Arg Arg Asp
Xaa Xaa Xaa Xaa Tyr Ser Asn Xaa Ser Lys Lys Arg
Gly, wherein Xaa is independently Phe,
Ala, Leu, Met, Ile, Trp, Pro, or Val, SEQ ID NO: 76
Asp Xaa Xaa Xaa Xaa Tyr Ser Asn Xaa Ser Lys Lys
Arg Gly, wherein Xaa is independently Phe,
Ala, Leu, Met, Ile, Trp, Pro, or Val, SEQ ID NO: 77
Tyr Gly Arg Lys Lys Arg Arg Gln Arg Arg Asp
Ala Pro Ala Leu Xaa Xaa Xaa Leu Xaa Lys Lys Arg
Xaa, wherein Xaa is independently Cys, Gly, Gln,
Asn, Ser, Tyr, Thr, Asp, Glu, Arg, His, or Lys, SEQ ID NO: 78
Asp Ala Pro Ala Leu Xaa Xaa Xaa Leu Xaa Lys Lys
Arg Xaa, wherein Xaa is independently Cys, Gly,
Gln, Asn, Ser, Tyr, Thr, Asp, Glu, Arg, His,
or Lys, SEQ ID NO: 79
Tyr Gly Arg Lys Lys Arg Arg Gln Arg Arg Asp
Ala Pro Ala Leu Tyr Ser Asn Leu Ser Xaa Xaa Xaa
Gly, wherein Xaa is independently Arg, His, Lys,
Cys, Gly, Gln, Asn, Ser, Tyr, or Thr, SEQ ID NO: 80
Asp Ala Pro Ala Leu Tyr Ser Asn Leu Ser Xaa Xaa
Xaa Gly, wherein Xaa is independently Arg, His,
Lys, Cys, Gly, Gln, Asn, Ser, Tyr, or Thr, SEQ ID NO: 81
Tyr Gly Arg Lys Lys Arg Arg Gln Arg Arg Thr
Cys Pro Pro Tyr Val Ile Ser Lys Gly His Pro Gln
(TAT-Cx30ct), SEQ ID NO: 82
Thr Cys Pro Pro Tyr Val Ile Ser Lys Gly His Pro
Gln, SEQ ID NO: 83
Tyr Gly Arg Lys Lys Arg Arg Gln Arg Arg Xaa
Xaa Pro Pro Xaa Val Ile Lys Xaa His Pro Xaa,
wherein Xaa is independently Cys,
Gly, Gln, Asn, Ser, Tyr, Thr, Asp, Glu, Arg,
His, or Lys, SEQ ID NO: 84
Xaa Xaa Pro Pro Xaa Val Ile Lys Xaa His Pro Xaa,
wherein Xaa is independently Cys,
Gly, Gln, Asn, Ser, Tyr, Thr, Asp, Glu, Arg,
His, or Lys, SEQ ID NO: 85
Tyr Gly Arg Lys Lys Arg Arg Gln Arg Arg Thr
Cys Xaa Xaa Tyr Xaa Xaa Ser Lys Gly His Xaa Gln, wherein Xaa is independently Phe, Ala, Leu, Met, Ile, Trp, Pro, or Val, SEQ ID NO: 86
Thr Cys Xaa Xaa Tyr Xaa Xaa Ser Lys Gly His Xaa Gln, wherein Xaa is independently Phe, Ala, Leu, Met, Ile, Trp, Pro, or Val, SEQ ID NO: 87
Tyr Gly Arg Lys Lys Arg Arg Gln Arg Arg Arg Thr Cys Pro Pro Tyr Val Ile Ser Xaa Gly Xaa Pro Gln, wherein Xaa is independently Arg, His, Lys, Cys, Gly, Gln, Asn, Ser, Tyr, or Thr, SEQ ID NO: 88
Thr Cys Pro Pro Tyr Val Ile Ser Xaa Gly Xaa Pro Gln, wherein Xaa is independently Arg, His, Lys, Cys, Gly, Gln, Asn, Ser, Tyr, or Thr, SEQ ID NO: 89
Tyr Gly Arg Lys Lys Arg Arg Gln Arg Arg Arg Cys Tyr Asp His Phe Phe Pro Val Ser His Ile Arg (TAT-Cx30), SEQ ID NO: 90
Cys Tyr Asp His Phe Phe Pro Val Ser His Ile Arg, SEQ ID NO: 91
Tyr Gly Arg Lys Lys Arg Arg Gln Arg Arg Arg Xaa Xaa Asp His Phe Phe Pro Val Xaa His Ile Arg, wherein Xaa is independently Cys, Gly, Gln, Asn, Ser, Tyr, Thr, Asp, Glu, Arg, His, or Lys, SEQ ID NO: 92
Xaa Xaa Asp His Phe Phe Pro Val Xaa His Ile Arg, wherein Xaa is independently Cys, Gly, Gln, Asn, Ser, Tyr, Thr, Asp, Glu, Arg, His, or Lys, SEQ ID NO: 93
Tyr Gly Arg Lys Lys Arg Arg Gln Arg Arg Arg Cys Tyr Xaa His Phe Phe Pro Val Ser His Ile Arg, wherein Xaa is independently Asp, Glu, Cys, Gly, Gln, Asn, Ser, Tyr, or Thr, SEQ ID NO: 94
Cys Tyr Xaa His Phe Phe Pro Val Ser His Ile Arg, wherein Xaa is independently Asp, Glu, Cys, Gly, Gln, Asn, Ser, Tyr, or Thr, SEQ ID NO: 95
Tyr Gly Arg Lys Lys Arg Arg Gln Arg Arg Arg Cys Tyr Asp Xaa Phe Phe Pro Val Ser Xaa Ile Xaa, wherein Xaa is independently Arg, His, Lys, Cys, Gly, Gln, Asn, Ser, Tyr, or Thr, SEQ ID NO: 96
Cys Tyr Asp Xaa Phe Phe Pro Val Ser Xaa Ile Xaa, wherein Xaa is independently Arg, His, Lys, Cys, Gly, Gln, Asn, Ser, Tyr, or Thr, SEQ ID NO: 97
Tyr Gly Arg Lys Lys Arg Arg Gln Arg Arg Arg Cys Tyr Asp His Xaa Xaa Xaa Xaa Ser His Xaa Arg, wherein Xaa is independently Phe, Ala, Leu, Met, Ile, Trp, Pro, or Val, Or SEQ ID NO: 98
Cys Tyr Asp His Xaa Xaa Xaa Xaa Ser His Xaa Arg, wherein Xaa is independently Phe, Ala, Leu, Met, Ile, Trp, Pro, or Val.

SEQ ID NO: 99
Xaa Pro Xaa Pro Asp Asp Xaa Xaa Xaa, wherein Xaa is independently any aminoacid SEQ ID NO: 100
Arg Pro Arg Pro Xaa Xaa Leu Glu, wherein Xaa is independently Asp, Glu, Ser, Thr, Cys, Asn, Gln SEQ ID NO: 101
Arg Xaa Arg XaaAsp Asp Leu Glu, wherein Xaa is independently Phe, Ala, Leu, Met, Ile, Trp, Pro, Val SEQ ID NO: 102
Xaa Pro Xaa Pro Asp Asp Xaa Xaa, wherein Xaa is independently any aminoacid SEQ ID NO: 103
Arg Xaa Arg Xaa Asp Asp Xaa Xaa, wherein Xaa is independently Pro, His, Phe, Trp, Tyr SEQ ID NO: 104
Arg Pro Arg Pro Xaa Xaa Leu Glu, wherein Xaa is independently Asp, Glu, Ser, Thr, Cys, Asn, Gln SEQ ID NO: 105
Xaa Pro Xaa Pro Asp Asp Xaa Xaa, wherein Xaa is independently any amino acid SEQ ID NO: 106
Arg Xaa Arg Pro Asp Asp Xaa Xaa, wherein Xaa is independently Pro, His, Phe, Trp, Tyr -continued SEQ ID NO: 107
Arg Pro Arg Xaa Asp Asp Xaa Xaa, wherein Xaa is independently Asp, Glu, Ser, Thr, Cys, Asn, Gln SEQ ID NO: 108
Xaa Xaa Pro Xaa Asp Asp Xaa Xaa, wherein Xaa is independently any amino acid SEQ ID NO: 109
Lys Xaa Xaa Xaa Ile Lys Lys Phe Lys, wherein Xaa is independently any amino acid SEQ ID NO: 110
Xaa Gln Ile Xaa Ile Xaa Xaa Phe Lys, wherein Xaa is independently any amino acid SEQ ID NO: 111
Lys Gln Ile Glu Xaa Lys Lys Xaa Xaa, wherein Xaa is independently any amino acid SEQ ID NO: 112
Xaa Xaa Ile Xaa Xaa Xaa Lys Xaa Xaa, wherein Xaa is independently any amino acid SEQ ID NO: 113
Xaa Asp Xaa Xaa Leu Ser Arg Pro Thr Arg Xaa Xaa Xaa, wherein Xaa is independently any amino acid SEQ ID NO: 114
Asp Xaa Asp Xaa Xaa Asp Xaa Xaa, wherein Xaa is independently any amino acid SEQ ID NO: 115
Xaa Xaa Phe Xaa Trp Xaa Xaa Ala Ala Phe Val Asp Xaa, wherein Xaa is independently Cys, Gly, Gln, Asn, Ser, Tyr, Thr, Asp, Glu, Arg, His, lys Both L- and D-enantiomers of any aminoacid can be comprised in the compounds used.

Compounds may also comprise non-genetically encoded amino acids comprising but not limited to β-alanine (b-Ala); 3-aminopropionic acid; 2,3-diaminopropionic acid; 4-aminobutyric acid; 2,3-diaminobutyric acid; α-aminoisobutyric acid; ε-aminohexanoic acid; δ-aminovaleric acid; homoarginine; tbutylalanine; t-butylglycine; 3-carboxylic acid; citrulline; cyclohexylalanine; chlorophenylalanine; homocysteine; methylglycine; ornithine; N-methylisoleucine; methionine sulfoxide; norleucine; 2-naphthylalanine; 4-2-fluorophenylalanine; 3-fluorophenylalanine; 4-fluorophenylalanine; penicillamine; 1,2,3,4-tetrahydroisoquinoline-beta.-2-thienylalanine; N-acetyl lysine; phenylglycine; p-aminophenylalanine; N-methyl valine; homoserine; 3-benzothiazol-2-yl-alanine. They may also comprise amino acid analogs comprising phosphoserine, phosphotyrosine, phosphothreonine, gamma-carboxyglutamate, hydroxyproline, octahydroindole-2-carboxylic acid, hippuric acid, α-methyl-alanine, sarcosine, para-benzoyl-phenylalanine, statine, propargylglycine or any other amino acid known in the art, whether presently or in the future.

The compounds may comprise L-amino acids or retro-inverso D-amino acids or D-amino acids added at the N- or C-terminus of the peptides. The compounds may comprise cyclized/stapled and non-cyclized peptides. The compounds may comprise peptide analogs to those of the template peptide that may have analog properties, which may be non-peptide drugs that are structurally similar to the peptide but may have peptide linkages replaced by —CH2NH—, —CH2S—, —CH=CH— (cis and trans), —COCH2-, —CH2-CH2-, —CH2SO—, —CH(OH)CH2- or other chemical groups. Compounds may also have one or more peptides and may be a part of a larger molecule or protein. Compounds may be peptide-based or non-peptide based compounds. We also provide one or more peptides fused to a second protein or peptide to generate a fusion protein. These sequences can then be inserted into a second protein or peptide loop to provide three-dimensional structure to the region of the fusion protein.

The compounds may comprise any addition of sequences or moieties that facilitate the cell entry of the peptides, crossing the brain blood barrier, or serving as epitope for antibodies.

In one non limiting example, the used compound is selected between, but not limited to:
(2S)-5-phenyl-2-[(2R)-5-phenyl-2,3-dihydro-1,3-benzoxazol-2-yl]-2,3-dihydro-1,3-benzoxazole, 1-N,4-N-bis[3-(1H-benzimidazol-2-yl)phenyl]benzene-1,4-dicarboxamide, (8S,9R,10S,11 S,13R,14S,17S)-11-hydroxy-10,13-dimethyl-17-(2-phenyl-1,3-thiazol-4-yl)-1,2,6,7,8,9,11, 12,14,15,16,17-dodecahydrocyclopenta[a]phenanthren-3-one, Tricinolone acetophenonide, 3-phenyl-2-[4-[4-(3-phenylquinoxalin-2-yl)phenyl]sulfanylphenyl]-quinoxaline, 2-(nitro-dioxo-BLAHyl)acetic, 2'-(((6-hydroxy-3-phenanthridinyl)amino)carbonyl)[1,1'-biphenyl]-2-carboxylic acid, Dispiro[1H-perimidine-2 (3H), 1'-cyclohexane-4',2(3H)-[1H]perimidine], N-(3-phenylphenyl)-N',N'-dipiperazin-5-yl-piperazine-1,4-dicarboxamide, (2R)-5-phenyl-2-[(2R)-5-phenyl-2,3-dihydro-1,3-benzoxazol-2-yl]-2,3-dihydro-1,3-benzoxazole, 2-((4bS,7aS,8aR,13S,13aR,13bS)-1-nitro-2,3-dioxo-2,3,5,6,7a,8,8a,11,13,13a,13b,14-dodecahydro-7,9-methanooxepino[3,4-a]pyrrolo[2,3-d] carbazol-13-yl)acetic acid, 3-Chloro-N-(2-((2-methyl-1, 2,3,4-tetrahydroisoquinolin-1-yl)methyl)phenyl)benzo[b] thiophene-2-carboxamide, (2S)-5-phenyl-2-[(2S)-5-phenyl-2,3-dihydro-1,3-benzoxazol-2-yl]-2,3-dihydro-1, 3-benzoxazole, 2,3-Dihydro-4-nitro-2,3-dioxo-9,10-secostrychnidin-10-oic acid (cacotheline), Piperidin-2-yl{2-(trifluoromethyl)-6-[4-(trifluoromethyl)phenyl] pyridin-4-yl}methanol, N-(4-bromo-1-naphthyl)-1-hydroxy-2-naphthamide, 6,6'-methylenebis[1,2-dihydro-2,2,4-trimethyl]-Quinoline, 4-[(1-methyl-6-nitroquinolin-4-ylidene)amino]-N-[4-[(1-methylpyridin-4-ylidene) amino]phenyl]benzamide, or (5R,5aR,8aR,9S)-5,8,8a,9-Tetrahydro-5-(4-hydroxy-3,5-dimethoxyphenyl)-9-({4,6-O—[(R)-2-thienylmethylene]-β-D-glucopyranosyl}oxy) furo[3',4':6,7]naphtho[2,3-d]-1,3-dioxol-6(5aH)-one, Dispiro[1H-perimidine-2(3H), 1-cyclohexane-4',2(3H)-[1H]perimidine]2-phenyl-3-[4-[4-(3-phenylquinoxalin-2-yl)phenyl]sulfanylphenyl]quinoxaline 1-N,4-N-bis(3-phenylphenyl)piperazine-1,4-dicarboxamide (2S)-5-phenyl-2-[(2S)-5-phenyl-2,3-dihydro-1,3-benzoxazol-2-yl]-2,3-dihydro-1,3-benzoxazole (2R)-5-phenyl-2-[(2S)-5-phenyl-2,3-dihydro-1,3-benzoxazol-2-yl]-2,3-dihydro-1,3-benzoxazole 2-[2-[(6-oxo-5H-phenanthridin-3-yl) carbamoyl]phenyl]benzoate dimethylBLAHol (2R)-5-phenyl-2-[(2R)-5-phenyl-2,3-dihydro-1,3-benzoxazol-2-yl]-2,3-dihydro-1,3-benzoxazole 2,2'-spirobi[3,6,7,8-tetrahydro-1H-cyclopenta[g]naphthalene]-5,5'-dione 1,5- diphenoxyanthracene-9,10-dione 2-[4-[4-(1,3-dioxo-2-azaspiro[4.4]nonan-2-yl)-3-methylphenyl]-2-methylphenyl]-2-azaspiro[4.4]nonane-1,3-dione (4aR,5aS,8aS,13aS,15aR,15bR)-6-oxido-4a,5,5a,7,8,13a,15,15a,15b,16-decahydro-2H-4,6-methanoindolo[3,2,1-ij]oxepino[2,3,4-de]pyrrolo[2,3-h]quinoline-6-ium-14-one 2,3-(4',3'-Pyrazolo)pregna-4,6-dien-20-one, 11.beta.,17-dihydroxy-6,16.alpha.-dimethyl-2'-phenyl-; Ketone, 1,2,3,3a,3b,7,10,10a,10b,11,12,12a-dodecahydro-1,11-dihydroxy-2,5,10a,12a-tetramethyl-7-phenylcyclopenta[7,8]phenanthro[2,3-c]pyrazol-1-yl methyl 1-N,4-N-bis[3-(1H-benzimidazol-2-yl)phenyl]benzene-1,4-dicarboxamide 1-(benzotriazol-1-yl)anthracene-9,10-dione 2-chloro-6-[(2-chloro-4-methylquinolin-6-yl)methyl]-4-methylquinoline 6-(1,3-dihydrophenanthro[9,10-d]imidazol-2-ylidene)cyclohexa-2,4-dien-1-one (3R,5S,8S,9S,10R,13S,14S,17R)-10,13-dimethyl-17-[3-(trifluoromethyl)-1H-pyrazol-5-yl]-2,3,4,5,6,7,8,9,11,12,14,15,16,17-tetradecahydro-1H-cyclopenta[a]phenanthren-3-ol 5-(anthracen-1-ylmethylidene)-2-sulfanylidene-1,3-diazinane-4,6-dione N-hydroxy-3-[4-(4-methylphenyl)-2,3-dihydro-1,5-benzothiazepin-2-yl]benzeneamine oxide 3-(4,5-dimethylbenzo[h][1,6]naphthyridin-1-ium-2-yl)-2-methylquinolin-4-amine N-hydroxy-3-[4-(4-methylphenyl)-2,3-dihydro-1,5-benzothiazepin-2-yl]benzeneamine oxide 2-[2-[(9-ethylcarbazol-3-yl)carbamoyl]phenyl]benzoate 1,8-bis(phenylsulfanyl)anthracene-9,10-dione methyl(1S,15S,17S,18S,19S,20S)-17-(4-aminobenzoyl)oxy-6,18-dimethoxy-3,11,12,13,14,15,16,17,18,19,20,21-dodecahydro-1H-yohimban-13-ium-19-carboxylate 2,3-(4',3'-Pyrazolo)pregna-4,6-dien-20-one, 11.beta.,17-dihydroxy-6,16.alpha.-dimethyl-2'-phenyl-; Ketone, 1,2,3,3a,3b,7,10,10a,10b,11,12,12a-dodecahydro-1,11-dihydroxy-2,5,10a,12a-tetramethyl-7-phenylcyclopenta[7,8]phenanthro[2,3-c]pyrazol-1-yl methyl 4-[4-[(N'E)-N'-(2,4-dioxo-1H-quinolin-3-ylidene)hydrazino]-2-methyl-phenyl]azo-N,N-dimethyl-benzamid Chlorobiocin (3S,5S,8S,9S,10R,13S,14S,17R)-10,13-dimethyl-17-[3-(trifluoromethyl)-1H-pyrazol-5-yl]-2,3,4,5,6,7,8,9,11,12,14,15,16,17-tetradecahydro-1H-cyclopenta[a]phenanthren-3-ol 9,10-dioxo-1-phenylsulfanylanthracene-2-carboxylic acid 1-(1,3-benzothiazol-2-yl)-3-[3-(1,3-benzothiazol-2-ylcarbamoylamino)-4-methylphenyl]urea[4-[3,5-bis(trifluoromethyl)phenyl]azo-3,5-dimethyl-pyrazol-1-yl]-(5-methyl-3-phenyl-isoxazol-4-yl)- or their derivatives or pharmaceutically acceptable salts thereof.

Preferably, the compound is cacotheline or pharmaceutically acceptable salts thereof.

In a non exclusive, yet preferred example, the subjects to be treated with the compounds are human or other mammals.

The compounds or pharmaceutically acceptable salts thereof modulate astrocytic release of substances through hemichannels of connexins and pannexins for the treatment of psychiatric disorders.

"Psychiatric disorder" is referred to any mental disorder, mental illness, mental disease, psychiatric or neuropsychiatric disease or illness or disorder, mood disorders, memory-related disorders, psychotic disorders, personality disorders, anxiety disorders, as well as other mental disorders such as substance-abuse-related disorders, childhood disorders, dementia, autistic disorder, adjustment disorder, delirium, multi-infarct dementia, and Tourette's disorder as described in Diagnostic and Statistical Manual of Mental Disorders, Fourth Edition, (DSM IV). Typically, such disorders have a complex genetic and/or a biochemical component.

The psychiatric disorder which can be treated with the use of the compounds that modulate astrocytic release of substances through hemichannels of connexins and pannexins and not affecting gap junctions may be selected, but not limited, from major depression, mania, bipolar disorders, schizophrenia, schizoaffective disorder, schizophreniform disorder, delusional disorder, brief psychotic disorder, and shared psychotic disorder, post traumatic stress disorder, amnesia, anterograde amnesia, blackout (alcohol or drug-related amnesia), childhood amnesia, false memory syndrome, fragmentation of memory, fugue state, hyperthymesia, lacunar amnesia, memory distrust syndrome, memory loss, post traumatic amnesia, prosopamnesia, psychogenic amnesia, repressed memory, retrograde amnesia, selective memory loss, source amnesia, source-monitoring error, transient global amnesia, twilight sleep, obsessive-compulsive disorder, substance-related disorders, childhood disorders, dementia, autistic disorder, adjustment disorder, delirium, and Tourette's disorder, among others.

We also provide a method of treating psychiatric disorders, comprising administering to a mammal or human a therapeutically effective amount of a compound or a pharmaceutically acceptable salt thereof that modulates astrocytic release of substances through connexin and pannexin hemichannels without influencing or disturbing the function of gap junctions.

Preferably, the aforementioned connexin hemichannels correspond to connexin 30 and connexin 43 hemichanels and aforementioned pannexin hemichannels correspond to pannexin 1 hemichanels.

The compounds or pharmaceutically acceptable salts thereof of the method for treating a psychiatric disorder differentially modulate, block, open, inhibit, and/or activate connexin and/or pannexin hemichannels or a combination thereof from astrocytes while not affecting gap junctions directly.

Preferably, the compounds or pharmaceutically acceptable salts thereof of the method for treating a psychiatric disorder of the present invention block or open connexin and/or pannexin hemichannels from astrocytes or a combination thereof.

The compounds or pharmaceutically acceptable salts thereof of the method of treating a psychiatric disorder may be connexin or pannexin mimetic peptides, which relate to peptides that mimic regions of the protein sequence of the target hemichannels, thus affecting their opening probability and physiological activity. In a more preferred embodiment, the compounds or pharmaceutically acceptable salts thereof of the method for treating a psychiatric disorder of the present invention are peptides that correspond to any region of a connexin or a pannexin.

Preferably, the compounds or pharmaceutically acceptable salts thereof of the method of treating a psychiatric disorder of the present invention are peptides that correspond to any region of connexin 43 or connexin 30 or pannexin 1.

More preferably, the compounds or pharmaceutically acceptable salts thereof of the method of treating a psychiatric disorder are peptides that correspond to a region of the cytoplasmic loop of connexin 43 or connexin 30 or pannexin 1.

The compounds or pharmaceutically acceptable salts thereof of the method of treating a psychiatric disorder may be peptides that correspond to a region of any extracellular loop of a connexin or a pannexin. More preferably, the compounds or pharmaceutically acceptable salts thereof of the method of treating a psychiatric disorder are peptides that correspond to a region of any extracellular loop of connexin 43 or connexin 30 or pannexin 1.

The compounds or pharmaceutically acceptable salts thereof of the method of treating a psychiatric disorder may be peptides that correspond to a region of the C-terminal domain of a connexin or a pannexin. More preferably, the compounds or pharmaceutically acceptable salts thereof of the method of treating a psychiatric disorder are peptides that correspond to a region of the c-terminal domain of connexin 43 or connexin 30 or pannexin 1.

The compounds or pharmaceutically acceptable salts thereof of the method of treating a psychiatric disorder may be peptides that interfere with functioning of connexins or pannexins or a combination thereof in their hemichannel configuration.

The compounds or pharmaceutically acceptable salts thereof of the method of treating a psychiatric disorder may be peptides that interfere with functioning of connexin 30 or connexin 43 or pannexin 1 or a combination thereof in their hemichannel configuration.

The compounds or pharmaceutically acceptable salts thereof of the method of treating a psychiatric disorder may be any compound whether natural or artificially synthesized that may specifically affect connexin 43 or connexin 30 or pannexin 1 hemichannels or a combination thereof in the astrocytes without affecting gap junctions.

In one non limiting example, the compound or pharmaceutically acceptable salts thereof of the method of treating a psychiatric disorder is selected between, but not limited to: SEQ ID NO:1, SEQ ID NO:2, SEQ ID NO:3, or SEQ ID NO:4, or pharmaceutically acceptable salts thereof.

Preferably the compounds or pharmaceutically acceptable salts thereof of the method of treating a psychiatric disorder is selected between, but not limited to: SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO: 81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, or SEQ ID NO:115, or pharmaceutically acceptable salts thereof.

Both L- and D-enantiomers of any aminoacid can be comprised in the compounds or pharmaceutically acceptable salts thereof of the method for treating a psychiatric disorder of the present invention.

Compounds or pharmaceutically acceptable salts thereof of the method of treating a psychiatric disorder may also comprise non-genetically encoded amino acids comprising but not limited to β-alanine (b-Ala); 3-aminopropionic acid; 2,3-diaminopropionic acid; 4-aminobutyric acid; 2,3-diaminobutyric acid; α-aminoisobutyric acid; ε-aminohexanoic acid; δ-aminovaleric acid; homoarginine; tbutylalanine; t-butylglycine; 3-carboxylic acid; citrulline; cyclohexylalanine; chlorophenylalanine; homocysteine; methylglycine; ornithine; N-methylisoleucine; methionine sulfoxide; norleucine; 2-naphthylalanine; 4-2-fluorophenylalanine; 3-fluorophenylalanine; 4-fluorophenylalanine; penicillamine; 1,2,3,4-tetrahydroisoquinoline-beta.-2-thienylalanine; N-acetyl lysine; phenylglycine; p-aminophenylalanine; N-methyl valine; homoserine; 3-benzothiazol-2-yl-alanine. They may also comprise amino acid analogs comprising phosphoserine, phosphotyrosine, phosphothreonine, gamma-carboxyglutamate, hydroxyproline, octahydroindole-2-carboxylic acid, hippuric acid, α-methyl-alanine, sarcosine, para-benzoyl-phenylalanine, statine, propargylglycine or any other amino acid known in the art, whether presently or in the future.

The compounds may comprise L-amino acids or retro-inverso D-amino acids or D-amino acids added at the N- or C-terminus of the peptides. The compounds may comprise cyclized/stapled and non-cyclized peptides. The may comprise peptide analogs to those of the template peptide that may have analog properties, which may be non-peptide drugs that are structurally similar to the peptide but may have peptide linkages replaced by —CH2NH—, —CH2S—, —CH=CH— (cis and trans), —COCH2-, —CH2-CH2-, —CH2SO—, —CH(OH)CH2- or other chemical groups. Compounds may also have one or more peptides and may be a part of a larger molecule or protein. Compounds may be peptide-based or non-peptide based compounds. The compounds also comprise one or more peptides fused to a second protein or peptide to generate a fusion protein. These sequences can then be inserted into a second protein or peptide loop to provide three-dimensional structure to the region of the fusion protein.

The compounds or pharmaceutically acceptable salts thereof of the method of treating a psychiatric disorder may comprise any addition of sequences or moieties that facilitate the cell entry of the peptides, crossing the brain blood barrier, or serving as epitope for antibodies.

In one non limiting example, the compound or pharmaceutically acceptable salts thereof of the method of treating a psychiatric disorder is selected between, but not limited to: (2S)-5-phenyl-2-[(2R)-5-phenyl-2,3-dihydro-1,3-benzoxazol-2-yl]-2,3-dihydro-1,3-benzoxazole, 1-N,4-N-bis[3-(1H-benzimidazol-2-yl)phenyl]benzene-1,4-dicarboxamide, (8S,9R,10S,11S,13R,14S,17S)-11-hydroxy-10,13-dimethyl-17-(2-phenyl-1,3-thiazol-4-yl)-1,2,6,7,8,9,11,12,14,15,16,17-dodecahydrocyclopenta[a]phenanthren-3-one, Tricinolone acetophenonide, 3-phenyl-2-[4-[4-(3-phenylquinoxalin-2-yl)phenyl]sulfanylphenyl]-quinoxaline, 2-(nitro-dioxo-BLAHyl)acetic, 2'-(((6-hydroxy-3-phenanthridinyl)amino)carbonyl)[1,1'-biphenyl]-2-carboxylic acid, Dispiro[1H-perimidine-2(3H), 1'-cyclohexane-4',2(3H)-[1H]perimidine], N-(3-phenylphenyl)-N',N'-dipiperazin-5-yl-piperazine-1,4-dicarboxamide, (2R)-5-phenyl-2-[(2R)-5-phenyl-2,3-dihydro-1,3-benzoxazol-2-yl]-2,3-dihydro-1,3- benzoxazole, 2-((4bS,7aS,8aR,13S,13aR,13bS)-1-nitro-2,3-dioxo-2,3,5,6,7a,8,8a,11,13,13a,13b,14-dodecahydro-7,9-methanooxepino[3,4-a]pyrrolo[2,3-d]carbazol-13-yl)acetic acid, 3-Chloro-N-(2-((2-methyl-1,2,3,4-tetrahydroisoquinolin-1-yl)methyl)phenyl)benzo[b]thiophene-2-carboxamide, (2S)-5-phenyl-2-[(2S)-5-phenyl-2,3-dihydro-1,3-benzoxazol-2-yl]-2,3-dihydro-1,3-benzoxazole, 2,3-Dihydro-4-nitro-2,3-dioxo-9,10-secostrychnidin-10-oic acid (cacotheline), Piperidin-2-yl{2-(trifluoromethyl)-6-[4-(trifluoromethyl)phenyl]pyridin-4-yl}methanol, N-(4-bromo-1-naphthyl)-1-hydroxy-2-naphthamide, 6,6'-methylenebis[1,2-dihydro-2,2,4-trimethyl]-Quinoline, 4-[(1-methyl-6-nitroquinolin-4-ylidene)amino]-N-[4-[(1-methylpyridin-4-ylidene)amino]phenyl]benzamide, or (5R,5aR,8aR,9S)-5,8,8a,9-Tetrahydro-5-(4-hydroxy-3,5-dimethoxyphenyl)-9-({4,6-O—[(R)-2-thienylmethylene]-β-D-glucopyranosyl}oxy)furo[3',4':6,7]naphtho[2,3-d]-1,3-dioxol-6(5aH)-one, Dispiro[1H-perimidine-2(3H),1'-cyclohexane-4',2(3H)-[1H]perimidine]2-phenyl-3-[4-[4-(3-phenylquinoxalin-2-yl)phenyl]sulfanylphenyl]quinoxaline 1-N,4-N-bis(3-phenylphenyl)piperazine-1,4-dicarboxamide (2S)-5-phenyl-2-[(2S)-5-phenyl-2,3-dihydro-1,3-benzoxazol-2-yl]-2,3-dihydro-1,3-benzoxazole (2R)-5-phenyl-2-[(2S)-5-phenyl-2,3-dihydro-1,3-benzoxazol-2-yl]-2,3-dihydro-1,3-benzoxazole 2-[2-[(6-oxo-5H-phenanthridin-3-yl)carbamoyl]phenyl]benzoate dimethylBLAHol (2R)-5-phenyl-2-[(2R)-5-phenyl-2,3-dihydro-1,3-benzoxazol-2-yl]-2,3-dihydro-1,3-benzoxazole 2,2'-spirobi[3,6,7,8-tetrahydro-1H-cyclopenta[g]naphthalene]-5,5'-dione 1,5-diphenoxyanthracene-9,10-dione 2-[4-[4-(1,3-dioxo-2-azaspiro[4.4]nonan-2-yl)-3-methylphenyl]-2-methylphenyl]-2-azaspiro[4.4]nonane-1,3-dione (4aR,5aS,8aS,13aS,15aR,15bR)-6-oxido-4a,5,5a,7,8,13a,15,15a,15b,16-decahydro-2H-4,6-methanoindolo[3,2,1-ij]oxepino[2,3,4-de]pyrrolo[2,3-h]quinoline-6-ium-14-one 2,3-(4',3'-Pyrazolo)pregna-4,6-dien-20-one, 11.beta.,17-dihydroxy-6,16.alpha.-dimethyl-2'-phenyl-; Ketone, 1,2,3,3a,3b,7,10,10a,10b,11,12,12a-dodecahydro-1,11-dihydroxy-2,5,10a,12a-tetramethyl-7-phenylcyclopenta[7,8]phenanthro[2,3-c]pyrazol-1-yl methyl 1-N,4-N-bis[3-(1H-benzimidazol-2-yl)phenyl]benzene-1,4-dicarboxamide 1-(benzotriazol-1-yl)anthracene-9,10-dione 2-chloro-6-[(2-chloro-4-methylquinolin-6-yl)methyl]-4-methylquinoline 6-(1,3-dihydrophenanthro[9,10-d]imidazol-2-ylidene)cyclohexa-2,4-dien-1-one (3R,5S,8S,9S,10R,13 S,14S,17R)-10,13-dimethyl-17-[3-(trifluoromethyl)-1H-pyrazol-5-yl]-2,3,4,5,6,7,8,9,11,12,14,15,16,17-tetradecahydro-1H-cyclopenta[a]phenanthren-3-ol 5-(anthracen-1-ylmethylidene)-2-sulfanylidene-1,3-diazinane-4,6-dione N-hydroxy-3-[4-(4-methylphenyl)-2,3-dihydro-1,5-benzothiazepin-2-yl]benzeneamine oxide 3-(4,5-dimethylbenzo[h][1,6]naphthyridin-1-ium-2-yl)-2-methylquinolin-4-amine N-hydroxy-3-[4-(4-methylphenyl)-2,3-dihydro-1,5-benzothiazepin-2-yl]benzeneamine oxide 2-[2-[(9-ethylcarbazol-3-yl)carbamoyl]phenyl]benzoate 1,8-bis(phenylsulfanyl)anthracene-9,10-dione methyl(1S,15 S,17S,18S,19S,20S)-17-(4-aminobenzoyl)oxy-6,18-dimethoxy-3,11,12,13,14,15,16,17,18,19,20,21-dodecahydro-1H-yohimban-13-ium-19-carboxylate 2,3-(4',3'-Pyrazolo)pregna-4,6-dien-20-one, 11.beta.,17-dihydroxy-6,16.alpha.-dimethyl-2'-phenyl-; Ketone, 1,2,3,3a,3b,7,10,10a,10b,11,12,12a-dodecahydro-1,11-dihydroxy-2,5,10a,12a-tetramethyl-7-phenylcyclopenta[7,8]phenanthro[2,3-c]pyrazol-1-yl methyl 4-[4-[(N'E)-N'-(2,4-dioxo-1H-quinolin-3-ylidene)hydrazino]-2-methyl-phenyl]azo-N,N-dimethyl-benzamid Chlorobiocin (3S,5S,8S,9S,10R,13S,14S,17R)-10,13-dimethyl-17-[3-(trifluoromethyl)-1H-pyrazol-5-yl]-2,3,4,5,6,7,8,9,11,12,14,15,16,17-tetradecahydro-1H-cyclopenta[a]phenanthren-3-ol 9,10-dioxo-1-phenylsulfanylanthracene-2-carboxylic acid 1-(1,3-benzothiazol-2-yl)-3-[3-(1,3-benzothiazol-2-ylcarbamoylamino)-4-methylphenyl]urea[4-[3,5-bis(trifluoromethyl)phenyl]azo-3,5-dimethyl-pyrazol-1-yl]-(5-methyl-3-phenyl-isoxazol-4-yl)- or their derivatives or pharmaceutically acceptable salts thereof.

Preferably, the compound or pharmaceutically acceptable salts thereof of the method of treating a psychiatric disorder is cacotheline or pharmaceutically acceptable salts thereof.

In a non exclusive, yet preferred example, the subjects to be treated with the method of treating a psychiatric disorder are human or other mammals.

The compounds or pharmaceutically acceptable salts thereof of the method of treating a psychiatric disorder modulate astrocytic release of substances through hemichannels of connexins and pannexins for the treatment of psychiatric disorders.

We also provide a pharmaceutical composition comprising an effective amount of at least one of the used compounds or pharmaceutically acceptable salts thereof that modulate astrocytic release of substances through hemichannels of connexins and pannexins and not through gap junctions for the treatment of psychiatric disorders in a subject in need thereof and one or more pharmaceutically acceptable carriers, vehicles, additives, excipients, solvents, adjuvants, dyes, flavourings, sweetenings, binders, emollients, fillers, lubricants, preservatives, diluents, thickeners, salts for influencing osmoting pressure, buffers, disintegrants, glidants, wettings, humectants, penetration enhancers for alimentary delivery, microparticulate or nanoparticulate polymeric forms, nanospheres, surface active agents, neutral or cationic lipids, lipid complexes, penetration enhancers comprising oleic acid, capric acid, lauric acid, palmitic acid, stearic acid, myristic acid, linolenic acid, linoleic acid, dicaprate, recinleate, tricaprate, monoolein (a.k.a. 1-monooleoyl-rac-glycerol), caprylic acid, arachidonic acid, dilaurin, acylcholines, glyceryl 1-monocaprate, 1-dodecylazacycloheptan-2-one, acylcarnitines, mono- and di-glycerides and physiologically acceptable salts thereof (i.e., stearate, oleate, caprate, laurate, palmitate, myristate, etc), slow, controlled and targetted release forms, slow, controlled and targetted release parentheral forms, liposomes, and other means to penetrate the blood brain barrier, methods of slow release, nanoparticles or a combination thereof.

In certain examples, controlled release of the compounds of the present invention for parenteral formulations can be made as oily injections, liposomes or as particulate systems, which comprise nanoparticles, microparticles, microspheres, microcapsules, nanospheres, nanocapsules and any slow release systems known in art.

The means to penetrate the blood brain barrier can comprise means such as disruption by osmotic means, the use of vasoactive substances, localized exposure to high-intensity focused ultrasound (HIFU) or magnetic pulses, the use of endogenous transport systems, comprising carrier-mediated transporters such as glucose and amino acid carriers, receptor-mediated transcytosis for insulin or transferrin, the blocking of active efflux transporters such as p-glycoprotein, intracerebral implantation (such as with needles), convection-enhanced distribution, use of mannitol for bypassing the BBB, and use of nanoparticles, liposomes and/or antibodies to transfer substances across the brain blood barrier.

Surgical or medical devices comprising implants may be coated with or may release pharmaceutical compositions of the invention in a variety of manners including for example: (a) by coating the implant or device with a substance such as a hydrogel; (b) by indirectly affixing the compound to the implant or device (e.g. spraying with a polymer or by dipping into a polymer); (c) constructing the implant or device itself with a composition of the compound; or (d) by adapting the implant or device to release the compound.

In certain examples, the compounds or pharmaceutical compositions can be administered orally, nasally, locally, gastrointestinally, intraarterially, intraarterially, into the cerebrospinal fluid, intraperitoneally, into the ventricles, into the spine, or in the form of transdermal patches, ointments, gels, drops, ophthalmic solutions, powders, granules, suspensions, tablets, capsules, in sachets, among others.

The compounds or pharmaceutical compositions differentially modulate, block, open, inhibit, and/or activate connexin and/or pannexin hemichannels or a combination thereof from astrocytes while not affecting gap junctions directly.

Preferably, the aforementioned connexin hemichannels correspond to connexin 30 and connexin 43 hemichannels and aforementioned pannexin hemichannels correspond to pannexin 1 hemichanels.

Preferably, the compounds or pharmaceutical compositions block or open connexin and/or pannexin hemichannels from astrocytes or a combination thereof.

The compounds or pharmaceutical compositions may be connexin or pannexin mimetic peptides, which relate to peptides that mimic regions of the protein sequence of the target hemichannels, thus affecting their opening probability and physiological activity. More preferably, the compounds or pharmaceutical compositions are peptides that correspond to any region of a connexin or a pannexin.

Preferably, the compounds or pharmaceutical compositions are peptides that correspond to any region of connexin 43 or connexin 30 or pannexin 1.

More preferably, the compounds or pharmaceutical compositions are peptides that correspond to a region of the cytoplasmic loop of connexin 43 or connexin 30 or pannexin 1.

The compounds or pharmaceutical compositions may be peptides that correspond to a region of any extracellular loop of a connexin or a pannexin. More preferably, the compounds or pharmaceutical compositions are peptides that correspond to a region of any extracellular loop of connexin 43 or connexin 30 or pannexin 1.

The compounds or pharmaceutical compositions may be peptides that correspond to a region of the C-terminal domain of a connexin or a pannexin. More preferably, the compounds or pharmaceutical compositions are peptides that correspond to a region of the c-terminal domain of connexin 43 or connexin 30 or pannexin 1.

The compounds or pharmaceutical compositions may be peptides that interfere with functioning of connexins or pannexins or a combination thereof in their hemichannel configuration.

The compounds or pharmaceutical compositions may be peptides that interfere with functioning of connexin 30 or connexin 43 or pannexin 1 or a combination thereof in their hemichannel configuration.

The compounds or pharmaceutical compositions may be any compound whether natural or artificially synthesized that may specifically affect connexin 43 or connexin 30 or pannexin 1 hemichannels or a combination thereof in the astrocytes without affecting gap junctions.

In one non limiting example, the compound or pharmaceutical composition is selected between, but not limited to: SEQ ID NO:1, SEQ ID NO:2, SEQ ID NO:3, or SEQ ID NO:4, or pharmaceutically acceptable salts thereof.

Preferably, the compound or pharmaceutical composition is selected between, but not limited to: SEQ ID NO:1, SEQ ID NO:2, SEQ ID NO:3, or SEQ ID NO:4, or pharmaceutically acceptable salts thereof.

Preferably, the compounds or pharmaceutically acceptable salts thereof of the method of treating a psychiatric disorder is selected between, but not limited to: SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO: 81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, or SEQ ID NO:115, or pharmaceutically acceptable salts thereof.

Both L- and D-enantiomers of any aminoacid can be comprised in the compounds or pharmaceutical compositions of the present invention.

Compounds or pharmaceutical compositions may also comprise non-genetically encoded amino acids comprising but not limited to β-alanine (b-Ala); 3-aminopropionic acid; 2,3-diaminopropionic acid; 4-aminobutyric acid; 2,3-diaminobutyric acid; α-aminoisobutyric acid; ε-aminohexanoic acid; δ-aminovaleric acid; homoarginine; tbutylalanine; t-butylglycine; 3-carboxylic acid; citrulline; cyclohexylalanine; chlorophenylalanine; homocysteine; methylglycine; ornithine; N-methylisoleucine; methionine sulfoxide; norleucine; 2-naphthylalanine; 4-2-fluorophenylalanine; 3-fluorophenylalanine; 4-fluorophenylalanine; penicillamine; 1,2,3,4-tetrahydroisoquinoline-beta.-2-thienylalanine; N-acetyl lysine; phenylglycine; p-aminophenylalanine; N-methyl valine; homoserine; 3-benzothiazol-2-yl-alanine. They may also comprise amino acid analogs comprising phosphoserine, phosphotyrosine, phosphothreonine, gamma-carboxyglutamate, hydroxyproline, octahydroindole-2-carboxylic acid, hippuric acid, α-methyl-alanine, sarcosine, para-benzoyl-phenylalanine, statine, propargylglycine or any other amino acid known in the art, whether presently or in the future.

The compounds may comprise L-amino acids or retro-inverso D-amino acids or D-amino acids added at the N- or C-terminus of the peptides. The compounds may comprise cyclized/stapled and non-cyclized peptides. The compounds may comprise peptide analogs to those of the template peptide that may have analog properties, which may be non-peptide drugs that are structurally similar to the peptide but may have peptide linkages replaced by —CH2NH—, —CH2S—, —CH═CH— (cis and trans), —COCH2-, —CH2-CH2-, —CH2SO—, —CH(OH)CH2- or other chemical groups. Compounds may also have one or more peptides and may be a part of a larger molecule or protein. Compounds may be peptide-based or non-peptide based compounds. The compounds also comprise one or more peptides fused to a second protein or peptide to generate a fusion protein. These sequences can then be inserted into a second protein or peptide loop to provide three-dimensional structure to the region of the fusion protein.

The compounds or pharmaceutical compositions may comprise any addition of sequences or moieties that facilitate the cell entry of the peptides, crossing the brain blood barrier, or serving as epitope for antibodies.

In one non limiting example, the compound or pharmaceutical composition is selected between, but not limited to: (2S)-5-phenyl-2-[(2R)-5-phenyl-2,3-dihydro-1,3-benzoxazol-2-yl]-2,3-dihydro-1,3-benzoxazole, 1-N,4-N-bis[3-(1H-benzimidazol-2-yl)phenyl]benzene-1,4-dicarboxamide, (8S,9R,10S,11S,13R,14S,17S)-11-hydroxy-10,13-dimethyl-17-(2-phenyl-1,3-thiazol-4-yl)-1,2,6,7,8,9,11,12,14,15,16,17-dodecahydrocyclopenta[a]phenanthren-3-one, Tricinolone acetophenonide, 3-phenyl-2-[4-[4-(3-phenylquinoxalin-2-yl)phenyl]sulfanylphenyl]-quinoxaline, 2-(nitro-dioxo-BLAHyl)acetic, 2'-(((6-hydroxy-3-phenanthridinyl)amino)carbonyl)[1,1'-biphenyl]-2-carboxylic acid, Dispiro[1H-perimidine-2(3H), 1'-cyclohexane-4',2(3H)-[1H]perimidine], N-(3-phenylphenyl)-N',N'-dipiperazin-5-yl-piperazine-1,4-dicarboxamide, (2R)-5-phenyl-2-[(2R)-5-phenyl-2,3-dihydro-1,3-benzoxazol-2-yl]-2,3-dihydro-1,3-benzoxazole, 2-((4bS,7aS,8aR,13S,13aR,13bS)-1-nitro-2,3-dioxo-2,3,5,6,7a,8,8a,11,13,13a,13b,14-dodecahydro-7,9-methanooxepino[3,4-a]pyrrolo[2,3-d]carbazol-13-yl)acetic acid, 3-Chloro-N-(2-((2-methyl-1,2,3,4-tetrahydroisoquinolin-1-yl)methyl)phenyl)benzo[b]thiophene-2-carboxamide, (2S)-5-phenyl-2-[(2S)-5-phenyl-2,3-dihydro-1,3-benzoxazol-2-yl]-2,3-dihydro-1,3-benzoxazole, 2,3-Dihydro-4-nitro-2,3-dioxo-9,10-secostrychnidin-10-oic acid (cacotheline), Piperidin-2-yl {2-(trifluoromethyl)-6-[4-(trifluoromethyl)phenyl]pyridin-4-yl}methanol, N-(4-bromo-1-naphthyl)-1-hydroxy-2-naphthamide, 6,6'-methylenebis[1,2-dihydro-2,2,4-trimethyl]-Quinoline, 4-[(1-methyl-6-nitroquinolin-4-ylidene)amino]-N-[4-[(1-methylpyridin-4-ylidene) amino]phenyl]benzamide, or (5R,5aR,8aR,9S)-5,8,8a,9-Tetrahydro-5-(4-hydroxy-3,5-dimethoxyphenyl)-9-({4,6-O—[(R)-2-thienylmethylene]-β-D-glucopyranosyl}oxy)furo[3',4':6,7]naphtho[2,3-d]-1,3-dioxol-6(5aH)-one, Dispiro[1H-perimidine-2(3H), 1'-cyclohexane-4',2(3H)-[1H]perimidine]2-phenyl-3-[4-[4-(3-phenylquinoxalin-2-yl)phenyl]sulfanylphenyl]quinoxaline 1-N,4-N-bis(3-phenylphenyl)piperazine-1,4-dicarboxamide (2S)-5-phenyl-2-[(2S)-5-phenyl-2,3-dihydro-1,3-benzoxazol-2-yl]-2,3-dihydro-1,3-benzoxazole (2R)-5-phenyl-2-[(2S)-5-phenyl-2,3-dihydro-1,3-benzoxazol-2-yl]-2,3-dihydro-1,3-benzoxazole 2-[2-[(6-oxo-5H-phenanthridin-3-yl)carbamoyl]phenyl]benzoate dimethylBLAHol (2R)-5-phenyl-2-[(2R)-5-phenyl-2,3-dihydro-1,3-benzoxazol-2-yl]-2,3-dihydro-1,3-benzoxazole 2,2'-spirobi[3,6,7,8-tetrahydro-1H-cyclopenta[g]naphthalene]-5,5'-dione 1,5-diphenoxyanthracene-9,10-dione 2-[4-[4-(1,3-dioxo-2-azaspiro[4.4]nonan-2-yl)-3-methylphenyl]-2-methylphenyl]-2-azaspiro[4.4]nonane-1,3-dione (4aR,5aS,8aS,13aS,15aR,15bR)-6-oxido-4a,5,5a,7,8,13a,15,15a,15b,16-decahydro-2H-4,6-methanoindolo[3,2,1-ij]oxepino[2,3,4-de]pyrrolo[2,3-h]quinoline-6-ium-14-one 2,3-(4',3'-Pyrazolo)pregna-4,6-dien-20-one, 11.beta.,17-dihydroxy-6,16.alpha.-dimethyl-2'-phenyl-; Ketone, 1,2,3,3a,3b,7,10,10a,10b,11,12,12a-dodecahydro-1,11-dihydroxy-2,5,10a,12a-tetramethyl-7-phenylcyclopenta[7,8]phenanthro[2,3-c]pyrazol-1-yl methyl 1-N,4-N-bis[3-(1H-benzimidazol-2-yl)phenyl]benzene-1,4-dicarboxamide 1-(benzotriazol-1-yl)anthracene-9,10-dione 2-chloro-6-[(2-chloro-4-methylquinolin-6-yl)methyl]-4-methylquinoline 6-(1,3-dihydrophenanthro[9,10-d]imidazol-2-ylidene)cyclohexa-2,4-dien-1-one (3R,5S,8S,9S,10R,13S,14S,17R)-10,13-dimethyl-17-[3-(trifluoromethyl)-1H-pyrazol-5-yl]-2,3,4,5,6,7,8,9,11,12,14,15,16,17-tetradecahydro-1H-cyclopenta[a]phenanthren-3-ol 5-(anthracen-1-ylmethylidene)-2-sulfanylidene-1,3-diazinane-4,6-dione N-hydroxy-3-[4-(4-methylphenyl)-2,3-dihydro-1,5-benzothiazepin-2-yl]benzeneamine oxide 3-(4,5-dimethylbenzo[h][1,6]naphthyridin-1-ium-2-yl)-2-methylquinolin-4-amine N-hydroxy-3-[4-(4-methylphenyl)-2,3-dihydro-1,5-benzothiazepin-2-yl]benzeneamine oxide 2-[2-[(9-ethylcarbazol-3-yl)carbamoyl]phenyl]benzoate 1,8-bis(phenylsulfanyl)anthracene-9,10-dione methyl(1S,15S,17S,18S,19S,20S)-17-(4-aminobenzoyl)oxy-6,18-dimethoxy-3,11,12,13,14,15,16,17,18,19,20,21-dodecahydro-1H-yohimban-13-ium-19-carboxylate 2,3-(4',3'-Pyrazolo)pregna-4,6-dien-20-one, 11.beta.,17-dihydroxy-6,16.alpha.-dimethyl-2'-phenyl-; Ketone, 1,2,3,3a,3b,7,10,10a,10b,11,12,12a-dodecahydro-1,11-dihydroxy-2,5,10a,12a-tetramethyl-7-phenylcyclopenta[7,8]phenanthro[2,3-c]pyrazol-1-yl methyl 4-[4-[(N'E)-N'-(2,4-dioxo-1H-quinolin-3-ylidene)hydrazino]-2-methyl-phenyl]azo-N,N-dimethyl-benzamid Chlorobiocin (3S,5S,8S,9S,10R,13S,14S,17R)-10,13-dimethyl-17-[3-(trifluoromethyl)-1H-pyrazol-5-yl]-2,3,4,5,6,7,8,9,11,12,14,15,16,17-tetradecahydro-1H-cyclopenta[a]phenanthren-3-ol 9,10-dioxo-1-phenylsulfanylanthracene-2-carboxylic acid 1-(1,3-benzothiazol-2-yl)-3-[3-(1,3-benzothiazol-2-ylcarbamoylamino)-4-methylphenyl]urea[4-[3,5-bis(trifluoromethyl)phenyl]azo-3,5-dimethyl-pyrazol-1-yl]-(5-methyl-3-phenyl-isoxazol-4-yl)- or their derivatives or pharmaceutically acceptable salts thereof.

Preferably, the compound or pharmaceutical composition is cacotheline or pharmaceutically acceptable salts thereof.

In a non exclusive, yet preferred example, the subjects to be treated with the compounds or pharmaceutical compositions are human or other mammals.

The compounds or pharmaceutical compositions modulate astrocytic release of substances through hemichannels of connexins and pannexins for the treatment of psychiatric disorders.

We also provide a method of screening compounds to treat psychiatric disorders, wherein the compounds modulate astrocytic release of substances through connexin and pannexin hemichannels without influencing or disturbing the function of gap junctions. The method of screening comprises the steps of a) providing test substances; b) selecting the test substances that modulate release of substances through connexin and pannexin hemichannels that do not modulate gap junctions; c) testing the selected test substances in an animal psychiatric disorder model; d) selecting the substances that improve, treat, palliate, cure or reverse the psychiatric disorder.

Preferably, the connexin hemichannels of b) correspond to connexin 30 and connexin 43 hemichanels and pannexin hemichannels of b) correspond to pannexin 1 hemichannels.

The selected substances of the method of screening differentially modulate, block, open, inhibit, and/or activate connexin and/or pannexin hemichannels or a combination thereof from astrocytes while not affecting gap junctions directly.

Preferably, the selected substances of the method of screening block or open connexin and/or pannexin hemichannels from astrocytes or a combination thereof.

The selected substances of the method of screening may be connexin or pannexin mimetic peptides, which relate to peptides that mimic regions of the protein sequence of the target hemichannels, thus affecting their opening probability and physiological activity. Preferably, the selected substances of the method of screening are peptides that correspond to any region of a connexin or a pannexin.

Preferably, the selected substances of the method of screening are peptides that correspond to any region of connexin 43 or connexin 30 or pannexin 1.

More preferably, the selected substances of the method of screening are peptides that correspond to a region of the cytoplasmic loop of connexin 43 or connexin 30 or pannexin 1.

The selected substances of the method of screening may be peptides that correspond to a region of any extracellular loop of a connexin or a pannexin. More preferably, the selected substances of the method of screening are peptides that correspond to a region of any extracellular loop of connexin 43 or connexin 30 or pannexin 1.

The selected substances of the method of screening may be peptides that correspond to a region of the C-terminal domain of a connexin or a pannexin. More preferably, the selected substances of the method of screening are peptides that correspond to a region of the c-terminal domain of connexin 43 or connexin 30 or pannexin 1.

The selected substances of the method of screening may be peptides that interfere with functioning of connexins or pannexins or a combination thereof in their hemichannel configuration.

The selected substances of the method of screening may be peptides that interfere with functioning of connexin 30 or connexin 43 or pannexin 1 or a combination thereof in their hemichannel configuration.

The selected substances of the method of screening may be any compound whether natural or artificially synthesized that may specifically affect connexin 43 or connexin 30 or pannexin 1 hemichannels or a combination thereof in the astrocytes without affecting gap junctions.

In one non limiting example, the selected substance of the method of screening is selected between, but not limited to: SEQ ID NO:1, SEQ ID NO:2, SEQ ID NO:3, or SEQ ID NO:4, or pharmaceutically acceptable salts thereof.

Preferably, the selected substance of the method of screening is selected between, but not limited to: SEQ ID NO:1, SEQ ID NO:2, SEQ ID NO:3, or SEQ ID NO:4, or pharmaceutically acceptable salts thereof.

Preferably, the compounds or pharmaceutically acceptable salts thereof of the method of treating a psychiatric disorder is selected between, but not limited to: SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO: 81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, or SEQ ID NO:115, or pharmaceutically acceptable salts thereof.

Both L- and D-enantiomers of any aminoacid can be comprised in the selected substances of the method of screening.

The selected substances of the method of screening may also comprise non-genetically encoded amino acids comprising but not limited to β-alanine (b-Ala); 3-aminopropionic acid; 2,3-diaminopropionic acid; 4-aminobutyric acid; 2,3-diaminobutyric acid; α-aminoisobutyric acid; ε-aminohexanoic acid; δ-aminovaleric acid; homoarginine; tbutylalanine; t-butylglycine; 3-carboxylic acid; citrulline; cyclohexylalanine; chlorophenylalanine; homocysteine; methylglycine; ornithine; N-methylisoleucine; methionine sulfoxide; norleucine; 2-naphthylalanine; 4-2-fluorophenylalanine; 3-fluorophenylalanine; 4-fluorophenylalanine; penicillamine; 1,2,3,4-tetrahydroisoquinoline-beta.-2-thienylalanine; N-acetyl lysine; phenylglycine; p-aminophenylalanine; N-methyl valine; homoserine; 3-benzothiazol-2-yl-alanine. They may also comprise amino acid analogs comprising phosphoserine, phosphotyrosine, phosphothreonine, gamma-carboxyglutamate, hydroxyproline, octahydroindole-2-carboxylic acid, hippuric acid, α-methyl-alanine, sarcosine, para-benzoyl-phenylalanine, statine, propargylglycine or any other amino acid known in the art, whether presently or in the future.

The compounds may comprise L-amino acids or retroinverso D-amino acids or D-amino acids added at the N- or C-terminus of the peptides. The compounds may comprise cyclized/stapled and non-cyclized peptides. The compounds may comprise peptide analogs to those of the template peptide that may have analog properties, which may be non-peptide drugs structurally similar to the peptide but may have peptide linkages replaced by —CH2NH—, —CH2S—, —CH=CH— (cis and trans), —COCH2-, —CH2-CH2-, —CH2SO—, —CH(OH)CH2- or other chemical groups. Compounds may also have one or more peptides and may be a part of a larger molecule or protein. Compounds may be peptide-based or non-peptide based compounds. The compounds also comprise one or more peptides fused to a second protein or peptide to generate a fusion protein. These sequences can then be inserted into a second protein or peptide loop to provide three-dimensional structure to the region of the fusion protein.

The selected substances of the method of screening may comprise any addition of sequences or moieties that facilitate the cell entry of the peptides, crossing the brain blood barrier, or serving as epitope for antibodies.

In one non limiting example, the selected substance of the method of screening is selected between, but not limited to: (2S)-5-phenyl-2-[(2R)-5-phenyl-2,3-dihydro-1,3-benzoxazol-2-yl]-2,3-dihydro-1,3-benzoxazole, 1-N,4-N-bis[3-(1H-benzimidazol-2-yl)phenyl]benzene-1,4-dicarboxamide, (8S,9R,10S,11S,13R,14S,17S)-11-hydroxy-10,13-dimethyl-17-(2-phenyl-1,3-thiazol-4-yl)-1,2,6,7,8,9,11,12,14,15,16,17-dodecahydrocyclopenta[a]phenanthren-3-one, Tricinolone acetophenonide, 3-phenyl-2-[4-[4-(3-phenylquinoxalin-2-yl)phenyl]sulfanylphenyl]-quinoxaline, 2-(nitro-dioxo-BLAHyl)acetic, 2'-(((6-hydroxy-3-phenanthridinyl)amino)carbonyl)[1,1'-biphenyl]-2-carboxylic acid, Dispiro[1H-perimidine-2(3H), 1'-cyclohexane-4',2(3H)-[1H]perimidine], N-(3-phenylphenyl)-N',N'-dipiperazin-5-yl-piperazine-1,4-dicarboxamide, (2R)-5-phenyl-2-[(2R)-5-phenyl-2,3-dihydro-1,3-benzoxazol-2-yl]-2,3-dihydro-1,3-benzoxazole, 2-((4bS,7aS,8aR,13S,13aR,13bS)-1-nitro-2,3-dioxo-2,3,5,6,7a,8,8a,11,13,13a,13b,14-dodecahydro-7,9-methanooxepino[3,4-a]pyrrolo[2,3-d]carbazol-13-yl)acetic acid, 3-Chloro-N-(2-((2-methyl-1,2,3,4-tetrahydroisoquinolin-1-yl)methyl)phenyl)benzo[b]thiophene-2-carboxamide, (2S)-5-phenyl-2-[(2S)-5-phenyl-2,3-dihydro-1,3-benzoxazol-2-yl]-2,3-dihydro-1,3-benzoxazole, 2,3-Dihydro-4-nitro-2,3-dioxo-9,10-secostrychnidin-10-oic acid (cacotheline), Piperidin-2-yl{2-(trifluoromethyl)-6-[4-(trifluoromethyl)phenyl]pyridin-4-yl}methanol, N-(4-bromo-1-naphthyl)-1-hydroxy-2-naphthamide, 6,6'-methylenebis[1,2-dihydro-2,2,4-trimethyl]-Quinoline, 4-[(1-methyl-6-nitroquinolin-4-ylidene)amino]-N-[4-[(1-methylpyridin-4-ylidene)amino]phenyl]benzamide, or (5R,5aR,8aR,9S)-5,8,8a,9-Tetrahydro-5-(4-hydroxy-3,5-dimethoxyphenyl)-9-({4,6-O—[(R)-2-thienylmethylene]-β-D-glucopyranosyl}oxy)furo[3',4':6,7]naphtho[2,3-d]-1,3-dioxol-6(5aH)-one, Dispiro[1H-perimidine-2(3H), 1'-cyclohexane-4',2(3H)-[1H]perimidine]2-phenyl-3-[4-[4-(3-phenylquinoxalin-2-yl)phenyl]sulfanylphenyl]quinoxaline 1-N,4-N-bis(3-phenylphenyl)piperazine-1,4-dicarboxamide (2S)-5-phenyl-2-[(2S)-5-phenyl-2,3-dihydro-1,3-benzoxazol-2-yl]-2,3-dihydro-1,3-benzoxazole (2R)-5-phenyl-2-[(2S)-5-phenyl-2,3-dihydro-1,3-benzoxazol-2-yl]-2,3-dihydro-1,3-benzoxazole 2-[2-[(6-oxo-5H-phenanthridin-3-yl)carbamoyl]phenyl]benzoate dimethylBLAHol (2R)-5-phenyl-2-[(2R)-5-phenyl-2,3-dihydro-1,3-benzoxazol-2-yl]-2,3-dihydro-1,3-benzoxazole 2,2'-spirobi[3,6,7,8-tetrahydro-1H-cyclopenta[g]naphthalene]-5,5'-dione 1,5-diphenoxyanthracene-9,10-dione 2-[4-[4-(1,3-dioxo-2-azaspiro[4.4]nonan-2-yl)-3-methylphenyl]-2-methylphenyl]-2-azaspiro[4.4]nonane-1,3-dione (4aR,5aS,8aS,13aS,15aR,15bR)-6-oxido-4a,5,5a,7,8,13a,15,15a,15b,16-decahydro-2H-4,6-methanoindolo[3,2,1-ij]oxepino[2,3,4-de]pyrrolo[2,3-h]quinoline-6-ium-14-one 2,3-(4',3'-Pyrazolo)pregna-4,6-dien-20-one, 11.beta.,17-dihydroxy-6,16.alpha.-dimethyl-2'-phenyl-; Ketone, 1,2,3,3a,3b,7,10,10a,10b,11,12,12a-dodecahydro-1,11-dihydroxy-2,5,10a,12a-tetramethyl-7-phenylcyclopenta[7,8]phenanthro[2,3-c]pyrazol-1-yl methyl 1-N,4-N-bis[3-(1H-benzimidazol-2-yl)phenyl]benzene-1,4-dicarboxamide 1-(benzotriazol-1-yl)anthracene-9,10-dione 2-chloro-6-[(2-chloro-4-methylquinolin-6-yl)methyl]-4-methylquinoline 6-(1,3-dihydrophenanthro[9,10-d]imidazol-2-ylidene)cyclohexa-2,4-dien-1-one (3R,5S,8S,9S,10R,13S,14S,17R)-10,13-dimethyl-17-[3-(trifluoromethyl)-1H-pyrazol-5-yl]-2,3,4,5,6,7,8,9,11,12,14,15,16,17-tetradecahydro-1H-cyclopenta[a]phenanthren-3-ol 5-(anthracen-1-ylmethylidene)-2-sulfanylidene-1,3-diazinane-4,6-dione N-hydroxy-3-[4-(4-methylphenyl)-2,3-dihydro-1,5-benzothiazepin-2-yl]benzeneamine oxide 3-(4,5-dimethylbenzo[h][1,6]naphthyridin-1-ium-2-yl)-2-methylquinolin-4-amine N-hydroxy-3-[4-(4-methylphenyl)-2,3-dihydro-1,5-benzothiazepin-2-yl]benzeneamine oxide 2-[2-[(9-ethylcarbazol-3-yl)carbamoyl]phenyl]benzoate 1,8-bis(phenylsulfanyl)anthracene-9,10-dione methyl(1S,15 S,17S,18S,19S,20S)-17-(4-aminobenzoyl)oxy-6,18-dimethoxy-3,11,12,13,14,15,16,17,18,19,20,21-dodecahydro-1H-yohimban-13-ium-19-carboxylate 2,3-(4',3'-Pyrazolo)pregna-4,6-dien-20-one, 11.beta.,17-dihydroxy-6,16.alpha.-dimethyl-2'-phenyl-; Ketone, 1,2,3,3a,3b,7,10,10a,10b,11,12,12a-dodecahydro-1,11-dihydroxy-2,5,10a,12a-tetramethyl-7-phenylcyclopenta[7,8]phenanthro[2,3-c]pyrazol-1-yl methyl 4-[4-[(N'E)-N'-(2,4-dioxo-1H-quinolin-3-ylidene)hydrazino]-2-methyl-phenyl]azo-N,N-dimethyl-benzamid Chlorobiocin (3S,5S,8S,9S,10R,13S,14S,17R)-10,13-dimethyl-17-[3-(trifluoromethyl)-1H-pyrazol-5-yl]-2,3,4,5,6,7,8,9,11,12,14,15,16,17-tetradecahydro-1H-cyclopenta[a]phenanthren-3-ol 9,10-dioxo-1-phenylsulfanylanthracene-2-carboxylic acid 1-(1,3-benzothiazol-2-yl)-3-[3-(1,3-benzothiazol-2-ylcarbamoylamino)-4-methylphenyl]urea[4-[3,5-bis(trifluoromethyl)phenyl]azo-3,5-dimethyl-pyrazol-1-yl]-(5-methyl-3-phenyl-isoxazol-4-yl)- or their derivatives or pharmaceutically acceptable salts thereof.

Preferably, the selected substance of the method of screening is cacotheline or pharmaceutically acceptable salts thereof.

In a non exclusive, yet preferred example, the subjects to be treated with the selected substances of the method of screening are human or other mammals.

We also provide compounds selected with said screening methods of treating psychiatric disorders and modulates release of substances through connexin and pannexin hemichannels amd not through gap junctions.

Preferably, the aforementioned connexin hemichannels correspond to connexin 30 and connexin 43 hemichanels and pannexin hemichannels correspond to pannexin 1 hemichanels.

The compounds selected with the screening method differentially modulate, block, open, inhibit, and/or activate connexin and/or pannexin hemichannels or a combination thereof from astrocytes while not affecting gap junctions directly.

Preferably, the compounds selected with the screening method block or open connexin and/or pannexin hemichannels from astrocytes or a combination thereof.

The selected the compounds selected with the screening method may be connexin or pannexin mimetic peptides, which relate to peptides that mimic regions of the protein sequence of the target hemichannels, thus affecting their opening probability and physiological activity. More preferably, the compounds selected with the screening method are peptides that correspond to any region of a connexin or a pannexin.

Preferably, the compounds selected with the screening method are peptides that correspond to any region of connexin 43 or connexin 30 or pannexin 1.

More preferably, the compounds selected with the screening method are peptides that correspond to a region of the cytoplasmic loop of connexin 43 or connexin 30 or pannexin 1.

The compounds selected with the screening method may be peptides that correspond to a region of any extracellular loop of a connexin or a pannexin. More preferably, the selected substances of the method of screening are peptides that correspond to a region of any extracellular loop of connexin 43 or connexin 30 or pannexin 1.

The compounds selected with the screening method may be peptides that correspond to a region of the C-terminal domain of a connexin or a pannexin. More preferably, the compounds selected with the screening method are peptides that correspond to a region of the c-terminal domain of connexin 43 or connexin 30 or pannexin 1.

The compounds selected with the screening method may be peptides that interfere with functioning of connexins or pannexins or a combination thereof in their hemichannel configuration.

The compounds selected with the screening method may be peptides that interfere with functioning of connexin 30 or connexin 43 or pannexin 1 or a combination thereof in their hemichannel configuration.

The compounds selected with the screening method may be any compound whether natural or artificially synthesized that may specifically affect connexin 43 or connexin 30 or pannexin 1 hemichannels or a combination thereof in the astrocytes without affecting gap junctions.

In one non limiting example, the compound selected with the screening method is selected between, but not limited to: SEQ ID NO:1, SEQ ID NO:2, SEQ ID NO:3, or SEQ ID NO:4, or pharmaceutically acceptable salts thereof.

Preferably, the compound selected with the screening method is selected between, but not limited to: SEQ ID NO:1, SEQ ID NO:2, SEQ ID NO:3, or SEQ ID NO:4, or pharmaceutically acceptable salts thereof.

Preferably, the compounds or pharmaceutically acceptable salts thereof of the method of treating a psychiatric disorder is selected between, but not limited to: SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO: 81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, or SEQ ID NO:115, or pharmaceutically acceptable salts thereof.

Both L- and D-enantiomers of any aminoacid can be comprised in the compounds selected with the screening method.

The compounds selected with the screening method may also comprise non-genetically encoded amino acids comprising but not limited to β-alanine (b-Ala); 3-aminopropionic acid; 2,3-diaminopropionic acid; 4-aminobutyric acid; 2,3-diaminobutyric acid; α-aminoisobutyric acid; ε-aminohexanoic acid; δ-aminovaleric acid; homoarginine; tbutylalanine; t-butylglycine; 3-carboxylic acid; citrulline; cyclohexylalanine; chlorophenylalanine; homocysteine; methylglycine; ornithine; N-methylisoleucine; methionine sulfoxide; norleucine; 2-naphthylalanine; 4-2-fluorophenylalanine; 3-fluorophenylalanine; 4-fluorophenylalanine; penicillamine; 1,2,3,4-tetrahydroisoquinoline-beta.-2-thienylalanine; N-acetyl lysine; phenylglycine; p-aminophenylalanine; N-methyl valine; homoserine; 3-benzothiazol-2-yl-alanine. They may also comprise amino acid analogs comprising phosphoserine, phosphotyrosine, phosphothreonine, gamma-carboxyglutamate, hydroxyproline, octahydroindole-2-carboxylic acid, hippuric acid, α-methyl-alanine, sarcosine, para-benzoyl-phenylalanine, statine, propargylglycine or any other amino acid known in the art, whether presently or in the future.

The compounds may comprise L-amino acids or retro-inverso D-amino acids or D-amino acids added at the N- or C-terminus of the peptides. The compounds may comprise cyclized/stapled and non-cyclized peptides. The compounds may comprise peptide analogs to those of the template peptide that may have analog properties, which may be non-peptide drugs that are structurally similar to the peptide but may have peptide linkages replaced by —CH2NH—, —CH2S—, —CH=CH— (cis and trans), —COCH2-, —CH2-CH2-, —CH2SO—, —CH(OH)CH2- or other chemical groups. Compounds may also have one or more peptides and may be a part of a larger molecule or protein. Compounds may be peptide-based or non-peptide based compounds. The compounds also comprise one or more peptides fused to a second protein or peptide to generate a fusion protein. These sequences can then be inserted into a second protein or peptide loop to provide three-dimensional structure to the region of the fusion protein.

The compounds selected with the screening method may comprise any addition of sequences or moieties that facilitate the cell entry of the peptides, crossing the brain blood barrier, or serving as epitope for antibodies.

In one non limiting example, the compound selected with the screening method is selected between, but not limited to: (2S)-5-phenyl-2-[(2R)-5-phenyl-2,3-dihydro-1,3-benzoxazol-2-yl]-2,3-dihydro-1,3-benzoxazole, 1-N,4-N-bis[3-(1H-benzimidazol-2-yl)phenyl]benzene-1,4-dicarboxamide, (8S,9R,10S,11S,13R,14S,17S)-11-hydroxy-10,13-dimethyl-17-(2-phenyl-1,3-thiazol-4-yl)-1,2,6,7,8,9,11,12,14,15,16,17-dodecahydrocyclopenta[a]phenanthren-3-one, Tricinolone acetophenonide, 3-phenyl-2-[4-[4-(3- phenylquinoxalin-2-yl)phenyl]sulfanylphenyl]-quinoxaline, 2-(nitro-dioxo-BLAHyl)acetic, 2'-(((6-hydroxy-3-phenanthridinyl)amino)carbonyl)[1,1'-biphenyl]-2-carboxylic acid, Dispiro[1H-perimidine-2(3H), 1'-cyclohexane-4',2(3H)-[1H]perimidine], N-(3-phenylphenyl)-N',N'-dipiperazin-5-yl-piperazine-1,4-dicarboxamide, (2R)-5-phenyl-2-[(2R)-5-phenyl-2,3-dihydro-1,3-benzoxazol-2-yl]-2,3-dihydro-1,3-benzoxazole, 2-((4bS,7aS,8aR,13S,13aR,13bS)-1-nitro-2,3-dioxo-2,3,5,6,7a,8,8a,11,13,13a,13b,14-dodecahydro-7,9-methanooxepino[3,4-a]pyrrolo[2,3-d]carbazol-13-yl)acetic acid, 3-Chloro-N-(2-((2-methyl-1,2,3,4-tetrahydroisoquinolin-1-yl)methyl)phenyl)benzo[b]thiophene-2-carboxamide, (2S)-5-phenyl-2-[(2S)-5-phenyl-2,3-dihydro-1,3-benzoxazol-2-yl]-2,3-dihydro-1,3-benzoxazole, 2,3-Dihydro-4-nitro-2,3-dioxo-9,10-secostrychnidin-10-oic acid (cacotheline), Piperidin-2-yl {2-(trifluoromethyl)-6-[4-(trifluoromethyl)phenyl]pyridin-4-yl}methanol, N-(4-bromo-1-naphthyl)-1-hydroxy-2-naphthamide, 6,6'-methylenebis[1,2-dihydro-2,2,4-trimethyl]-Quinoline, 4-[(1-methyl-6-nitroquinolin-4-ylidene)amino]-N-[4-[(1-methylpyridin-4-ylidene)amino]phenyl]benzamide, or (5R,5aR,8aR,9S)-5,8,8a,9-Tetrahydro-5-(4-hydroxy-3,5-dimethoxyphenyl)-9-({4,6-O—[(R)-2-thienylmethylene]-β-D-glucopyranosyl}oxy) furo[3',4':6,7]naphtho[2,3-d]-1,3-dioxol-6(5aH)-one, Dispiro[1H-perimidine-2(3H), 1'-cyclohexane-4',2(3H)-[1H]perimidine]2-phenyl-3-[4-[4-(3-phenylquinoxalin-2-yl)phenyl]sulfanylphenyl]quinoxaline 1-N,4-N-bis(3-phenylphenyl)piperazine-1,4-dicarboxamide (2S)-5-phenyl-2-[(2S)-5-phenyl-2,3-dihydro-1,3-benzoxazol-2-yl]-2,3-dihydro-1,3-benzoxazole (2R)-5-phenyl-2-[(2S)-5-phenyl-2,3-dihydro-1,3-benzoxazol-2-yl]-2,3-dihydro-1,3-benzoxazole 2-[2-[(6-oxo-5H-phenanthridin-3-yl)carbamoyl]phenyl]benzoate dimethylBLAHol (2R)-5-phenyl-2-[(2R)-5-phenyl-2,3-dihydro-1,3-benzoxazol-2-yl]-2,3-dihydro-1,3-benzoxazole 2,2'-spirobi[3,6,7,8-tetrahydro-1H-cyclopenta[g]naphthalene]-5,5'-dione 1,5-diphenoxyanthracene-9,10-dione 2-[4-[4-(1,3-dioxo-2-azaspiro[4.4]nonan-2-yl)-3-methylphenyl]-2-methylphenyl]-2-azaspiro[4.4]nonane-1,3-dione (4aR,5aS,8aS,13aS,15aR,15bR)-6-oxido-4a,5,5a,7,8,13a,15,15a,15b,16-decahydro-2H-4,6-methanoindolo[3,2,1-ij]oxepino[2,3,4-de]pyrrolo[2,3-h]quinoline-6-ium-14-one 2,3-(4',3'-Pyrazolo)pregna-4,6-dien-20-one, 11.beta.,17-dihydroxy-6,16.alpha.-dimethyl-2'-phenyl-; Ketone, 1,2,3,3a,3b,7,10,10a,10b,11,12,12a-dodecahydro-1,11-dihydroxy-2,5,10a,12a-tetramethyl-7-phenylcyclopenta[7,8]phenanthro[2,3-c]pyrazol-1-yl methyl 1-N,4-N-bis[3-(1H-benzimidazol-2-yl)phenyl]benzene-1,4-dicarboxamide 1-(benzotriazol-1-yl)anthracene-9,10-dione 2-chloro-6-[(2-chloro-4-methylquinolin-6-yl)methyl]-4-methylquinoline 6-(1,3-dihydrophenanthro[9,10-d]imidazol-2-ylidene)cyclohexa-2,4-dien-1-one (3R,5S,8S,9S,10R,13S,14S,17R)-10,13-dimethyl-17-[3-(trifluoromethyl)-1H-pyrazol-5-yl]-2,3,4,5,6,7,8,9,11,12,14,15,16,17-tetradecahydro-1H-cyclopenta[a]phenanthren-3-ol 5-(anthracen-1-ylmethylidene)-2-sulfanylidene-1,3-diazinane-4,6-dione N-hydroxy-3-[4-(4-methylphenyl)-2,3-dihydro-1,5-benzothiazepin-2-yl]benzeneamine oxide 3-(4,5-dimethylbenzo[h][1,6]naphthyridin-1-ium-2-yl)-2-methylquinolin-4-amine N-hydroxy-3-[4-(4-methylphenyl)-2,3-dihydro-1,5-benzothiazepin-2-yl]benzeneamine oxide 2-[2-[(9-ethylcarbazol-3-yl)carbamoyl]phenyl]benzoate 1,8-bis(phenylsulfanyl)anthracene-9,10-dione methyl(1S,15S,17S,18S,19S,20S)-17-(4-aminobenzoyl)oxy-6,18-dimethoxy-3,11,12,13,14,15,16,17,18,19,20,21-dodecahydro-1H-yohimban-13-ium-19-carboxylate 2,3-(4',3'-Pyrazolo)pregna-4,6-dien-20-one, 11.beta.,17-dihydroxy-6,16.alpha.-dimethyl-2'-phenyl-; Ketone, 1,2,3,3a,3b,7,10,10a,10b,11,12,12a-dodecahydro-1,11-dihydroxy-2,5,10a,12a-tetramethyl-7-phenylcyclopenta[7,8]phenanthro[2,3-c]pyrazol-1-yl methyl 4-[4-[(N'E)-N'-(2,4-dioxo-1H-quinolin-3-ylidene)hydrazino]-2-methyl-phenyl]azo-N,N-dimethyl-benzamid Chlorobiocin (3S,5S,8S,9S,10R,13S,14S,17R)-10,13-dimethyl-17-[3-(trifluoromethyl)-1H-pyrazol-5-yl]-2,3,4,5,6,7,8,9,11,12,14,15,16,17-tetradecahydro-1H-cyclopenta[a]phenanthren-3-ol 9,10-dioxo-1-phenylsulfanylanthracene-2-carboxylic acid 1-(1,3-benzothiazol-2-yl)-3-[3-(1,3-benzothiazol-2-ylcarbamoylamino)-4-methylphenyl]urea[4-[3,5-bis(trifluoromethyl)phenyl]azo-3,5-dimethyl-pyrazol-1-yl]-(5-methyl-3-phenyl-isoxazol-4-yl)- or their derivatives or pharmaceutically acceptable salts thereof.

Preferably, the compounds selected with the screening method is cacotheline or pharmaceutically acceptable salts thereof.

In a non exclusive, yet preferred example, the subjects to be treated with the compounds selected with the screening method are human or other mammals.

Our compounds and methods will be further described with respect to the following Examples which are not meant to limit the disclosure, but rather to further illustrate the various examples.

(A) Cx43 reactivity (light grey) colocalized with GFAP (dark grey), a marker for astrocytes. Scale bar: 10 μm. Arrows show co-localization. (B) Cx43 (light grey) did not colocalize with a neuronal marker (MAP2, dark grey). Arrows show lack of localization. (C) TAT-Cx43L2 did not affect neuronal synaptic release of ATP (black-right) compared to controls (black-left) or glutamate (grey-right compared to controls, grey left) [n=3]. (D) TAT-Cx43L2 had no effects on astrocyte coupling index (black) compared to control (white) [n=3]. (E) TAT-Cx43L2 had no effect on astrocyte coupling incidence (black) compared to controls (white). [n=3]. (F) TAT-Cx43L2 blocked astrocyte hemichannel activity in control conditions (black-left) compared to controls (white-left), but produced complete inhibition of hemichannel activity (dye uptake) when applied to cells bathed with DCSF (black-right) compared to controls (white-right). [n=3]. (G) Example of hemichannel dye uptake inhibition in astrocytes exposed to DCSF conditions alone (open circles) and together with TAT-Cx43L2 (closed circles).

Figure 2:
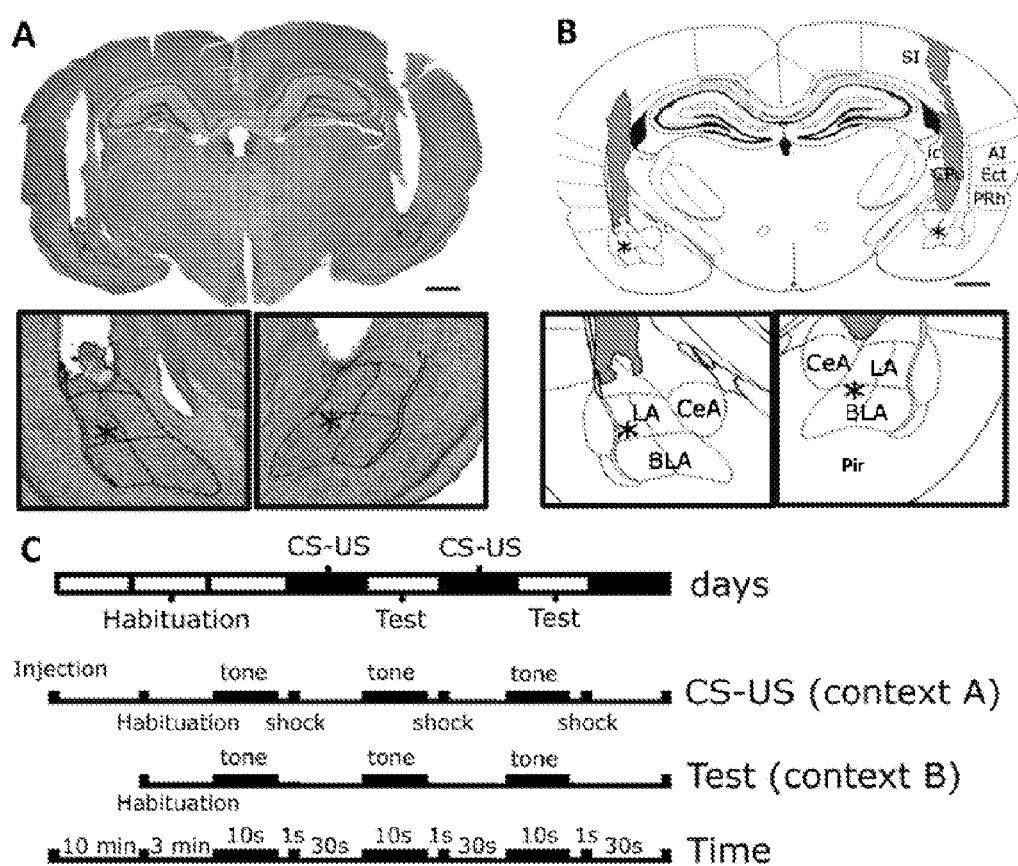

FIG. 2: TAT-Cx43L2 microinfusions into the basolateral amygdala and the fear conditioning paradigm used. (A) Representative photomicrograph of Nissl stained brain slice. Zoomed area shows injection cannula tip 1 mm below end of guide cannula (asterisk). BLA (basolateral amygdala), LA (lateral amygdala) and CeA (central amygdala) borders are shown to ease viewing (dashed line). Scale: 1 mm. (B) Scheme of implant location corresponding to A, showing relevant areas (somatosensory primary (SI), perirhinal (Prh), ectorhinal (Ect), piriform (Pir) and auditory primary (AI) cortices, caudoputamen (Cpu), internal capsula (ic) and external capsula (ec). In zoomed insert, Nissl-based borders of BLA, CeA and LA relative to the location of injection cannula tip (asterisk). Scale: 1 mm. Only successful BLA- LA implants were comprised in the analysis. (C) General experimental protocol for fear conditioning used; each rectangle in the upper scale corresponds to a day. CS-US signifies training and is shown in more detail in the second scale from the top. Test is shown on the third scale from top. Time lapses are shown in bottom scale. Note the change in context between training and test.

Figure 3:
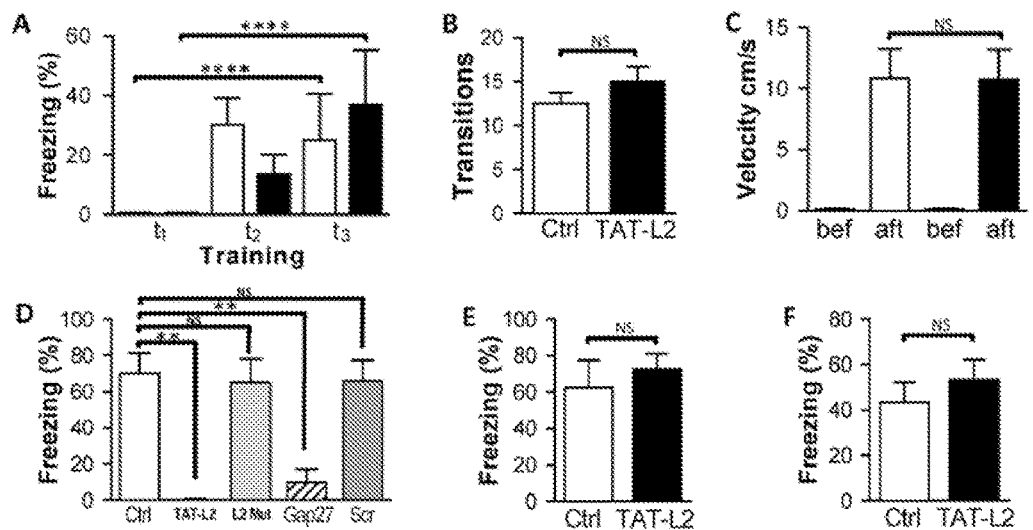

FIG. 3: Peptide effect on auditory fear conditioning task (A) Short term memory was not affected by TAT-Cx43L2 microinfusions (t1, t2 and t3 correspond to subsequent pairings during training) [n=5-6] See control group (white bars) and TAT-Cx43L2 microinfused group (Tat-L2, black bars)
(B) TAT-Cx43L2 did not affect locomotion [n=4-5] as measured by the number of crossings (transitions) in the context along 10 cm$^2$ virtual squares before training. (C) TAT-Cx43L2 did not affect shock reactivity (TAT-L2 (black) versus controls (white) [n=6-4]) as seen by the escape velocity in response to the footshock (before footshock (bef) and after footshock (aft)). (D) Microinfusions of TAT-Cx43L2 (TAT-L2, black) and Gap27 (Gap27, hatched) into the BLA
strongly impaired fear conditioning memory consolidation when tested 24 h after training [n=5-7] compared to control animals (white), while microinfusion of a scrambled Gap27 peptide (Scr, dark grey) or TAT-Cx43L2$^{H126K/I130N}$ peptide (L2 Mut, light grey) had no effects on memory (E) TAT-Cx43L2 had no effects on memory when injected 6 h after training ([n=4-5]. (F) TAT-Cx43L2 microinjected rats recovered their capacity to learn on subsequent training, tested 64 h after the original training [n=4-5].

Figure 4:
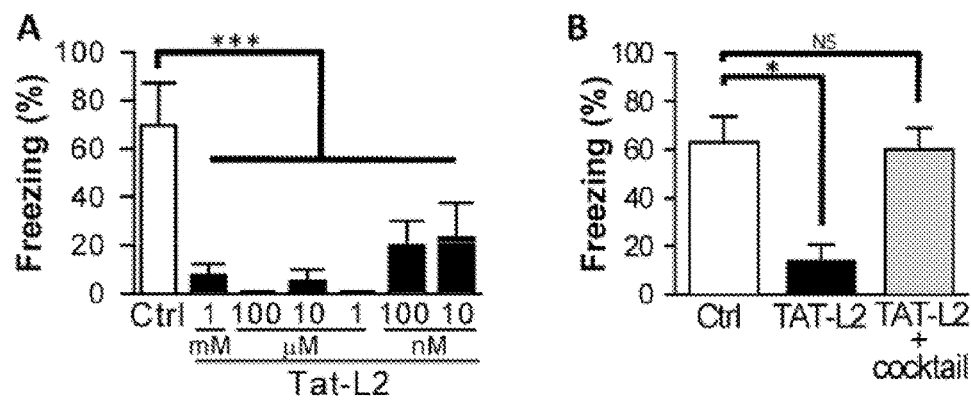

FIG. 4: TAT-Cx43L2 dose response and recovery of learning by co-microinfusion with a cocktail of putative "gliotransmitters". (A) Amnesic effects of TAT-Cx43L2 microinfusions (TAT-L2, black) into the BLA during fear conditioning consolidation [n=5-6] compared to controls (white).
(B) Recovery of learning was obtained after co microinfusion of the lowest dose of TAT-Cx43L2 (10 nM) with a mixture of possible gliotransmitters (cocktail, grey) that comprised D-serine, glutamate, glutamine, glycine, ATP and lactate (grey) [n=5-6].

Figure 5:
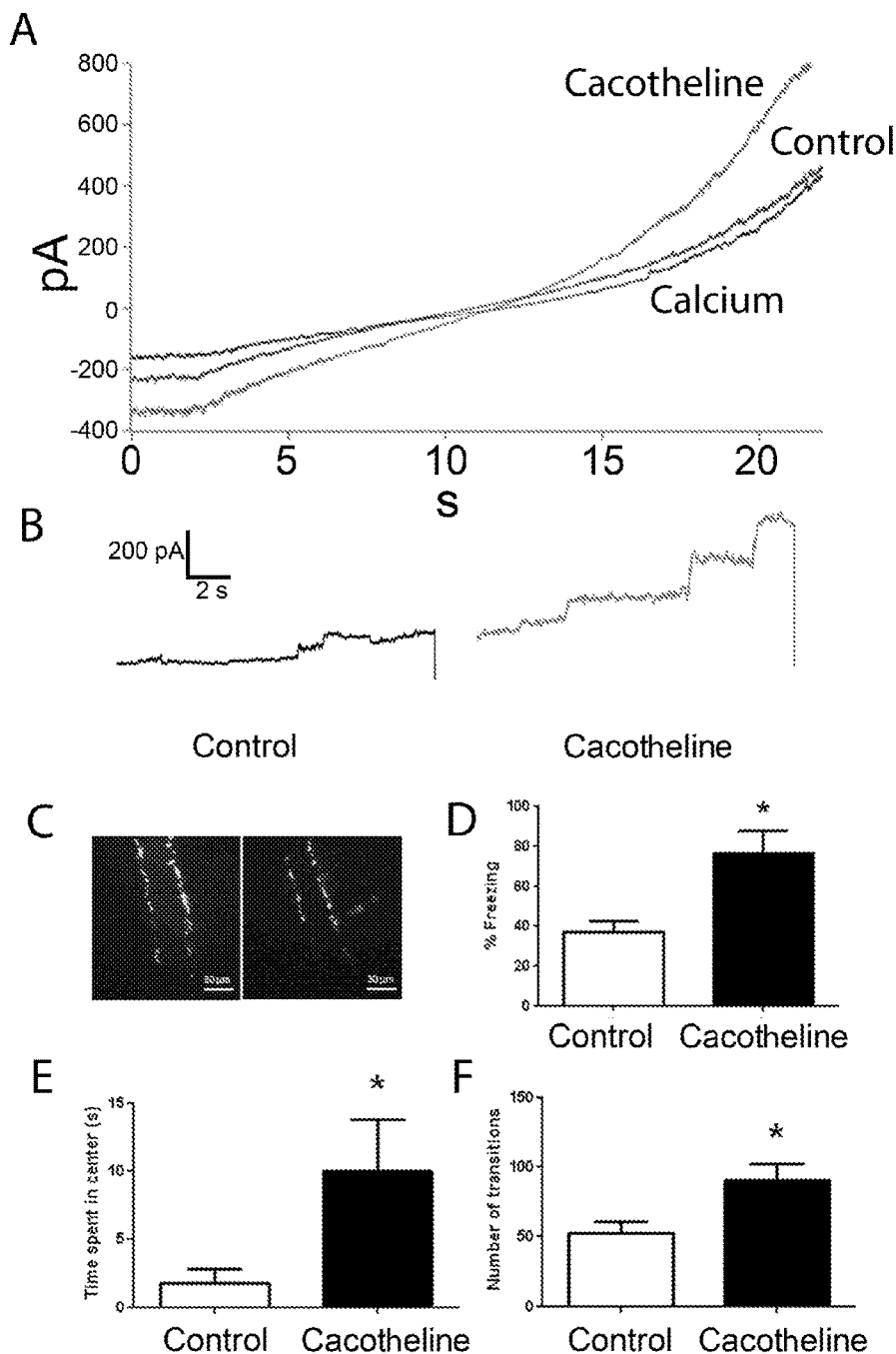

FIG. 5: Cacotheline increases Cx43 hemichannel opening without affecting gap junctions and enhances memory when administered systemically. A. Cacotheline (20 µM) increases Cx43 hemichannel activity in Hela cells transfected to both human and mouse Cx43 as can observed as an increase in conductance in response to a voltage ramp (cacotheline) compared to control cells non-incubated with cacotheline (control). The effects of cacotheline on Cx43 hemichannels were blocked by incubation with high calcium (30 mM) and TAT-Gap19 (100 µM), suggesting a Cx43 hemichannel specific effect. B. Cacotheline increases Cx43 single channel activity as can be observed at +40 mV. C. Cacotheline (right) had no effects on Cx43 gap junctional coupling in Cx43 transfected Hela cells compared to control cells (left). D. Cacotheline administered intravenously 10 minutes before contextual fear conditioning training was able to induce increased freezing to the conditioned context 24 h after training (cacotheline) compared to saline injected controls (control).

Figure 6:
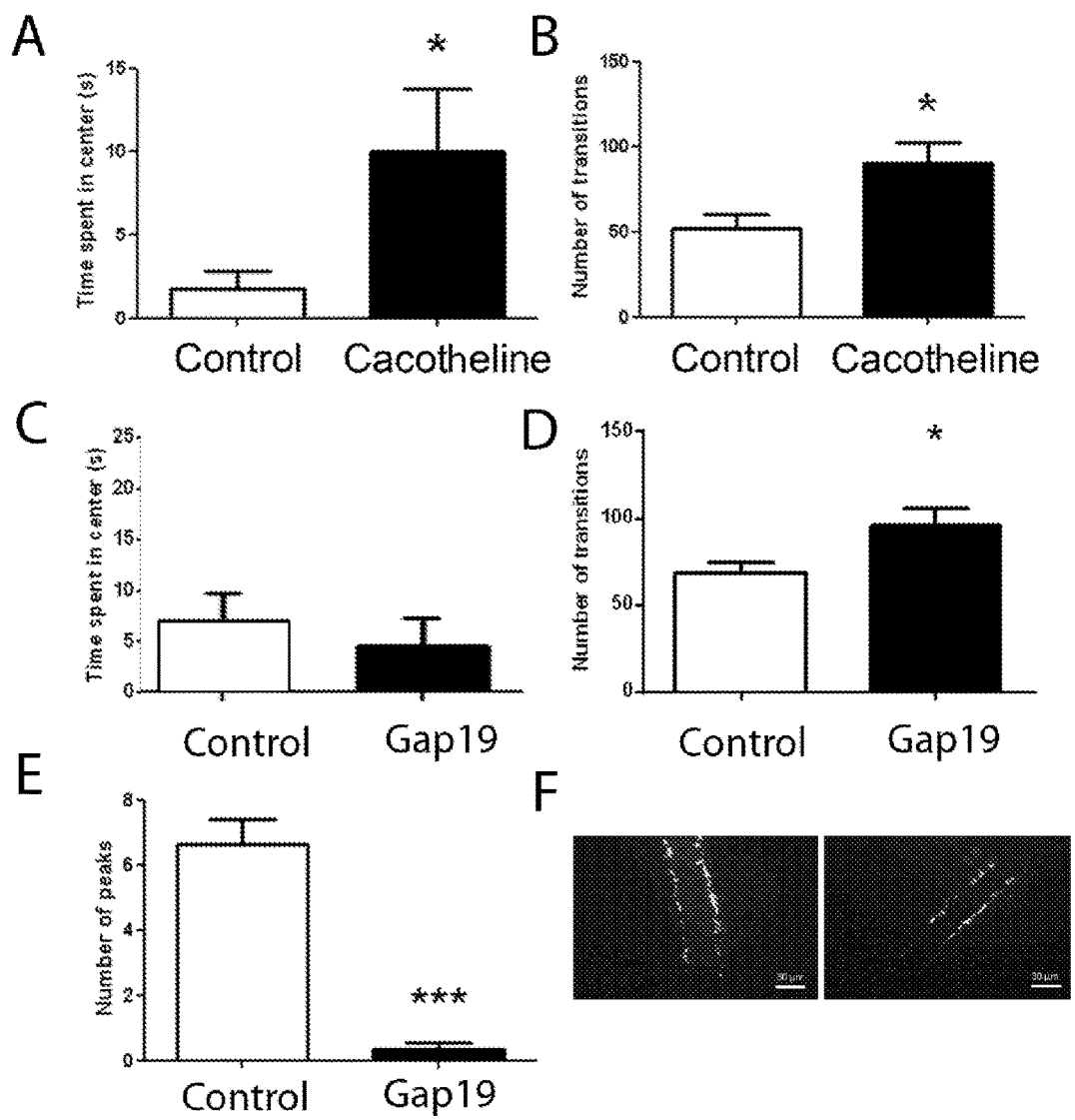

FIG. 6: Cx43 hemichannel modulators had anxiolytic and activating effects. A. Cx43 hemichannel activator cacotheline has anxiolytic effects, inducing an increase in time at the center of the openfield (decreased thigmotaxis) when injected intracranially into the ventral hippocampus (cacotheline) compared to saline injected animals (control) and inducing an increase in locomotion at the openfield when injected intravenously (cacotheline) compared to controls (control). C-E. Cx43 hemichannel blocker TAT-Gap19 peptide induced anxiogenic/activating effects when microinjected into the ventral hippocampus, inducing a tendency to decrease time in the center of the open field (C), increased locomotion in the openfield (D) and decreased peaks in the dark/light test (E). (F) TAT-Gap19 (right) had no effects on Cx43 gap junctional coupling in Cx43 transfected Hela cells compared to control cells (left).

Figure 7:
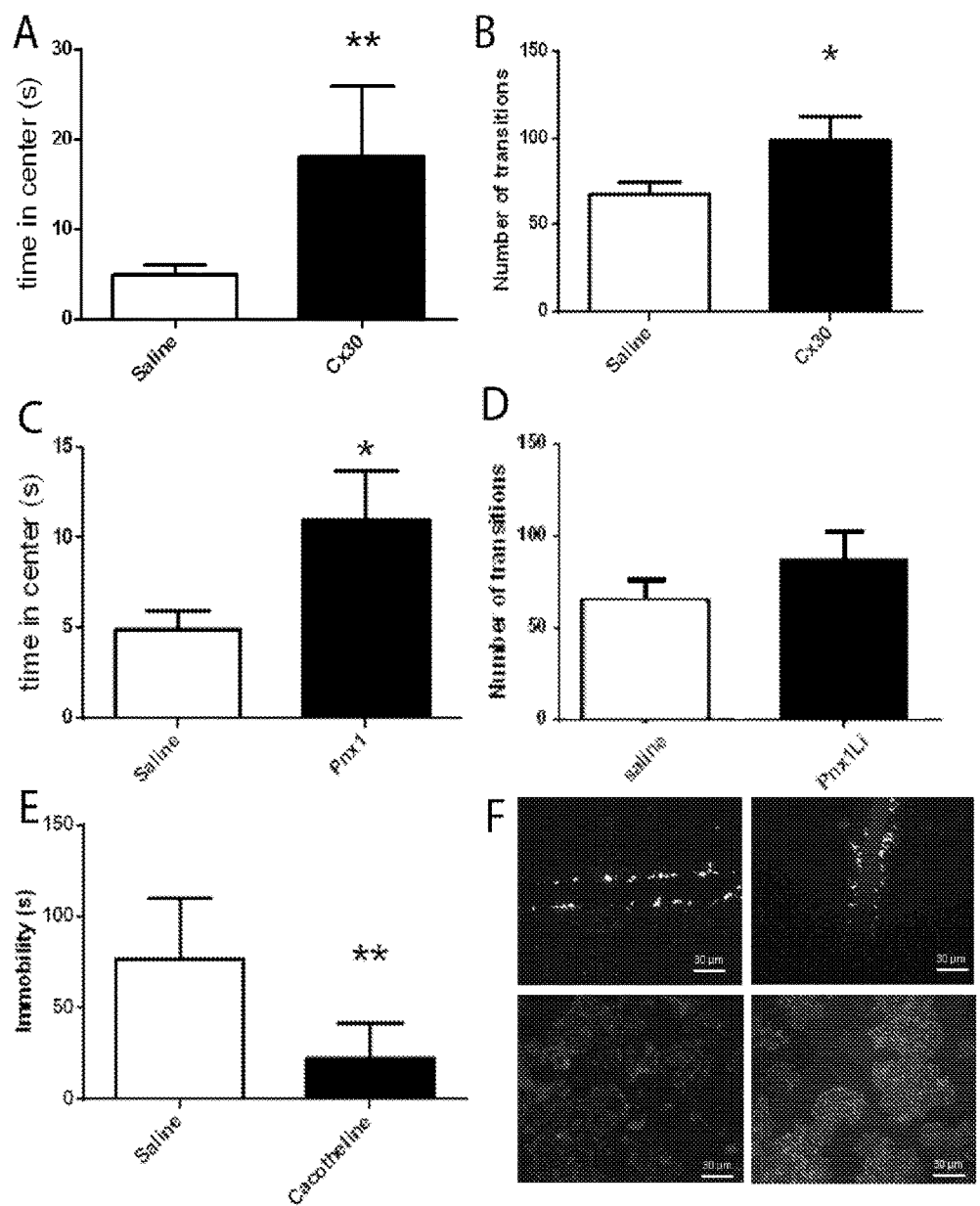

FIG. 7: Cx30 and pannexin 1 (Pnx 1) hemichannel modulators had anxiolytic effects. A-B. Cx30 hemichannel blocker TAT-Cx30 peptide microinjected into the ventral hippocampus had anxiolytic effects, inducing decreased thigmotaxis (A) measured as an increase in time at the center of the openfield (Cx30) compared to saline injected animals (control) and inducing an increase in locomotion at the openfield (B). C-D. Pannexin1 hemichannel blockers Pnx1 and Pnx1Li peptides microinjected into the ventral hippocampus had anxiolytic effects, inducing (C) decreased thigmotaxis measured as an increase in time at the center of the openfield (Pnx1) compared to saline injected animals (control) and (D) increased locomotion at the openfield (TAT-Pnx1L5) compared to saline injected animals (control). (E) Intravenous cacotheline induced a significant decrease in immobility time compared to saline injected rats in the forced swim test (FST), suggesting potential antidepressant effects (F) TAT-Cx30 (upper, right) had no effects on Cx43 gap junctional coupling in Cx43 transfected Hela cells compared to control cells (upper, left) but did induce an increase in Cx30 hemichannel activity (bottom, right) compared to control cells (bottom, left).

DETAILED DESCRIPTION

Examples

The following examples are meant to illustrate, but in no way to limit, this disclosure.

Example 1: Effect of Release of Astrocyte Gliotransmitters on Fear Memory, an Animal Model for Post-Traumatic Stress Disorder (PTSD)

We explored to which extent the release of astrocyte gliotransmitters is necessary for fear memory consolidation at the basolateral amygdala (BLA) in vivo. To this end, we targeted connexin 43 (Cx43) hemichannels found in astrocytes and absent in neurons within the adult central nervous system, as shown using both primary cultures of brain cells[42] and immunohistochemistry in whole tissue[43, 44]. We induced pharmacological blockade of Cx43 hemichannels during learning by using a synthetic peptide corresponding to the Cx43L2 region (aa 119-144), located in the cytoplasmic loop (CL) of Cx43, known as TAT-Cx43L2 (SEQ ID NO: 1). This peptide was previously shown to selectively block Cx43 hemichannels by interfering with loop/tail interactions essential for Cx43-hemichannel activity[23], without affecting Cx43 gap junction channel communication[23, 45].

The Cx43-peptide blockers were found to affect long term memory but not short term memory. The effect of these peptides was only observed when the blocker was applied within the memory consolidation period. Additionally, the loss of memory was transitory and could be recovered after co infusion of putative gliotransmitters known to be released from astrocytes.

A. Animals: All procedures involving animals were in accordance to NIH guidelines and with approval of the bioethical committee of the Universidad Andrés Bello. Sprague Dowley rats (~60 d old, ~250 g) were caged individually at 22° C., 12/12 h light/dark cycle. The rats remained in their home box throughout the study, and were removed only briefly for drug microinfusion.

B. Drugs: TAT-Cx43L2 (YGRKKRRQRRRDGANVDM-HLKQIEIKKFKYGIEEHGK (SEQ ID NO: 1), LifeTein, South Plainfield, N.J., USA, >90% purity) was dissolved in PBS to yield final solutions of 1 mM, 100 μM, 10 μM, 1 μM or 100 nM. Unless stated otherwise, the concentration used for microinfusions of TAT-Cx43L2 was 1 mM. As a control, TAT-Cx43L2$^{H126K/I130N}$ was used at 1 mM. Gap27 (AnaSpec, Fremont, Calif., USA, >95% purity) and Gap27 scramble were dissolved to a final concentration of 1 mM. For the recovery cocktail, 100 mM glutamate (Sigma), D-serine (200 nM), glutamine (100 mM), ATP (100 μM), lactate (10 mM) and glycine (100 nM) were diluted in sterile saline.

C. Apparatus: All behavioral essays were performed in a sound attenuating cubicle. Conditioning and tone testing were conducted in different chambers. For conditioning, rats were placed in a Plexiglas chamber with a metal grid floor (40 cm×40 cm×40 cm). The chamber was dimly illuminated by a red light. For testing, rats were placed in a different Plexiglas chamber without the metal grid (60 cm×40 cm) dimly illuminated by a white light bulb. A video camera was mounted at the top of each chamber to allow digital recording throughout the experiments.

D. Surgery and histology: Under ketamine/xylazine anesthesia (0.02 μl/kg and 0.33 μl/kg, respectively), rats were stereotaxically implanted with bilateral 22-gauge stainless steel cannulas aimed 1.0 mm above the basolateral amygdala (3.0 mm posterior to Bregma, 5.3 mm lateral to the midline, and 8.0 mm ventral to the skull surface (Paxinos, G., Watson, C. (1998). The Rat Brain in Stereotaxic Coordinates; Press A, editor. San Diego). The cannulas were fixed with acrylic dental cement and secured by 4 skull screws. A stylus was placed inside the guide cannula to prevent clogging. Rats were given at least 7 days to recover before experimental procedures began.

In all experiments, stylus was removed from the guide cannula, and a 28-gauge injection cannula was inserted through the guide cannula, extending 1.0 mm beyond its tip into the BLA. Drugs were infused slowly via the injection cannula, connected by PE20 tubing to Hamilton microsyringes driven by a microinfusion pump. Infusions were of 0.25 μl per hemisphere at a rate of 0.32 μl/min. Following drug infusion, injecting cannulaes were left in place for 10 minutes to allow drug diffusion away from the cannula tip. Cannula placement and maximal diffusion was verified by infusing 0.5 μl of India ink in a group of 5 rats. The maximal diffusion spread observed included only lateral and basal amygdala nuclei. At the end of all experiments, animals were anesthetized as above and perfused intracardially with saline, 4% buffered paraformaldehyde. Brains were extracted and postfixed in 30% sucrose until density equaled that of sucrose. The brains were sectioned in a cryostat, Nissl stained (Cresyl violet) and examined with light microscopy for cannula placement and assessment of histological lesions as seen by tissue damage or gliosis. Animals with histological lesions beyond the size of the cannula tip and guide cannula diameter were excluded from the analysis.

E. Behavioral procedures: The conditioning is based on the animal learning that a previously neutral stimulus (a conditioned stimulus, CS; e.g. an innocuous sound) becomes predictive of a stressful stimulus (unconditioned stimulus, US; e.g. footshock). In all of experiments, rats were habituated to handling during the 7 recovery days and also habituated to the training and testing chambers for 3 days, 10 min each day. On the conditioning day, the animals were left in the chamber for 3 minutes before beginning of the training. Each training session consisted of 3 CS-US pairings in 30 s intervals. The CS was an auditory stimulus, 5 kHz, 60 dB, 10 s tone that terminated with a 1.5 mA, 1-sec foot shock (the US). In order to measure the effect of TAT-Cx43L2 on locomotor activity, entire body movements were measured on the training chamber before training began, which were counted as the number of transitions along virtual square subdivisions of 10 cm$^2$ measured offline from the screen of digital video recordings.

To study if TAT-Cx43L2 microinfusions disrupt shock reactivity, rats activity bursts displayed during the 2 s of shock were compared to the activity found 2 s before the shock and were measured as velocity (cm/s). To measure distance entire body movements were analyzed from recordings of the first 2 s from the first footshock of the first training session over virtual subdivisions of 10 cm$^2$ with a chronometer. Then values were converted to real distance in centimeters using known landmark distances from the chamber. Distance was then converted into velocity (cm/s) dividing distance by time. Short term memory (STM) was assessed as an increase in freezing to the tone between the 3 consecutive pairings during training. Long term memory (LTM) was tested 24 h after training. To control for non-specific effects of the drug and to rule out permanent damage to the BLA, rats were retrained 48 h after the LTM test and tested again 24 h later. At the tests rats received the same 10 s tone presentations in the testing chamber, in the same manner as the trainings (5 kHz, 60 dB, 10 s, and every 30 s). In all tests, total seconds of freezing during the CS presentations (immobility) were calculated for each rat and shown as percentage of freezing during the total duration of the tone presentation.

F. Immunohistochemistry: Brain slices previously fixed in buffered 4% paraformaldehyde and maintained in 30% sucrose were mounted in gelatin coated glass slides. After rinsing with PBS, slices were blocked and permeabilized with 1% bovine serum albumin (BSA, Sigma-Aldrich), and 3% Triton X-100 in PBS for 1 h at room temperature. After rinsing again, sections were incubated overnight at 4° C. with the primary anti-Cx43 antibody (Sigma). Afterwards, sections were rinsed with PBS and incubated for 1 h at 37° C. with Alexa Fluor® 488-conjugated secondary antibody. To identify neurons and astrocytes, sections were incubated overnight at 4° C. with either monoclonal anti-MAP2 (M 4402, Sigma-Aldrich, St-Louis, Mo.) for neurons or polyclonal anti-GFAP (Sigma-Aldrich, St-Louis, Mo.) for astrocytes. Sections were washed and incubated for 1 h at 37° C. with Alexa Fluor® 568-conjugated secondary antibodies. Finally, slides were washed and permanently mounted using ProLong® (invitrogen). Staining specificity was assayed by incubation of sections in the absence of the primary antibody. Samples were examined using laser scanning confocal microscopy on a Fluoview FV1000 (Olympus).

G. Primary Cell Cultures:

G.1. Astrocyte cultures: Primary astrocyte cultures were prepared from hippocampus of newborn (PN1) rats. Briefly, the brains were removed, meninges were carefully peeled off, and the hippocampus was dissected. Cells were seeded on glass coverslips (Gassalem, Limeil-Brevannes, France) placed inside 16 mm diameter 24-well plastic plates (Nun- Clon) at a density of 1×10⁵ cells/well in DMEM, supplemented with penicillin (5 U/ml), streptomycin (5 μg/ml), and 10% FCS.

After 8-10 days, when cells had reached confluence, 1 μM of cytosine-arabinoside was added to the culture medium every day for 3 days to eliminate proliferating microglia.

G.2. Neuronal cultures: Hippocampal neurons were obtained from hippocampus of E18 rats. Briefly, hippocampi were dissected as mentioned above for astrocyte cultures. Cells were seeded directly on poly-L-ornithine coated coverslips (1×10⁵ cells/coverslip) in Neurobasal medium supplemented with penicillin (5 U/ml), streptomycin (5 μg/ml), B27 supplement and glutamax. Partial medium changes (¼) were done twice a week.

H. Dye uptake: For single image visualization of dye uptake, astrocytes were bathed in recording solution [in mM: NaCl (148), KCl (5), $CaCl_2$ (1.8), $MgCl_2$ (1), glucose (5), HEPES (5), pH=7.4] containing 5 μM ethidium (Etd) (Sigma-Aldrich, St-Louis, Mo.), and fluorescence intensity was recorded for 10 min in selected cells (ROI, regions of interest). In some experiments astrocytes were exposed to recording solution, but with no added $Ca^{2+}$ and $Mg^{2+}$, and supplemented with 10 mM EGTA (DCFS, divalent cation-free solution) to increase hemichannel opening probability. In all experiments, astrocytes were preincubated for 10 min with TAT-Cx43L2 peptide (100 μM) before dye uptake measurements. Images were captured every 30 s (exposure time=30 ms, gain=0.5) using a Q Imaging model Retiga 13001 fast-cooled monochromatic digital camera (12-bit) (Q imaging, Burnaby, BC, Canada). Metafluor software (version 6.2R5, Universal Imaging Co., Downingtown, Pa., USA) was used for off-line image analysis and fluorescence quantification.

For data representation, the average of two independent background fluorescence intensity measurements (FB, expressed as arbitrary units, AU) was subtracted from the fluorescence intensity in each cell (F1). Results of this calculation (F1-FB) in 20 cells were averaged and plotted vs. time (expressed in minutes). Slopes of dye uptake were calculated using Microsoft Excel software and expressed as AU/min. Microscope and camera settings remained the same in all experiments.

I. Measurement of ATP and glutamate release induced by TAT-Cx43L2: Neurons were plated in multi well culture trays (10⁶ cells/well/0.5 ml) and 48 h later were used for experiments. Extracellular ATP was measured by luciferin/luciferase bioluminescence assay kit (Sigma-Aldrich, St. Louis, Mo., USA). Levels of extracellular glutamate were determined using an enzyme-linked fluorimetric assay as described by Genever & Skerry (Genever, P. G., and Skerry, T. M., 2001, "Regulation of spontaneous glutamate release activity in osteoblastic cells and its role in differentiation and survival: evidence for intrinsic glutamatergic signaling in bone", *FASEB J.* 15, 1586-8). In the presence of glutamate dehydrogenase (GDH) and β-nicotinamide adenine dinucleotide phosphate (NADP⁺), glutamate is oxidized to α-ketoglutarate, yielding NADPH, which can be determined fluorometrically (excitation and emission wavelengths of 355 nm and 460 nm) to provide an indirect quantification of glutamate concentration.

For each assay, standard curves were constructed by using known ATP or glutamate concentrations. The concentrations of ATP and glutamate in samples of extracellular medium were calculated from standard curves and referred to 10⁶ cells). The fraction of ATP or glutamate released by cells to the extracellular milieu was estimated by the difference between the concentration detected in the medium of cells under resting conditions and the concentration measured after stimulation in the presence or absence of hemichannel inhibitors.

J. Dye Coupling: Astrocytes plated on glass coverslips were bathed with recording medium (HCO3-free F-12 medium buffered with 10 mM HEPES, pH 7.2) and intercellular communication mediated by gap junctions was tested by evaluating the transfer to neighboring cells of Lucifer yellow (LY) (Sigma-Aldrich, St-Louis, Mo.) microinjected into one cell. The cultures were observed on an inverted microscope equipped with xenon arc lamp illumination and a Nikon B filter (excitation wavelength 450-490 nm; emission wavelength above 520 nm). LY (10 mM in 150 mM LiCl) was microinjected through a glass microelectrode by brief overcompensation of the negative capacitance circuit in the amplifier to cause oscillations until the impaled cell was brightly fluorescent. Three minutes after dye injection, cells were observed to determine whether dye transfer occurred. The incidence of coupling was scored as the percentage of injections that resulted in dye transfer from the injected cell to more than one neighboring cell. The coupling index was calculated as the mean number of cells to which the dye spread.

K. Data Analysis: Data were expressed as Mean+SD. Statistical differences were assessed by unpaired student's t-test (Mann-Whitney) and by one-way analysis of variance (ANOVA) for multiple comparisons, followed by Dunns post hoc test, and considered significant when $p<0.05$. p-values in the text are written as either <0.01% or <0.05%.

L. Results:

To determine in vivo to which extent the release of astrocyte gliotransmitters is necessary for fear memory consolidation at the basolateral amygdala (BLA) we targeted Cx43 hemichannels, which are found in astrocytes and absent in neurons of the adult central nervous system[42, 44, 46]. To corroborate that Cx43 is present only in astrocytes, BLA slices were immunostained for Cx43 with either astrocytic (GFAP) or neuronal (MAP) markers. Cx43 exclusively co-localized with GFAP, indicating that Cx43 is exclusively present in astrocytes (see FIG. 1A-B).

To test whether gliotransmitter release through astrocytic Cx43 hemichannels is necessary for learning and memory, we induced pharmacological blockade of Cx43 hemichannels during learning by making use of TAT-Cx43L2, a synthetic cell-permeable peptide that corresponds to the Cx43L2 region (aa 119-144) of the cytoplasmic loop (CL) of Cx43; Cx43L2 is known to selectively inhibit Cx43 hemichannels by interfering with loop/tail interactions that are essential for Cx43 hemichannel opening[23, 45]. To rule out direct effects of the peptide on neurons and neuronal synaptic activity, we tested the peptide (1 mM) in hippocampal primary neuronal cultures without astrocytes. TAT-Cx43L2 did not affect ATP or glutamate release in neuronal cultures (see FIG. 1C, in concentrations of pmol/10⁶ cells). Since astroglial coupling is mainly mediated by Cx43 gap junction channels, we studied the effects of TAT-Cx43L2 on gap junctional astroglial communication. For this, hippocampal astroglial cultures were incubated with TAT-Cx43L2 (1 mM) for 10 min and then astroglial coupling was assessed by intracellular transfer of LY microinjected into single cells while monitoring its diffusion to neighbouring cells. Notably, TAT-Cx43L2 did not affect astroglial coupling (see FIG. 1D-E).

Figure 1:
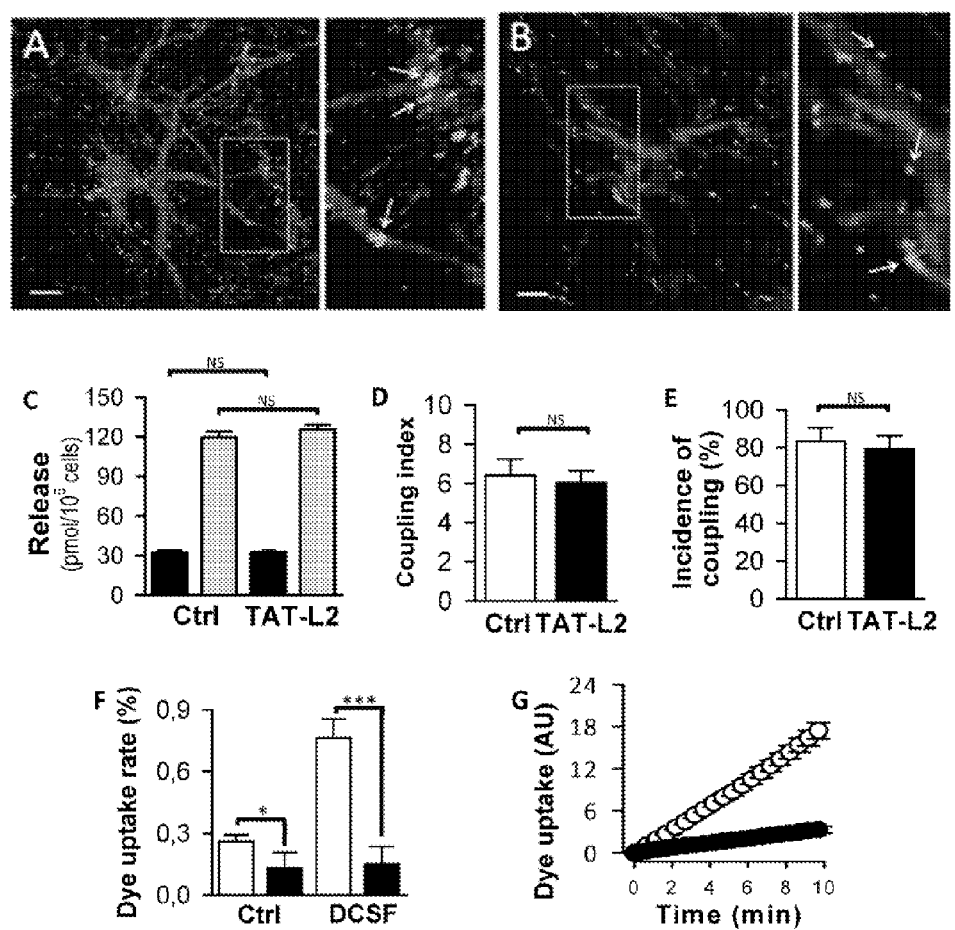
FIG. 1: Cx43 in astrocytes but not in neurons in the BLA and TAT-Cx43L2 inhibiting properties.

To demonstrate the inhibitory properties of TAT-Cx43L2 on astroglial hemichannels, cells were incubated for 10 min with TAT-Cx43L2 (1 mM) and then hemichannel activity was evaluated using the ethidium (Etd) uptake assay in control conditions or after the exposure to divalent cation-free solution (DCFS) known to increase the open probability of Cx hemichannels[47]. As expected TAT-Cx43L2 inhibited hemichannel activity in astrocytes under control conditions (see FIG. 1 F, Ctl) and in astrocytes bathed with DCFS, reduced Etd uptake to the same level as in control cells (FIG. 1F-G). TAT-Cx43L2 inhibited hemichannel activity to levels comparable to those reported after incubation with $La^{3+}$ [48] a widely used Cx-hemichannel blocker[49]. In conclusion, TAT-Cx43L2 inhibited Cx43 hemichannel activity, while maintaining Cx43 gap junction-dependent inter-astrocyte communication or synaptic release unaffected.

To test whether Cx43 hemichannel activity is required for learning and memory, TAT-Cx43L2 (1 mM) was microinjected bilaterally into the BLA in animals previously implanted with chronic injection cannulas (see D. Surgery and histology). All animals included in this study had successful bilateral implants into the BLA and showed no histological lesions beyond the diameter of the injection cannula (see FIG. 2A for a representative Nissl-stained photomicrograph of a representative implant cannula location and FIG. 2B for the respective scheme). The BLA was targeted, since this brain region controls emotional memory associations and is crucial for acquisition of fear conditioning memory[50]. For fear conditioning memory training, animals are trained to associate a tone (10 sec, 5 kHz) with a foot shock. As a consequence, upon hearing the tone in a different context, the animals freeze as a predictive response to the shock (for a general outline of experimental procedures used see FIG. 2C). To potentially interfere with fear memory consolidation but avoid any possible infusion-induced discomfort or stress, and to assess the effects of the drug in locomotion, shock reactivity and short term memory, TAT-Cx43L2 was injected bilaterally into the BLA 10 min before training. In this study, 3 subsequent trainings were used, each every 30 s. FIG. 3A indicates that TAT-Cx43L2 microinfused rats showed unaffected short term memory during training, increasing significantly their freezing to the conditioned tone between the three conditioning trials ($p<0.01$). Injected animals also showed unaffected locomotion (see FIG. 3B) and normal reactivity to the shock (see FIG. 3C). Interestingly, when tested 24 h later in a novel chamber with the tone alone, TAT-Cx43L2 microinjected animals showed complete amnesia, as evident by the lack of freezing during tone presentations (see FIG. 3D, $p<0.01$, $F_{(3,20)}=22.07$). To ensure that the effects of TAT-Cx43L2 are only transient and to rule out a permanent effect of the drug, animals were subsequently retrained in the same setup 48 h after the initial conditioning. Rats previously microinjected with TAT-Cx43L2 recovered their learning capacity (see FIG. 3E).

It is widely accepted that substances that can induce amnesia after learning have no effects on memory if administered 4 hours after the training. Within that 4 hours period known as memory consolidation, stabilization of the short term memory is believed to occur, as it turns into long term memory, a process that requires protein synthesis[50]. To ascertain that TAT-Cx43L2 is affecting specifically memory consolidation, a different group of rats received the peptide microinjection 6 hours after learning, in which case, TAT-Cx43L2 microinjected animals showed no memory deficits (see FIG. 3F).

To further support that the effects of TAT-Cx43L2 were specific to Cx43-hemichannel blockage, TAT-Cx43L2$^{H126K/I130N}$, carrying a mutant L2 sequence in which 2 amino acids essential for binding of L2 to the CT tail of Cx43[23] and inhibition of Cx43 hemichannels[45] were altered and was also microinfused into the BLA.

To further support that the effects of TAT-Cx43L2 were specific for Cx43-hemichannels, a mutant version of the TAT-Cx43L2 peptide, namely TAT-Cx43$^{L2H126K/I130N}$ was microinfused into the BLA. This mutant peptide differs from TAT-Cx43L2 by 2 amino acids that were found to be essential for binding of L2 to the CT tail of Cx43[45]. Furthermore, this TAT-Cx43L2$^{H126K/I130N}$ peptide has been demonstrated to lack the inhibitory properties of TAT-Cx43L2 on Cx43-hemichannel activity[23]. Here, we show that TAT-Cx43L2$^{H126K/I130N}$ microinfusion into the BLA had no effects on memory (see FIG. 3D). To further demonstrate the specificity of Cx43 inhibition we also used Gap27 which is a mimetic peptide of the second extracellular loop of Cx43 hemichannels, previously used to block Cx43 hemichannels when added to the extracellular side[51, 52]. This peptide was microinjected into the BLA with Gap27 (1 mM) 10 minutes before learning. Gap27 microinjected rats showed significant memory deficits compared to control animals (see FIG. 3D, $p<0.01$). Such amnesic effects were comparable to that of the TAT-Cx43L2 peptide. A different group of animals was microinfused with a Gap27 scrambled peptide corresponding to the same amino acids as Gap27 but with a random sequence used to further test the specificity of Cx43 hemichannel inhibition; these experiments convincingly showed no effect on memory (FIG. 3D). Taken together, the above experiments show that blockage of Cx43 hemichannels from either the cytoplasmic or extracellular side, both induce amnesia.

The amnesic effect of Cx43-hemichannel blockage using TAT-Cx43L2 was concentration dependent (FIG. 4A). To determine whether Cx43 hemichannels are involved in memory by allowing gliotransmitter release into the synapse, a lower concentration of TAT-Cx43L2 still capable of inducing amnesic effects (10 nM, $p<0.001$, $F_{(6,29)}=13.9$) was co-injected with a mixture of potential gliotransmitters including glutamate (100 mM), glutamine (100 mM), lactate (10 mM), D-serine (200 nM), glycine and ATP (100 μM). The gliotransmitter "cocktail" was able to reverse TAT-Cx43L2 effects as microinjected rats showed recovery of their capacity to learn (see FIG. 4B, $p<0.05$, $F_{(2,17)}=6.34$), suggesting that gliotransmitter release through Cx43 hemichannels could be necessary for fear memory consolidation.

M. Discussion:

Our results demonstrate that astrocytic Cx43-hemichannel activity is required for fear memory consolidation but not for short term memory in the BLA. This finding is congruent with in vitro studies showing astrocytic release of gliotransmitters being necessary for synaptic plasticity[9]. The amnesic effect of the lowest effective concentration of TAT-Cx43L2 was prevented by co-injection with a mixture of putative gliotransmitters into the BLA, which demonstrates that Cx43 hemichannels mediate the release of some of those substances. This notion is supported by an increasing number of in vitro studies suggesting that gliotransmitter release from astrocytes is necessary for neuronal plasticity, including ATP, glutamate and D-serine[1, 4, 5, 6, 7, 8].

To ensure that blockage is specific for Cx43 hemichannels, two peptides were used; TAT-Cx43L2 and Gap27, designed for blocking Cx43 hemichannels from the cytoplasmic and extracellular sides respectively. To further support specificity for hemichannel blockade, the effect of TAT-Cx43L2 peptide on primary neuronal and astroglial cultures was assessed. TAT-Cx43L2 showed no effects on neurons or neuronal synapses, as incubation with the peptide did not affect ATP and glutamate release. This is congruent with our findings and those of others[42, 43, 44] where Cx43 was found only in astrocytes but not in neurons. On the other hand, previous studies have demonstrated that Gap27 blocks Cx43 hemichannels which are present in astrocytes and absent in neurons[1] and thus, the most conceivable mechanism by which both peptides inhibited memory consolidation is by blockade of Cx43 hemichannels and diminished gliotransmitter release, and not by inhibiting the (vesicular) release of neurotransmitters.

TAT-Cx43L2 peptide also did not affect inter-astrocyte communication,—a process known to be mediated by Cx43 gap junctions—. This result is in line with previous in vitro studies showing TAT-Cx43L2 selectivity for Cx43 hemichannels without affecting inter-astrocyte gap junction transmission[23, 45]. Thus, our in vitro assays showed that TAT-Cx43L2 affected only hemichannel activity, leaving inter-neuronal and inter-astrocyte transmission intact.

Our results demonstrate a crucial role for astrocytic Cx43 hemichannels in fear memory consolidation. Our results show that Cx43-hemichannel activity is necessary for memory consolidation. This supports the idea that neuronal synapses require the release of gliotransmitters from astrocytes to be fully functional. Originally, the idea that synapses are "tripartite" (2 neurons and an astrocyte) was first presented by Araque and his collaborators[38] who suggested that astrocytes release gliotransmitters to modulate neuron to neuron synapses. The release of neuroactive substances from the astrocyte into extracellular space is well documented. These gliotransmitters include glutamate, D-serine, ATP, adenosine, G-amino butyric acid, tumor necrosis factor alpha (TNF-α), prostaglandins, atrial natriuretic peptide and brain-derived neurotrophic factor. Some of these gliotransmitters have been shown to modulate neuronal activity and synaptic plasticity[1, 3, 5, 6, 7, 8]. Here we show that inhibition of Cx43 hemichannel opening induces amnesia in rats without affecting locomotion, shock reactivity or short term memory. This demonstrates that Cx43 hemichannels mediate or contribute to the release of gliotransmitter to the neuronal synapses.

The amnesic effect of the peptide was only observed when the microinfusion was performed during memory consolidation but not 6 h after training.

Given the crucial role for astrocytic Cx43 hemichannels in memory proposed here, Cx43 knockout (KO) mice would be expected to show memory impairments. However, Rash and colleagues[53] reported that Cx43 KO mice tested in the Morris Water maze do not show learning impairments. This unexpected result may be explained by an upregulation of other putative gliotransmitter release mechanisms reported by several in vitro studies which comprise connexin hemichannels, pannexin hemichannels, $P2X_7$ channels, Bestrophin 1 anion channel[54], volume-activated anion channels (VAACs)[55] and vesicle exocytosis[7, 56]. All these mechanisms may normally contribute to functional synapses, and may be upregulated in Cx43 KO mice. In contrast, the acute and short-term hemichannel blockade using TAT-Cx43L2 peptide is less likely to induce significant compensatory effects on other release mechanisms. Cx43 KO mice may also show upregulation of other connexins as well. In that respect, Giaume and colleagues[53] using cultured Cx43 deficient astrocytes showed that co-culture of Cx43 deficient astrocytes with neurons induces the expression of Cx30 and restores gap junctional communication.

Cx30 gap junctions colocalize with most astrocytes expressing Cx43 gap junctions[57, 58] and account for about 20% of hippocampal astrocytic coupling[58]. This means that the gap junctional activity believed to be dependent on Cx43 may be restored in Cx43 deficient astrocytes by the induction of Cx30 gap junctions. Along the same line, it is probable that Cx43 dependent hemichannel activity may be restored by compensatory Cx30 induction or relocation onto synapses.

Moreover, Cx43 KO mice lack both gap junctional channels and hemichannels, thereby complicating the analysis and interpretation of the phenotype. In this respect, conditional Cx43 mouse mutants with functional gap junctional coupling and impaired hemichannel activity may be helpful in establishing the precise in vivo role of Cx43 hemichannels, but have not been reported to date.

All the above may not only explain the lack of memory impairments in Cx43 KO mice, but may also explain the very limited behavioral effects found in Cx43 KO mice by Rash and colleagues[53], including only increased exploration and temporal motor impairments.

The lack of memory impairments and other behavioral effects in Cx43 KO mice, whether due to compensation by other connexins or by upregulation of other putative release mechanisms suggests a redundancy that may reflect on the greater importance of astrocytic release of gliotransmitters into functional synapses required for higher brain function. Further research is needed to decipher the mechanisms by which Cx43 KO mice can still learn spite of lacking Cx43.

Our report is the first to demonstrate that gliotransmitter release from astrocytes through Cx43 hemichannels is crucial for fear memory consolidation and brings forward Cx43 hemichannels in astrocytes as a novel pharmacological target for the treatment of psychiatric disorders, particularly for memory-related disorders like PTSD.

Example 2

Use of non-peptide compounds that modulate Cx43 to affect context fear conditioning memory Cacotheline (2,3-Dihydro-4-nitro-2,3-dioxo-9,10-secostrychnidin-10-oic acid), together with a number of other compounds, were found to increase Cx43 hemichannel activity (FIG. 5 A) without affecting Cx43 gap junctions (FIG. 5 B). Cacotheline was used to affect memory consolidation while being administered systemically (intravenously).

A. Animals: All procedures involving animals were in accordance to NIH guidelines. Sprague Dowley rats (~60 d old, ~250 g) were caged individually at 22° C., 12/12 h light/dark cycle. The rats remained in their home box throughout the study, and were removed only briefly for drug microinfusions.

B. Drugs: Cacotheline (Pharmeks Ltd. Moscow, Russia) was dissolved in sterile saline to yield a final solution of 10 μM in the blood stream. As a control, only sterile saline injection of equal volume was used. Cacotheline was injected into the caudal vein under 4% isofluorane anesthesia.

C. Apparatus: All behavioral essays were performed in a sound attenuating cubicle. Conditioning and testing were conducted in the same chamber. For conditioning, rats were placed in a Plexiglas chamber with a metal grid floor (40 cm×40 cm×40 cm). The chamber was dimly illuminated by a red light. A video camera was mounted at the top of each chamber to allow digital recording throughout the experiments.

D. Behavioral procedures: The conditioning is based on the animal learning that a previously neutral stimulus (a conditioned stimulus, CS; e.g. a context) becomes predictive of a stressful stimulus (unconditioned stimulus, US; e.g. foot-shock). In all experiments, rats were habituated to handling during the 7 days, 10 min each day. On the conditioning day, the animals were left in the chamber to explore for 3 minutes before beginning the training. Each training session consisted of 3 consecutive 1-sec, 1.5 mA foot shocks (the US) in 30 s intervals and the CS was the context. Short term memory (STM) was defined as an increase in freezing to the tone between the 3 consecutive footshocks during training. Long term memory (LTM) was tested 24 h after training. During the test, total seconds of freezing (immobility) were calculated for each rat when exposed to the conditioned context for 5 minutes without the footshock. Freezing is shown as percentage of freezing during the total duration of the context exposure.

E. Whole Cell Patch Clamp

Hela cells were grown and transfected with human and mouse Cx43 cDNA and whole cell patch clamp technique was used to measure hemichannel currents. A ramp protocol from −80 to +80 mV was used before and after incubation of 20 μM cacotheline. Hela cells previously incubated with cacotheline were then incubated with high extracellular calcium (30 mM) or 100 μM TAT-Gap19 in presence of cacotheline.

F. Dye Uptake

For visualization of dye uptake by captured images, Cx43 transfected Hela cells were exposed to 25 uM EthBr (Invitrogen, Eugene, Oreg.) for 5 min at room temperature. Then, cells were incubated with either HEPES-buffered salt solution containing 140 mM NaCl, 4 mM KCl, 1 mM CaCl2, 1 mM MgCl2, 5 mM glucose, 10 nM HEPES or in calcium free HEPES-buffered salt solution (140 mM NaCl, 4 mM KCl, 5 mM glucose, 10 nM HEPES). Then the test compound was added to both solutions followed by EthBr dissolved to a final 25 uM concentration. Cells are washed and mounted in Fluoromount and examined by epifluorescence.

Gap junction permeability was determined at room temperature using the scrape-loading/dye transfer (SL/DT) technique, Hela cells were incubated with Carboxy-fluorescin (1 mg/ml) in the same Ca2+ free HEPES-buffered salt solution as above, then the test compound was added, followed by scrape-loading, which was performed with a razor blade. After 3 minutes the cells are washed with HEPES-buffered salt solution and mounted in Fluoromount and examined by epifluorescence.

G. Results: Cacotheline was able to increase Cx43 hemichannel activity (FIG. 5 A-B) without affecting Cx43 gap junctional communication (FIG. 5 C) as assessed in transfected Hela cells. In FIG. 5 A, Hela cells when exposed to a increasing voltage ramp show a small hemichannel-mediated increase in conductance (control), which is significantly augmented when Hela cells are exposed to cacotheline, suggesting that cacotheline increases Cx43 hemichannel activity. To ensure that this effect is hemichannel dependent, cacotheline treated cells were also incubated with high extracellular calcium (30 mM), condition that is known to block hemichannel activity. High calcium blocked the cacotheline effects on Cx43 hemichannel activity. To further prove that cacotheline effects are specific to Cx43 hemichannels, Hela cells treated with cacotheline were also co incubated with Cx43 selective hemichannel blocker TAT-Gap19, which effectively blocked cacotheline effects to levels similar to high calcium (FIG. 5 A, TAT-Gap19). Cacotheline effects on Cx43 hemichannels can be observed as an increase in single channel conductance and exemplified in FIG. 5 B. Furthermore, cacotheline effects are shown to be selective to Cx43 hemichannels and not to affect Cx43 gap junction communication (FIG. 5 C), having no effects on gap junctional coupling between Cx43 transfected Hela cells. When administered intravenously 10 minutes before contextual fear conditioning, cacotheline was able to increase freezing 24 h after conditioning (see FIG. 5 D). Given that cacotheline also produced anxiolytic effects as seen in other examples (Example 3), the increase in freezing cannot be attributed to anxiogenic effects and thus could be explained by an increase in fear memory strength.

H. Discussion: Compounds capable of Cx43 hemichannel blockage were able to block memory consolidation in a rodent model for PTSD, indicating that Cx43 hemichannel blockers are good candidates be used to treat PTSD. On the other hand, compounds capable of increasing Cx43 hemichannel activity were able to enhance memory, indicating that they are useful to improve memory in general, in dementia, pseudodementia, amnesia or mild cognitive impairment.

Example 3: Anxiolytic and Anxiogenic Effects of Cx43 Hemichannel Modulators

Here, we explored to which extent Cx43 hemichannel modulators can produce anxiolytic effects. To this end different Cx43 hemichannel modulators were injected into the hippocampus using a protocol reported elsewhere[59], Cx43 is found in astrocytes and absent in neurons within the adult central nervous system, as shown using both primary cultures of brain cells[42] and immunohistochemistry in whole tissue[43, 44]. We evaluated whether the pharmacological increase of Cx43 hemichannel activity by the use of the Cx43 hemichannel activator compound cacotheline, or the pharmacological blockade of Cx43 hemichannels by using the synthetic peptide corresponding to the Cx43L2 region (aa 128-136), located in the cytoplasmic loop (CL) of Cx43, known as GAP-19, can induce anxiolytic effects. Gap19 (SEQ ID NO:3) contains the KKFK sequence (SEQ ID NO: 116) that is known as TAT, a cell-membrane translocation motif that facilitates cellular uptake[60]. The peptide has previously shown to selectively block Cx43 hemichannels by interfering with loop/tail interactions essential for Cx43-hemichannel activity without affecting Cx43 gap junction channel communication or Cx40/pannexin-1 hemichannels[61].

A. Animals: All procedures involving animals were in accordance to NIH guidelines and with approval of the bioethical committee of the Universidad Andrés Bello. Sprague Dowley rats (~60 d old, ~250 g) were caged individually at 22° C., 12/12 h light/dark cycle. The rats remained in their home box throughout the study, and were removed only briefly for drug microinfusions.

B. Drugs: For intra hippocampal microinjections Gap19 (YGRKKRRQRRRKQIEIKKFK (SEQ ID NO: 3), LifeTein, South Plainfield, N.J., USA, >90% purity) was dissolved in PBS to yield a final solution of 100 μM and cacotheline was dissolved in sterile saline to a final concentration of 10 μM. For intravenous injections, cacotheline was dissolved to a final concentration of 10 μM in the blood stream, assuming circulating blood as 7% of body weight. Cacotheline was injected into the caudal vein under 4% isofluorane gas anesthesia. In a control group of rats sterile saline injection of equal volume was injected.

C. Dye uptake: Gap junction permeability was determined at room temperature using the scrape-loading/dye transfer (SL/DT) technique, Hela cells were incubated with Carboxy-fluorescin (1 mg/ml) in the same Ca2+ free HEPES-buffered salt solution as above, then the test compound was added, followed byscrape-loading, which was performed with a razor blade. After 3 minutes the cells are washed with HEPES-buffered salt solution and mounted in Fluoromount and examined by epifluorescence.

D. Apparatus: All behavioral essays were performed in an openfield made of Plexiglas (60 cm×40 cm) or a dark/light exploration box (70×40 cm; light compartment 40×40 cm, dark compartment 30×40 cm), illuminated by a white light bulb. A video camera was mounted at the top of the chamber to allow digital recording throughout the experiments.

E. Surgery and histology: Under ketamine/xylazine anesthesia (0.02 μl/kg and 0.33 μl/kg, respectively), rats were stereotaxically implanted with bilateral 22-gauge stainless steel cannulas aimed 1.0 mm above the ventral hippocampus (5.0 mm posterior to Bregma, 5.0 mm lateral to the midline, and 6.0 mm ventral to the skull surface (Paxinos, G., Watson, C. (1998). The Rat Brain in Stereotaxic Coordinates; Press A, editor, San Diego). The cannulas were fixed with acrylic dental cement and secured by 4 skull screws. A stylus was placed inside the guide cannula to prevent clogging. Rats were given at least 7 days to recover before experimental procedures began.

In all experiments, stylus was removed from the guide cannula, and a 28-gauge injection cannula was inserted through the guide cannula, extending 1.0 mm beyond its tip into the ventral hippocampus. Drugs were infused slowly via the injection cannula, connected by PE20 tubing to Hamilton microsyringes driven by a microinfusion pump. Infusions were of 0.25 μl per hemisphere at a rate of 0.32 μl/min. Following drug infusion, injecting cannulaes were left in place for 10 minutes to allow drug diffusion away from the cannula tip. At the end of all experiments, animals were anesthetized as above and perfused intracardially with saline, 4% buffered paraformaldehyde. Brains were extracted and postfixed in 30% sucrose until density equaled that of sucrose. The brains were sectioned in a cryostat, Nissl stained (Cresyl violet) and examined with light microscopy for cannula placement and assessment of histological lesions as seen by tissue damage or gliosis. Animals with histological lesions beyond the size of the cannula tip and guide cannula diameter were excluded from the analysis.

F. Behavioral procedures: To assess the effects of TAT-Gap19 on locomotor activity, entire body movements were measured in the openfield and counted as the number of crossings (transitions) between virtual square subdivisions of 10 $cm^2$ measured offline from digital video recordings. Measures of anxiety included thigmotaxis, rearing activity in the openfield. Transitions between light and dark compartments, number of times the animal peaked from the dark compartment into the lit compartment, and time spent in the lit compartment were measured in the Dark/light box paradigm[62, 63].

G. Data Analysis: Data were expressed as Mean+SD. Statistical differences were assessed by unpaired student's t-test (Mann-Whitney) and considered significant when $p<0.05$.

H. Results: Cacotheline, a compound capable of increasing Cx43 hemichannel activity without affecting Cx43 gap junction communication induced anxiolytic effects when microinjected into the ventral hippocampus, as assessed in the openfield test. Cacotheline microinjection induced a significant increase in the time spent in the center of the openfield (FIG. 6 A) which was corroborated by an increase in total locomotion (transitions) in the openfield as a result of intravenous (systemic) injection of cacotheline (FIG. 6 B). In contrast, selective Cx43 hemichannel blocker TAT-Gap19 induced anxiogenic effects when microinjected into the ventral hippocampus. In the Dark/light paradigm, TAT-Gap19 showed no significant difference in time spent in the openfield (FIG. 6C), but an increase in locomotor activity in the openfield (FIG. 6D) and decreased number of peaks from the dark compartment into the lit compartment (FIG. 6 E).

I. Discussion: Selective Cx43 hemichannel modulators (peptidergic and non peptidergic) that induced an increase in hemichannel activity showed anxiolytic effects, while those that decreased hemichannel activity had anxiogenic effects. This indicates that selective Cx43 hemichannel modulators are useful as anxiolytic drugs, for the treatment of anxiety disorders and depression, or could be used as potential activators of brain activity in pseudodementia or in pathologies that require an increase in brain activity.

Example 4: Anxiolytic Effects of Compounds that Modulate Cx30 Hemichannels Administered Intracranially Besides Cx43, astrocytes have been reported to express Connexin 30 (Cx30)[53, 64]. In that respect, Giaume and colleagues[47]. Thus we decided to evaluate to which extent Cx30 modulators could also produce anxiolytic effects. To this end Cx30 hemichannel modulators designed, synthesized and injected into the hippocampus. We designed peptides capable of blocking or activating selectively Cx30 hemichannels without affecting Cx30 gap junctions.

A. Methods: We used same methods as in Example 3. Cx30 activator (TAT-Cx30L4; ChinaPeptides Ltd. YGRK-KRRQRRRDAPALYSNLSKKRG (SEQ ID NO: 71)) designed from the first extracellular loop of Cx30 was dissolved in sterile saline to yield a final solution of 100 μM.

B. Dye uptake

For visualization of dye uptake by captured images, Cx30 transfected Hela cells were exposed to 25 uM EthBr (Invitrogen, Eugene, Oreg.) for 5 min at room temperature. Then, cells were incubated with either HEPES-buffered salt solution containing 140 mM NaCl, 4 mM KCl, 1 mM CaCl2, 1 mM MgCl2, 5 mM glucose, 10 nM HEPES or in calcium free HEPES-buffered salt solution (140 mM NaCl, 4 mM KCl, 5 mM glucose, 10 nM HEPES). Then the test compound was added to both solutions followed by EthBr dissolved to a final 25 uM concentration. Cells are washed and mounted in Fluoromount and examined by epifluorescence.

Gap junction permeability was determined at room temperature using the scrape-loading/dye transfer (SL/DT) technique, Hela cells were incubated with Carboxy-fluorescin (1 mg/ml) in the same Ca2+ free HEPES-buffered salt solution as above. Then the test compound was added. Scrape-loading was then performed with a razor blade. After 3 minutes the cells are washed with HEPES-buffered salt solution and mounted in Fluoromount and examined by epifluorescence.

C. Results: The Cx30 hemichannel blocking compound was found to induce anxiolytic effects when microinjected into the ventral hippocampus as measured in the openfield test, producing a statistically significant increase in the time the animals spent in the center (FIG. 7 A) and a tendency to increase locomotion (FIG. 7 B). The compound was able to increase hemichannel activity as assessed in Cx30 transfected Hela cells (FIG. 7 F, bottom panel) leaving Cx30 gap junctional communication unaffected (FIG. 7 F, upper panel)

C. Discussion: Our results show that Cx30 hemichannel activators may induce anxiolytic effects and thus, Cx30 is a target to treat anxiety. This is congruent with Cx43 hemichannel activators, which also showed anxiolytic effects. Very little is known about the role of Cx30 hemichannels in astrocytes. Cx30 gap junctions colocalize with most astrocytes expressing Cx43 gap junctions. In one study using cultured Cx43 deficient astrocytes it was reported that co-culture of Cx43 deficient astrocytes with neurons induces the expression of Cx30 and restores gap junctional communication[57, 58] while Cx30 accounts for about 20% of hippocampal astrocytic coupling[58]. Our results show that both hippocampal astrocytes Cx30 and Cx43 hemichannels have a role in anxiety.

Example 5: Anxiolytic Effects of Compounds that Modulate Pannexin 1 (Pnx-1) Hemichannels Administered Intracranially Pannexin 1 hemichannels have an important role in astrocytic function and death, yet a role for them in psychiatry has not been studied to date. Here we decided to test to which extent pharmacological Pannexin1 hemichannel modulation can have anxiolytic effects.
A. Methods: Same as Example 3.
B. Drugs: Two peptides were used, Pnx1 peptide (WRQAAFVDSY (SEQ ID NO: 32), NeoMPS, S A. Straousburg, France) and mimetic peptide TAT-Pnx1L5 (YGRKKRRQRRRRDLDLRDGP (SEQ ID NO: 51); ChinaPeptides Co., Ltd. Shangai, China), which were dissolved in sterile saline to a final concentration of 100 µM.
C. Results: Pnx1 and Pnx1Li peptides showed anxiolytic effects in the open field, increasing significantly the time in the center of the openfield (FIG. 7 C) and the number of transitions.
D. Discussion: Pannexin 1 blockers have anxiolytic effects, indicating that a drug for treating anxiety can target pannexin 1. It must be noted that pannexins are not expected to form gap junctions (although this notion has been questioned), and pannexin 1 is not found exclusively in astrocytes, unlike Cx43 and Cx30, but has also been found in neurons.

Example 6: Use of Compounds that Modulate Cx43 to Affect Depressive-Like Symptoms Given the anxiolytic effects found after systemic (intravenous) administration of Cacotheline, its effects on depressive-like symptoms were also assessed.
A. Methods: To assess depressive-like symptoms the forced swim test (FST) was employed, which was similar to that described elsewhere[65]. On training, rats were individually placed in a transparent Plexiglas cylinder (30 cm diameter× 60 cm height) filled with water at 25±2° C. for 15 minutes. 24 h later, the animals were placed again in the cylinder for 5 minutes as described before. After initial vigorous swimming activity, swimming attempts normally cease and the animal adopts a characteristic immobile floating posture. Rats were scored for time to reach immobility and total immobility time by a trained observer from offline video recordings. Immobility was defined as the cessation of limb movements.
B. Drugs: Cacotheline was dissolved to a final concentration of 10 µM into the blood stream, assuming circulating blood as 7% of body weight. Cacotheline was injected into the caudal vein under 4% isofluorane gas anesthesia 10 minutes before the behavioural test. In a control group of rats sterile saline injection of equal volume was injected.
C. Results: Systemic administration of cacotheline induced a significant decrease in immobility as assessed in the FST (FIG. 7 E), suggesting possible antidepressant effects.
D. Discussion: A compound capable of increasing Cx43 hemichannel activity was able to decrease immobility in the FST, indication antidepressant effects. These effects are congruent with the anxiolytic effects described above. This implies that Cx43 modulators are useful to treat depression and other mood disorders.

REFERENCES

1. Orellana, J. A., Froger, N., Ezan, P., Jiang, J. X., Bennett, M. V., Naus, C. C., Giaume, C., Sáez, J. C., 2011, "ATP and glutamate released via astroglial connexin 43 hemichannels mediate neuronal death through activation of pannexin 1 hemichannels", *J Neurochem* 118, 826-840.
2. Ye, Z. C., Wyeth, M. S., Baltan-Tekkok, S., and Ransom, B. R., 2003, "Functional hemichannels in astrocytes: a novel mechanism of glutamate release", *J Neurosci.* 1, 3588-96.
3. Huang Y, Grinspan J B, Abrams C K, Scherer S S. Pannexin1 is expressed by neurons and glia but does not form functional gap junctions. Glia 2007; 55:46 56)
4. Perea, G., Navarrete, M., Araque, A., 2009, "Tripartite synapses: astrocytes process and control synaptic information", *Trends Neurosci.* 32, 421-431.
5. Achour, B. S., and Pascual, O., 2010, "Glia: the many ways to modulate synaptic plasticity", *Neurochem Int.* 57, 440-445.
6. Henneberger, C., Papouin, T., Oliet, S. H., and Rusakov, D. A., 2010, "Long-term potentiation depends on release of D-serine from astrocytes", *Nature.* 463, 232-236.
7. Yang, Y., Ge, W., Chen, Y., Zhang, Z., Shen, W., Wu, C., Poo, M., and Duan S., 2003, "Contribution of astrocytes to hippocampal long-term potentiation through release of D-serine", *Proc Natl Acad Sci USA.* 100, 15194-15199.
8. Parpura, V., Scemes, E., and Spray, D. C., 2004, "Mechanisms of glutamate release from astrocytes: gap junction "hemichannels", purinergic receptors and exocytotic release", Neurochem Int. 45 259-64.
9. Gourine, A. V., Kasymov, V., Marina, N., Tang, F., Figueiredo, M. F., Lane, S., Teschemacher, A. G., Spyer, K. M., Deisseroth, K., and Kasparov, S., 2010, "Astrocytes control breathing through pH-dependent release of ATP". *Science* 329, 571-575.
10. Bonansco, C., Couve, A., Perea, G., Ferradas, C. Á., Roncagliolo, M., and Fuenzalida, M., 2011, "Glutamate released spontaneously from astrocytes sets the threshold for synaptic plasticity", *Eur J Neurosci.* 33, 1483-92.
11. Domingues, A. M., Taylor, M., and Fern, R., 2010, "Glia as transmitter sources and sensors in health and disease", *Neurochem Int.* 57, 359-366.
12. Samoilova, M, Wentlandt, K, Adamchik, Y, Velumian, A A, Carlen, P L, 2008, "Connexin 43 mimetic peptides inhibit spontaneous epileptiform activity in organotypic hippocampal slice cultures", Exp Neurol. 2008 April; 210(2):762-75.
13. Danesh-Meyer, H V, Kerr, N M, Zhang, J, Eady, E K, O'Carroll, S J, Nicholson, L F, Johnson, C S, Green, C R. 2012, "Connexin43 mimetic peptide reduces vascular leak and retinal ganglion cell death following retinal ischaemia", Brain 2012: 135; 506-520.
14. Thompson, R J, Jackson, M F, Olah, M E, Rungta, R L, Hines, D J, Beazely, M A, MacDonald, J F, MacVicar B A, 2008, "Activation of Pannexin-1 Hemichannels Augments Aberrant Bursting in the Hippocampus", Science. 2008 Dec. 5; 322(5907):1555-9.
15. Orellana, J A, Sáez, P J, Shoji, K F, Schalper, K A, Palacios-Prado, N, Velarde, V, Giaume, C, Bennett, M V, Sáez, J C, 2009, "Modulation of Brain Hemichannels and Gap Junction Channels by Pro-Inflammatory Agents and Their Possible Role in Neurodegeneration", Antioxid Redox Signal. 2009 February; 11(2):369-99.
16. Kawasaki, A, Hayashi, T, Nakachi, K, Trosko, J E, Sugihara, K, Kotake, Y, Ohta, S,2009, "Modulation of connexin 43 in rotenone-induced model of Parkinson's disease", Neuroscience 160 (2009) 61-68.
17. Behrens, C J, Ul Haq, R, Liotta, A, Anderson, M L, Heinemann, U, 2011, "Nonspecific effects of the gap junction blocker mefloquine on fast hippocampal network oscillations in the adult rat in vitro", Neuroscience. 2011 Sep. 29; 192:11-9.
18. Mitterauer, B J, 2010, "The syncytiopathy hypothesis of depression: Downregulation of glial connexins may protract synaptic information processing and cause memory impairment", Medical Hypotheses 74 (2010) 497-502.
19. Desplantez, T, Verma, V, Leybaert, L, Evans, W H, Weingart, R,2012, "Gap26, a connexin mimetic peptide, inhibits currents carried by connexin43 hemichannels and gap junction channels", Pharmacol Res. 2012 May; 65(5): 546-52.
20. Davidson, J O, Green, C R, Nicholson, L F, O'Carroll, S J, Fraser, M, Bennet, L, Gunn, A J. 2012, "Connexin hemichannel blockade improves outcomes in a model of fetal ischemia", Ann Neurol. 2012 January; 71(1):121-32.
21. Sun, J D, Liu, Y, Yuan, Y H, Li J, Chen, N H, 2012, "Gap junction dysfunction in the prefrontal cortex induces depressive-like behaviors in rats", Neuropsychopharmacology. 2012 April; 37(5):1305-20.
22. O'Carroll, S J, Alkadhi, M, Nicholson, L F, Green, C R,2008, "Connexin 43 mimetic peptides reduce swelling, astrogliosis, and neuronal cell death after spinal, cord injury" Cell Commun Adhes. 2008 May; 15(1):27-42.
23. Ponsaerts, R, De Vuyst, E, Retamal, M, D'hondt, C, Vermeire, D, Wang, N, De Smedt, H, Zimmermann, P, Himpens, B, Vereecke, J, Leybaert, L, Bultynck, G, 2010, "Intramolecular loop/tail interactions are essential for connexin 43-hemichannel activity", FASEB J. 2010 November; 24(11):4378-95.
24. Nedergaard, M.; Tian, G. F.; Takano, T. Treatment and prevention of epilepsy. Publication Number: US20100029613A1, Publication Date: 2010 Feb. 4, Application Number: US2007719238A, Application Date: 2008 Aug. 22, Assignee/Applicant: University of Rochester, Rochester, N.Y., US.
25. Mouthon, F.; Charveriat, M.; Deslys, J-P.; Iris, F. Use of anti-connexin agents for modulating the therapeutic effect of psychotropic drugs. Publication Number: EP2344146A1, Publication Date: 2011 Jul. 20, Application Number: EP2009782881A, Application Date: 2009 Sep. 10, Assignee/Applicant: Commissariat à l'Énergie Atomique et aux Énergies Alternatives, 75015 Paris, FR, 101237959; Bio Modeling Systems ou Bmsystems, 75015 Paris, FR, 101237960.
26. Domercq Garcia, M.; Matute Almau, C. Methods and compositions for the treatment of ischemia. Publication Number: EP2322149A1; Publication Date: 2011 May 18; Application Number: EP2009382239A; Application Date: 2009 Nov. 3; Assignee/Applicant: Universidad del Pais Vasco, 48940 Leioa Vizcaya, ES,100829271.
27. Green, C. R.; Becker, D. L. Anti-connexin compounds and uses thereof. Publication Number: WO02006134494A2, Publication Date: 2006 Dec. 21, Application Number: WO2006IB1961A, Application Date: 2006 Feb. 3, Assignee/Applicant: Coda Therapeutics Limited, NZ.
28. Haydon, P. G.; Halassa, M. M.; Fellin, T.; Ding, S.; Zhu, Y. Methods for treating neurological and psychiatric conditions. Publication Number: WO2007002285A2, Publication Date: 2007 Jan. 4, Application Number: WO2006US24303A, Application Date: 2006 Jun. 21, Assignee/Applicant: The Trustees of the University of Pennsylvania, US.
29. Nagy J I, Patel D, Ochalski P A, Stelmack G L. Connexin30 in rodent, cat and human brain: selective expression in gray matter astrocytes, co-localization with connexin43 at gap junctions and late developmental appearance. Neuroscience. 1999 January; 88(2):447-68
30. Rouach, N., Koulakoff, A., Abudara, V., Willecke, K., and Giaume, C., 2008, "Astroglial metabolic networks sustain hippocampal synaptic transmission", *Science*. 322, 1551-1555.
31. Haydon, P. G., and Carmignoto, G., 2006, "Astrocyte control of synaptic transmission and neurovascular coupling", *Physiol Rev* 86. 1009-1031.
32. Frisch C, Theis M., De Souza Silva M A., Dere E., Söhl G., Teubner B., Namestkova K., Willecke K., Huston J P., 2003, "Mice with astrocyte-directed inactivation of connexin43 exhibit increased exploratory behaviour, impaired motor capacities, and changes in brain acetylcholine levels", *Eur J Neurosci* 18, 2313-2318.
33. Perea, G., and Araque, A., 2010, "GLIA modulates synaptic transmission", *Brain Res Rev.* 63, 93-102.
34. Jiang, S., Yuan, H., Duan, L., Cao, R., Gao, B., Xiong, Y. F., Rao, Z. R., 2011, "Glutamate release through connexin 43 by cultured astrocytes in a stimulated hypertonicity model", *Brain Res* 1392, 8-15.
35. Garré, J. M., Retamal, M. A., Cassina, P., Barbeito, L., Bukauskas, F. F., Sáez, J. C., Bennett, M V, and Abudara V., 2010, "FGF-1 induces ATP release from spinal astrocytes in culture and opens pannexin and connexin hemichannels", *Proc Natl Acad Sci USA*. 28, 22659-22664.
36. Iwabuchi, S., Kawahara, K., 2011, "Functional significance of the negative-feedback regulation of ATP release via pannexin-1 hemichannels under ischemic stress in astrocytes", *Neurochem Int* 58, 376-384.
37. Iglesias, R., Dahl, G., Qiu, F., Spray, D. C., Scemes, E., 2009, "Pannexin 1: the molecular substrate of astrocyte "hemichannels"", *J Neurosci* 29, 7092-7097.
38. Perea, G., and Araque, A., 2007, "Astrocytes potentiate transmitter release at single hippocampal synapses", *Science*. 317, 1083-1086.
39. Araque, A., Parpura, V., Sanzgiri, R. P., Haydon, P. G., 1999, "Tripartite synapses: glia, the unacknowledged partner", *Trends Neurosci.* 22, 208-15.
40. Bowser, D. N., and Khakh, B. S., 2004, "ATP excites interneurons and astrocytes to increase synaptic inhibition in neuronal networks. *J. Neurosci.* 24, 8606-8620.
41. Florian, C., Vecsey, C. G., Halassa, M. M., Haydon, P. G., and Abel, T., 2011, "Astrocyte-derived adenosine and A1 receptor activity contribute to sleep loss-induced deficits in hippocampal synaptic plasticity and memory in mice", J Neurosci. 31, 6956-62.
42. Bushong, E. A., Martone, M. E., Jones, Y. Z., and Ellisman, M. H., 2002, "Protoplasmic astrocytes in CA1 stratum radiatum occupy separate anatomical domains", *J Neurosci.* 22, 183-192.
43. Welsh, D. K., and Reppert, S. M., 1996, "Gap junctions couple astrocytes but not neurons in dissociated cultures of rat suprachiasmatic nucleus", *Brain Res.* 706, 30-36.
44. Rash, J. E., Yasumura, T., Dudek, F. E., and Nagy, J. I., 2001, "Cell-specific expression of connexins and evidence of restricted gap junctional coupling between glial cells and between neurons", *J Neurosci.* 21, 1983-2000.

45. Söhl, G., Maxeiner, S., and Willecke, K., 2005, "Expression and functions of neuronal gap junctions", *Nat Rev Neurosci.* 6, 191-200.
46. Ponsaerts R, Wang N, Himpens B, Leybaert L, Bultynck G., 2012, "The contractile system as a negative regulator of the connexin 43 hemichannel", Biol Cell. doi: 10.1111/boc.201100079.
47. Yasumura, T., Dudek, F. E., and Nagy, J. I., 2001, "Cell-specific expression of connexins and evidence of restricted gap junctional coupling between glial cells and between neurons", *J Neurosci.* 21, 1983-2000.
48. Giaume, C., Koulakoff, A., Roux, L., Holcman, D., Rouach, N., 2010, "Astroglial networks: a step further in neuroglial and gliovascular interactions" *Nat Rev Neurosci* 11, 87-99.
49. Orellana, J. A., Hernández, D. E., Ezan, P., Velarde, V., Bennett, M. V., Giaume, C., and Sáez, J. C., 2010, "Hypoxia in high glucose followed by reoxygenation in normal glucose reduces the viability of cortical astrocytes through increased permeability of connexin 43 hemichannels", *Glia.* 58, 329-43.
50. Sáez, J. C., Schalper, K. A., Retamal, M. A., Orellana, J. A., Shoji, K. F., and Bennett, M. V., 2010, "Cell membrane permeabilization via connexin hemichannels in living and dying cells", Exp Cell Res. 316, 2377-2389.
51. LeDoux, J., 2007, "The amygdala", *Curr Biol.* 17, R868-874.
52. Juszczak, G. R., and Swiergiel, A. H., 2009, "Properties of gap junction blockers and their behavioural, cognitive and electrophysiological effects: animal and human studies", *Prog Neuropsychopharmacol Biol Psychiatry.* 33, 181-198.
53. Evans, W. H., and Leybaert, L., 2007, "Mimetic peptides as blockers of connexin channel-facilitated intercellular communication", Cell Commun Adhes 14, 265-273.
54. Nagy J I., Li X., Rempel J., Stelmack G., Patel D., Staines W A., Yasumura T., Rash J E., 2001, "Connexin26 in adult rodent central nervous system: demonstration at astrocytic gap junctions and colocalization with connexin30 and connexin43", *J Comp Neurol* 441, 302-323.
55. Lee, S., Yoon, B. E., Berglund, K., Oh S. J., Park, H., Shin, H. S., Augustine, G. J., and Lee, C. J., 2010, "Channel-mediated tonic GABA release from glia", *Science.* 5, 790-6.
56. Rudkouskaya, A., Chernoguz, A., Haskew-Layton, R. E., and Mongin, A. A., 2008, "Two conventional protein kinase C isoforms, alpha and beta I, are involved in the ATP-induced activation of volume-regulated anion channel and glutamate release in cultured astrocytes", *J Neurochem.* 1, 2260-70.
57. Görg, B., Morwinsky, A., Keitel, V., Qvartskhava, N., Schrör, K., and Haiussinger, D., 2010, "Ammonia triggers exocytotic release of L-glutamate from cultured rat astrocytes", *Glia.* 15, 691-705.
58. Rash J E., Yasumura T., Davidson K G., Furman C S., Dudek F E., Nagy J I., 2001, "Identification of cells expressing Cx43, Cx30, Cx26, Cx32 and Cx36 in gap junctions of rat brain and spinal cord", *Cell Commun Adhes* 8, 315-320.
59. Gosejacob D., Dublin P., Bedner P., Hüttmann K., Zhang J., Tress O., Willecke K., Pfrieger F., Steinhäuser C., Theis M., 2011, "Role of astroglial connexin30 in hippocampal gap junction coupling", *Glia* 59, 511-519. doi: 10.1002/glia.21120.
60. Alves S H, Pinheiro G, Motta V, Landeira-Fernandez J, Cruz A P Anxiogenic effects in the rat elevated plus-maze of 5-HT(2C) agonists into ventral but not dorsal hippocampus. Behav Pharmacol. 2004 February; 15(1):37-43.
61. Carrigan C N, Imperiali B. The engineering of membrane permeable peptides. *Anal Biochem* 341:290-298. doi:10.1016/j. ab.2005.03.026.
62. Wang N, De Vuyst E, Ponsaerts R, Boengler K, Palacios-Prado N, Wauman J, Lai C P, De Bock M, Decrock E, Bol M, Vinken M, Rogiers V, Tavernier J, Evans W H, Naus C C, Bukauskas F F, Sipido K R, Heusch G, Schulz R, Bultynck G, Leybaert L. Selective inhibition of Cx43 hemichannels by TAT-Gap19 and its impact on myocardial ischemia/reperfusion injury. *Basic Res Cardiol.* 2013 January; 108(1):309. doi: 10.1007/s00395-012-0309-x.
63. Ryan P J, Büchler E, Shabanpoor F, Hossain M A, Wade J D, Lawrence A J, Gundlach A L. Central relaxin-3 receptor (RXFP3) activation decreases anxiety- and depressive-like behaviours in the rat. Behav Brain Res. 2013 May 1; 244:142-51. doi: 10.1016/j.bbr.2013.01.034.
64. Enkel T, Thomas M, Bartsch D. Differential effects of subchronic Phencyclidine on anxiety in the light-enhanced startle—, light/dark exploration—and open field tests. Behav Brain Res. 2013 Apr. 15; 243:61-5. doi: 10.1016/j.bbr.2012.12.060.
65. Nagy J I, Patel D, Ochalski P A, Stelmack G L "Connexin30 in rodent, cat and human brain: selective expression in gray matter astrocytes, co-localization with connexin43 at gap junctions and late developmental appearance". Neuroscience 1999 January; 88(2):447-68.
66. Porsolt R D, Bertin A, Jalfre M. "Behavioural despair" in rats and mice: strain differences and the effects of imipramine. Eur. J. Pharmacol. 1978 51, 291-294.
67. Nagy J I, Ochalski P A, Li J, Hertzberg E L. Evidence for the co-localization of another connexin with connexin-43 at astrocytic gap junctions in rat brain. Neuroscience. 1997 May; 78(2):533-48.
68. Huang Y, Grinspan J B, Abrams C K, Scherer S S. Pannexin1 is expressed by neurons and glia but does not form functional gap junctions. Glia 2007; 55:46 56.

The invention claimed is:

1. A method of treating mood disorders comprising administering to a mammal or human a therapeutically effective amount of a compound or a pharmaceutically acceptable salt thereof, that modulates astrocytic release of substances through connexin 30 and connexin 43 hemichannels and pannexin hemichannels without influencing or disturbing the function of gap junctions wherein the compound is cacotheline: (2,3-Dihydro-4-nitro-2,3-dioxo-9,10-secostrychnidin-10-oic acid) or pharmaceutically acceptable salts thereof.

2. The method according to claim 1, wherein the connexin hemichannels correspond to connexin 30 and connexin 43 hemichannels and the pannexin hemichannels correspond to pannexin 1 hemichannels.

3. The method according to claim 1, wherein the compound differentially modulates, blocks, opens, inhibits, and/or activates connexin and/or pannexin hemichannels or a combination thereof from astrocytes while not affecting gap junctions directly.

4. The method according to claim 1, wherein the compound interferes with functioning of connexins or pannexins or a combination thereof in their hemichannel configuration.

5. The method according to claim 4, wherein the compound interferes with functioning of connexin 30 or connexin 43 or pannexin 1 or a combination thereof in their hemichannel configuration.

6. The method according to claim 2, wherein the compound specifically affects connexin 43 or connexin 30 or pannexin 1 hemichannels or a combination thereof in the astrocytes without affecting gap junctions.

7. The method according to claim 2, wherein the subjects to be treated with the method are human.

* * * * *